(12) United States Patent
Simmonds et al.

(10) Patent No.: US 8,318,421 B2
(45) Date of Patent: Nov. 27, 2012

(54) HEPATITIS-C VIRUS TESTING

(75) Inventors: Peter Simmonds, Edinburgh (GB);
Shiu-Wan Chan, Cambridge (GB);
Peng Lee Yap, Edinburgh (GB)

(73) Assignee: Common Services Agency, Edinburgh (GB)

( * ) Notice: Subject to any disclaimer, the term of this patent is extended or adjusted under 35 U.S.C. 154(b) by 29 days.

(21) Appl. No.: 13/180,082

(22) Filed: Jul. 11, 2011

(65) Prior Publication Data

US 2011/0287410 A1 Nov. 24, 2011

Related U.S. Application Data

(60) Division of application No. 12/728,030, filed on Mar. 19, 2010, now Pat. No. 7,976,849, which is a division of application No. 11/652,862, filed on Jan. 12, 2007, now Pat. No. 7,709,006, which is a continuation of application No. 10/396,964, filed on Mar. 25, 2003, now Pat. No. 7,179,470, which is a continuation of application No. 09/039,130, filed on Mar. 13, 1998, now abandoned, which is a division of application No. 08/244,116, filed on Jul. 15, 1994, now Pat. No. 5,763,159, which is a continuation of application No. PCT/GB92/02143, filed on Nov. 20, 1992.

(30) Foreign Application Priority Data

Nov. 21, 1991 (GB) .................................... 9124696.7
Jun. 24, 1992 (GB) .................................... 9213362.8

(51) Int. Cl.
*C12Q 1/70* (2006.01)
*C12Q 1/68* (2006.01)
*C12P 19/34* (2006.01)
*C07H 21/04* (2006.01)

(52) U.S. Cl. ............ 435/5; 435/6.1; 435/6.11; 435/6.12; 435/91.1; 435/91.21; 536/24.3; 536/24.32; 536/24.33

(58) Field of Classification Search ........................ None
See application file for complete search history.

(56) References Cited

U.S. PATENT DOCUMENTS

| 5,372,928 | A | 12/1994 | Miyamura et al. |
| 5,428,145 | A | 6/1995 | Okamoto et al. |
| 5,747,239 | A | 5/1998 | Wang et al. |

FOREIGN PATENT DOCUMENTS

| EP | 0 318 216 A1 | 5/1989 |
| EP | 0 388 232 A1 | 9/1990 |
| EP | 0 398 748 A2 | 11/1990 |
| EP | 0 414 475 A1 | 2/1991 |
| EP | 0 435 229 A1 | 7/1991 |
| EP | 0 442 394 A2 | 8/1991 |
| EP | 0 445 423 A2 | 9/1991 |
| EP | 0 464 287 A1 | 1/1992 |
| EP | 0 468 527 A2 | 1/1992 |
| WO | WO 92/02642 | 2/1992 |
| WO | WO 92/19743 | 11/1992 |
| WO | WO 94/25601 | 11/1994 |
| WO | WO 94/27153 | 11/1994 |

OTHER PUBLICATIONS

Abrignani, S., et al., "Perspectives for a vaccine against hepatitis C virus," *Journal of Hepatology*, 1999, vol. 31(Suppl. 1), pp. 259-263.
Alberti et al., "Diagnosis of Hepatitis C Facts and Perspectives," *Journal of Hepatology*, 1991, pp. 279-282, vol. 12.
Bradley, D.W., "Virology, Molecular Biology, and Serology of Hepatitis C Virus," *Transfusion Medicine Reviews*, 1992, pp. 93-102, vol. VI(2).
Bukh, J., et al., "Sequence Analysis of the 5'Noncoding Region of Hepatitis C Virus," *Proc. Natl. Acad. Sci.*, 1992, pp. 4942-4946, vol. 89.
Bukh et al., "Sequence Analysis of the Core Gene of 14 Hepatitis C Virus Genotypes," *Proc. Natl. Acad. Sci. USA*, Aug. 1994, pp. 8239-8242, vol. 91.
Chan, S., et al., "Serological Responses to Infection with Three Different Types of Hepatitis C Virus," *The Lancet*, 1991, p. 1391, vol. 338.
Chan, S.W., et al., "Analysis of a New Hepatitis C Virus Type and Its Phylogenetic Relationship to Existing Variants," *Journal of General Virology*, 1992, pp. 1131-1141, vol. 73.
Chomczynski et al., "Single-Step Method of RNA Isolation by Acid Guanidinium Thiocyanate-Phenol-Chloroform Extraction," *Analytic Biochemistry*, 1987, pp. 156-159, vol. 162.
Choo et. al., "Isolation of a cDNA Clone Derived from a Blood-Borne Non-A, Non-B Viral Hepatitis Genome," *Science*, Apr. 21, 1989, pp. 359-362, vol. 244.
Choo et. Al., "Genetic Organization and Diversity of the Hepatitis C Virus," *Proc. Natl. Acad. Sci. USA*, Mar. 1991, pp. 2451-2455, vol. 88.
Clarke et al., "Improved Immunogenicity of a Peptide Epitope After Fusion to Hepatitis B Core Protein," *Nature*, Nov. 26, 1987, pp. 381-384, vol. 330.
Coelen et al., "The 5'—Tthermal Non-Coding Region of Murray Valley Encephalitis Virus RNA is Highly Conserved," *Journal of General Virology*, 1990, pp. 241-245, vol. 71.
Devereux et al., "A Comprehensive Set of Sequence Analysis Programs for the VAX," *Nucleic Acids Research*, 1984, pp. 387-395, vol. 12, No. 1.
Encke, J., et al., "Development of a heterologous, multigenotype vaccine against hepatitis C virus infection," *European Journal of Clinical Investigation*, 2007, vol. 37, pp. 396-406.
Enomoto, N., et al., "There Are Two Major Types of Hepatitis C Virus in Japan," *Biochemical and Biophysical Research Communications*, 1990, pp. 1021-1025, vol. 170.

(Continued)

*Primary Examiner* — Louise Humphrey
(74) *Attorney, Agent, or Firm* — Alston & Bird LLP

(57) ABSTRACT

New styles of hepatitis C virus (HCV), referred to as HCV-3 and HCV-4, have been identified and sequenced. Antigenic regions of HCV-2, HCV-3 and HCV-4 polypeptides have been identified. Immunoassays for HCV and antibodies thereto are described, which allow more complete screening of blood samples for HCV, and allow HCV genotyping.

1 Claim, 39 Drawing Sheets

OTHER PUBLICATIONS

Esteban et al., "Evaluation of Antibodies to Hepatitis C Virus in a Study of Transfusion-Associated Hepatitis," *N. Engl. J. Med.*, Oct. 18, 1990, pp. 1107-1112, vol. 323, No. 16.

Fagan, E. A., "Testing for Hepatitis C Virus," *BMJ*, Sep. 7, 1991, pp. 535-536, vol. 303.

Felsenstein, "Phylogenies From Molecular Sequences: Inference and Reliability," Annu. Rev. Genet, 1988, pp. 521-565, vol. 22.

Follet, E.A.C., et al., "HCV Confirmatory Testing of Blood Donors," *The Lancet*, Oct. 19, 1991, p. 1024, vol. 338.

Fuchs et al., "Characterization of Nucleotide Sequences from European Hepatitis C Virus Isolates," *Gene.*, 1991, pp. 163-169, vol. 103.

Garson et al., "Enhanced Detection by PCR of Hepatitis C Virus RNA," *The Lancet*, Oct. 6, 1990, pp. 878-879, vol. 336.

Geysen et al., "Use of Peptide Synthesis to Probe Viral Antigens for Epitopes to a Resolution of a Single Amino Acid" *Proc. Natl. Acad. Sci. USA*, Jul. 1984, pp. 3998-4002, vol. 81.

Geysen et al., "Small Peptides Induce Antibodies with a Sequence and Structural Requirement for Binding Antigen Comparable to Antibodies Raised Against the Native Protein," *Proc. Natl. Acad. Sci. USA*, Jan. 1985, pp. 178-182, vol. 82.

Han et al., "Characterization of the Terminal Regions of Hepatitis C Viral RNA: Identification of Conserved Sequences in the 5' Untranslated Region and Poly(A) Tails at the 3' End," *Proc. Natl. Acad. Sci. USA*, Mar. 1991, pp. 1711-1715, vol. 88.

Hosein et al., "Improved Serodiagnosis of Hepatitis C Virus Infection with Synthetic Peptide Antigen from Capsid Protein," *Proc. Natl. Acad. Sci. USA*, May 1991, pp. 3647-3651, vol. 88.

Houghton, M., and Abrignani, S., "Prospects for a Virus Against the Hepatitis C Virus," *Nature*, 2005, pp. 961-966, vol. 436.

Japanese Red Cross Non-A, Non-B Hepatitis Research Group, "Effect of Screening for Hepatitis C Virus Antibody and Hepatitis B Virus Core Antibody on Incidence of Post-Transfusion Hepatitis," *The Lancet*, Oct. 26, 1991, pp. 1040-1041, vol. 338.

Kato et al., "Molecular Cloning of the Human Hepatitis C Virus Genome from Japanese Patients with Non-A, Non-B Hepatitis," *Proc. Natl. Acad. Sci. USA*, Dec. 1990, pp. 9524-9528, vol. 87.

Kubo et al., "A cDNA Fragment of Hepatitis C Virus Isolated from an Implicated Donor of Post-Transfusion Non-A, Non-B Hepatitis in Japan," *Nucleic Acids Research*, 1989, pp. 10367-10372, vol. 17, No. 24.

Kuo et al., "An Assay for Circulating Antibodies to a Major Etiologic Virus of Human Non-A, Non-B Hepatitis," *Science*, Apr. 21, 1989, pp. 362-364, vol. 244.

Laín et al., "Homologous Potyvirus and Flavivirus Proteins Belonging to a Superfamily of Helicase-Like Proteins," *Gene*, 1989, pp. 357-362, vol. 82.

Madl et al., "Sequence of the Structural Proteins of Tick-Borne Encephalitis Virus (Western Subtype) and Comparative Analysis with Other Flaviviruses," *Virology*, 1988, pp. 197-205, vol. 166.

Miller et al., "Hepatitis C Virus Shares Amino Acid Sequence Similarity with Pestiviruses and Flaviviruses as well as Members of Two Plant Virus Supergroups," *Proc. Natl. Acad. Sci. USA*, Mar. 1990, pp. 2057-2061, vol. 87.

Muraiso et al., "A Structural Protein of Hepatitis C Virus Expressed in *E. coli* Facilitates Accurate Detection of Hepatitis C Virus," *Biochemical and Biophysical Research Communications*, Oct. 30, 1990, pp. 511-516, vol. 172, No. 2.

Nakao, T., et al., "Typing of Hepatitis C Virus Genomes by Restriction Fragment Length Polymorphism," *Journal of General Virology*, 1991, pp. 2105-2112, vol. 72.

Ogata et al., "Nucleotide Sequence and Mutation Rate of the H Strain of Hepatitis C Virus," *Proc. Natl. Acad. Sci. USA*, Apr. 1991, pp. 3392-3396, vol. 88.

Okamoto et al., The 5'-Terminal Sequence of the Hepatitis C Virus Genome,: *Japan, J. Exp. Med.*, 1990, pp. 167-177, vol. 60.

Okamoto et al., "Detection of Hepatitis C Virus RNA by a Two-Stage Polymerase Chain Reaction with Two Pairs of Primers Deduced from the 5'-Noncoding Region," *Japan, J. Exp. Med.*, 1990, pp. 215-222, vol. 60.

Okamoto, H., et al., "Full-Length Sequence of a Hepatitis C Virus Genome Having Poor Homology to Reported Isolates: Comparative Study of Four Distinct Genotypes," *Virology*, 1992, pp. 331-341, vol. 188.

Okamoto, H., et al., Nucleotide Sequence of the Genomic RNA of Hepatitis C Virus Isolated from a Human Carrier: Comparison with Reported Isolates for Conserved and Divergent Regions, *Journal of General Virology*, 1991, pp. 2697-2704, vol. 72.

Ou-Yang, P., et al., "Co-Delivery of GM-CSF Gene Enhances the Immune Responses of Hepatitis C Viral Core Protein-Expressing DNA Vaccine: Role of Dendritic Cells," *Journal of Medical Virology*, 2002, vol. 66, pp. 320-328.

Pozzato et al., "Severity of Liver Disease with Different Hepatitis C Viral Clones," *The Lancet*, Aug. 24, 1991, pp. 509, vol. 338.

Saitou et al., "Relative Efficiencies of the Fitch-Margoliash, Maximum-Parsimony, Maximum-Likelihood, Minimum-Evolution, and Neighbor-joining Methods of Phylogenetic Tree Construction in Obtaining the Correct Tree," *Mol. Biol. Evol.*, 1989, pp. 514-525, vol. 6(5).

Simmonds et al., "Human Immunodeficiency Virus-Infected Individuals Contain Provirus in Small Numbers of Peripheral Mononuclear Cells and at Low Copy Numbers," *Journal of Virology*, Feb. 1990, pp. 864-872, vol. 64, No. 2.

Simmonds, P., et al., "Hepatitis C Quantification and Sequencing in Blood products, Haemophiliacs, and Drug Users," *The Lancet*, 1990, pp. 1469-1472, vol. 336.

Simmonds, P., et al., "Mapping of Serotype-Specific, Immunodominant Epitopes in the NS-4 Region of Hepatitis C Virus (HCV): Use of Type-Specific Peptides to Serologically Differentiate Infections with HCV Types 1, 2, and 3," *Journal of Clinical Microbiology*, 1993, vol. 31(6), pp. 1493-1503.

Staden, "Graphic Methods to Determine the Function of Nucleic Acid Sequences," *Nucleic Acids Research*, 1984, pp. 521-538, vol. 12, No. 1.

Takamizawa et al., "Structure and Organization of the Hepatitis C Virus Genome Isolated from Human Carriers" *Journal of Virology*, Mar. 1991, pp. 1105-1113, vol. 65, No. 3.

Takeuchi et al., "Nucleotide Sequence of Core and Envelope Genes of the Hepatitis C Virus Genome Derived Directly from Human Healthy Carriers," *Nucleic Acids Research*, 1990, pp. 4626, vol. 18, No. 15.

Tam, "Synthetic Peptide Vaccine Design: Synthesis and Properties of a High-Density Multiple Antigenic Peptide System," *Proc. Natl. Acad. Sci. USA*, Aug. 1988, pp. 5409-5413, vol. 85.

Tsukiyama-Kohara et al., "A Second Group of Hepatitis C Viruses," *Virus Genes*, 1991, pp. 243-254, vol. 5:3.

Van Der Poel et al., "Confirmation of Hepatitis C Virus Infection by New Four-Antigen Recombinant Immunoblot Assay," *The Lancet*, Feb. 9, 1991, pp. 317-319, vol. 337.

Weiner et al., (Jan. 6, 1990) "Detection of Hepatitis C Viral Sequences in Non-A, Non-B Hepatitis," *The Lancet*, Jan. 6, 1990, pp. 1-3, vol. 335.

TO FIG. 1C.

| | -255 | | -235 | | -215 | | -195 | |
|---|---|---|---|---|---|---|---|---|
| | GGCGTTAGTA | CCAGTGTCGT | GCAGCCTCCA | GGACTCCCCC | TCCCGGGAGA | GCCATAGTGG | TCTGCGGAAC | |
| E-b1 | ......... | ......... | ......... | ......... | ......... | ......... | ......... | |
| E-b2 | ......... | ......... | ......... | ......... | ......... | ......... | ......... | |
| E-b3 | ......... | ......... | ......... | ......... | ......... | ......... | ......... | |
| E-b4 | ......... | ......... | ......... | ......... | ......... | ......... | ......... | |
| E-b5 | ......... | ......... | ......... | ...C..... | ......... | ......... | ......... | |
| E-b6 | ......... | ......... | ......... | ...C..... | ......... | ......... | ......... | |
| E-b7 | ......... | ......... | ......... | ..CC..... | ......... | ......... | ......... | |
| E-b8 | ......... | ......... | ......... | ...C..... | ......... | ......... | ......... | |
| 2 K2a | ......... | T......A. | ......... | ..CC..... | ......... | ......... | ......... | |
| E-b9 | ......... | T........ | A........ | ..CC..... | ......... | ......... | ......... | |
| E-b10 | ......... | T........ | A........ | ..CC..... | ......... | ......... | ......... | |
| E-b11 | ......... | T........ | A........ | ..CC..... | ......... | ......... | ......... | |
| E-b12 | ......... | T........ | A........ | ..CC..... | ......... | ......... | ......... | |
| 2 K2b-1 | ......... | T......A. | ......... | ..CC..... | ......... | ......... | ......... | |
| E-b13 | ......... | T........ | ......... | ...C..... | ......... | ......... | ......... | |
| E-b14 | ......... | T........ | ......... | ...C..... | ......... | ......... | ......... | |
| E-b15 | ......... | T........ | ......... | ...C..... | ......... | ......... | ......... | |
| E-b16 | ......... | T........ | ......... | ...C..... | ......... | ......... | ......... | |
| E-b17 | ......... | T........ | ......... | ...C..... | ......... | ......... | ......... | |
| E-b18 | ......... | T........ | ......... | ...C..... | ......... | ......... | ......... | |

FROM FIG. 1C.

| .CA..AC.. | .CA..AC.. | .CA..AC.. | .CA..AC.. | .CA..AC.. | .CA..AC.. | .CA..AC.. | .C...AG.. | .C...A... | .CA..A... | .CA..AC.. | .CA..AC.. | .CA..AC.. | .CA..AC.. | .CA..AC.. |
|---|---|---|---|---|---|---|---|---|---|---|---|---|---|---|
| .T......... | .T......... | .T......... | .T......... | .T......... | .T......... | .T......... | .T......... | .T......... | .T......... | .T......... | .T......... | .T......... | .T......... | .T......... |

FROM FIG. 1B.

TO FIG. 1G.

| | -155 | | -135 | | -115 | | -195 |
|---|---|---|---|---|---|---|---|
| | CGGGTCCTTT | CTTGGAGCAA | CCCGCTCAAT | ACCCAGAAAT | TTGGGCGTGC | CCCCGCGAGA | TCACTAGCCG |
| E-b1 | .......... | .......... | .......... | .......... | .......... | .......... | .......... |
| E-b2 | .......... | .......... | .......... | .......... | .......... | .......... | .......... |
| E-b3 | .......... | .......... | .......... | .......... | .......... | .......... | .......... |
| E-b4 | .......... | .......... | .......... | .......... | .......... | .......... | .......... |
| E-b5 | .......... | .......... | .......... | .......... | .......... | .......... | .......... |
| E-b6 | .......... | ........A. | .......... | .......... | .......... | .......A.. | .......... |
| E-b7 | .......... | .......... | .......... | .......... | .......... | .......... | ......C... |
| E-b8 | .......... | .......... | .......... | .......... | .......... | .......... | .......... |
| K2a | T......... | .......TA. | .....A..T. | G...G.TC.. | .......... | .......A.. | CTG....... |
| E-b9 | T......... | .......TA. | .....A..T. | G...G.CC.. | .......... | .......A.. | CTG....... |
| E-b10 | T......... | .......TA. | .....A..T. | G...G.CC.. | .......... | .......A.. | CTG....... |
| E-b11 | T......... | .......TA. | .....A..T. | GT..G.TC.. | .......... | .......A.. | CTG....... |
| E-b12 | T......... | .......TA. | .....A..T. | GT..G.TC.. | .......... | .......A.. | CTG......T |
| K2b-1 | T......... | .......TA. | .......... | GT..G.TC.. | .......... | .......A.. | CTG....... |
| E-b13 | .......... | .......T.. | .......... | G...TG.C.. | .......... | .......A.. | CTG....... |
| E-b14 | .......... | .......T.. | .......... | G...TG.C.. | .......... | .......A.. | CTC....... |
| E-b15 | .......... | .......TT. | .......... | G...TG.C.. | .......... | .......A.. | CTG....... |
| E-b16 | .......... | .......TT. | .......... | G...TG.C.. | .......... | .......A.. | CTC....... |
| E-b17 | .......... | .......T.. | .......... | G...TG.C.. | .......... | .......A.. | CTC....... |
| E-b18 | .......... | .......T.. | .......... | G...TG.C.. | .......... | .......A.. | CTC....... |

TO FIG. 1F.

| FIG. 1E. | FIG. 1G. |
|---|---|
| FIG. 1F. | FIG. 1H. |

| | | | | | | | |
|---|---|---|---|---|---|---|---|
| HCV-1 | | | | G..TG..G | | | CTG |
| Pt-1 | | T | | G..TG..G | | A | CTG |
| H77 | | TA | | G..TG..G | | A | CTG |
| H90 | | TA | | G..TG..G | | A | CTG |
| GM1 | | TA | | G..TG..G | | A | CTG |
| GM2 | | TA | | G..TG..G | | A | CTG |
| J1 | | TA | | G..TG..G..C | C | A | CTG |
| A1 | | TA | | G..TG..G | | A | CTG |
| S1 | | TA | | G..TG..G..C | | A | CTG |
| T1 | | TA | | G..TG..G..C | | A | CTG |
| U18/I24 | | T | | G..TG..G | | | CTG |
| HCV-J | | T | | G..TG..G | | | CTG |
| HCV-BK | | TA | | G..TG..G | C | A | CTG |
| HC-J1 | | T | | G..TG..G | | | CTG |
| HC-J4 | | | | G..TG..G | | | CTG |

FROM FIG. 1E.

| -62 ▶ | GGCC | : : : : : : : : | | : : : : : : : : | | : : : : : : : : |
|---|---|---|---|---|---|---|
| | GGTCGCGAAA | : : : : : : : : | | T : : : :<br>T : : : :<br>T : : : :<br>T : : : : | | : : : : : : : : |
| -75 ▶ | AGTAGTGTTG | : : : : : : : : | | C : : : :<br>C : : : :<br>C : : : :<br>C : : : : | | : : : : : : : : |

FROM FIG. 1E.

TO FIG. 1H.

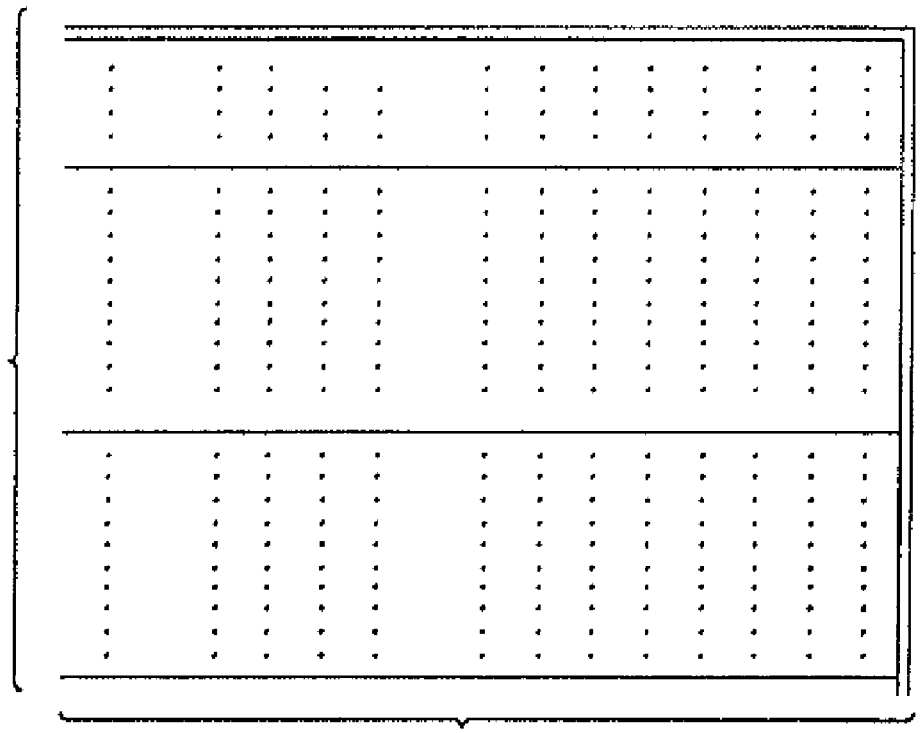

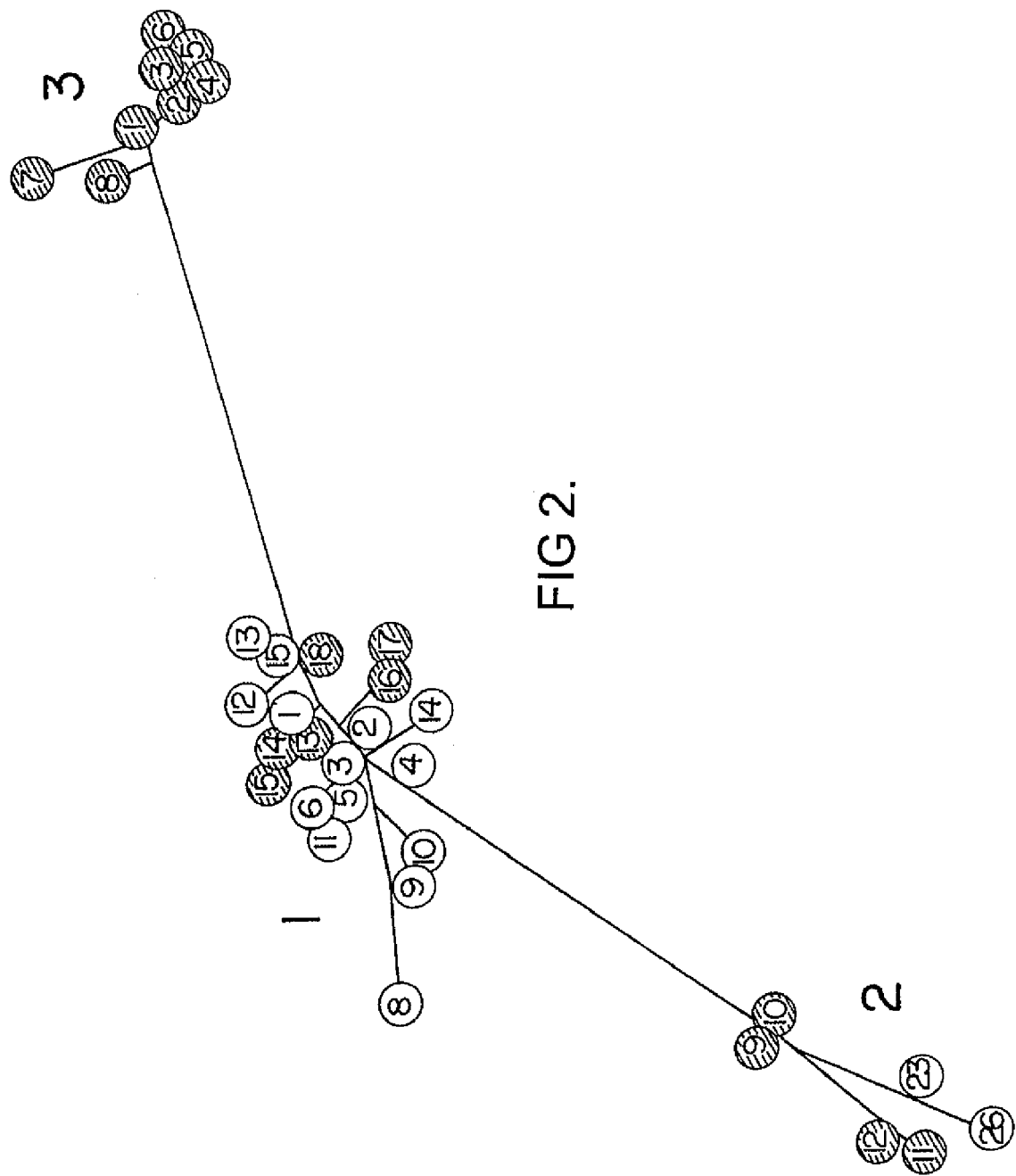

FIG. 3.

| | | VTEQDIRVEE | EIYQCCNLEP | EARKVISSLT | ERLYCGGPMF | NSKGAQCGYR | RCRASGVLPT | SFGNTITCYI | KATAACEAAG | LRNPD |
|---|---|---|---|---|---|---|---|---|---|---|
| | | ▸2648 | | ▸2668 | | ▸2688 | | ▸2708 | | |
| | E-b1 | .......... | .......... | .......... | .......... | .......... | .......... | .......... | .......... | ..... |
| | E-b2 | .......... | .......... | .......... | .......... | .......... | .......... | .......... | .......... | ..... |
| | E-b3 | .......... | .......... | .......... | .......... | .......... | .......... | .......... | ......K... | ..... |
| | E-b7 | .......... | .......... | .......... | .......... | .......... | .......... | .......... | ......K... | ..... |
| 2 | K2a | ..R...T... | S..RA.S.PE | .HIA.H.... | .....V.... | ......QT.. | ........T. | .M........ | ...L..K... | IVA.S |
| 2 | K2a | ..R...T... | S...A.S.PE | ..TA.H.... | .....V.... | ......QT.. | ........T. | .M........ | ...L..K... | IVA.T |
| | E-b9 | .......... | S...A.S.PQ | ...T.H.... | .....V...T | ......QS.. | ......FT.. | .M...M.... | ...L..K... | IVD.T |
| 2 | K2b-1 | ..R...T... | S...A.S.PQ | .......... | .....V..LT | ......QS.. | ......FT.. | .M...M.... | ...L..K... | IVD.I |
| 2 | K2b-1 | ..R...T... | S...A.S.PE | .......... | .....V..LT | ......QS.. | ......FT.. | .M...M.... | ...L..K... | IVD.I |
| 1 | HCV-1 | ..S...T... | A....D.D.. | .Q..VA.K.. | .....V..LT | .R.EN..... | ........T. | .C...L.... | ...R..R... | .QDCT |
| 1 | Pt-1  | ..S...T... | A....D.D.. | .Q..VA.K.. | .....V..LT | .R.EN..... | ........T. | .C...L.... | ...R..R... | .QDCT |
| 1 | H77   | ..S...T... | A....D.D.. | .Q..VA.K.. | .....V..LT | .R.EN..... | ........T. | .C...L.... | ...R..R... | .QDCT |
| 1 | H90   | ..S...T... | A....D.D.. | .Q..TA.K.. | .....V..LT | .R.EN..... | ........T. | .C...L.... | ...R..R... | .QDCT |
| | E-b17 | ..N...T... | S....QD.A. | .QA.R..... | .....V..LT | ......QN.. | ........T. | .C...L...L | ...S..R..K | .QDCT |
| | E-b18 | ..N...T... | S....D.A.. | .QA.R..... | .....V..LT | ......QN.. | ........T. | .C...L...L | ...R..R..K | .QDCT |
| | E-b18 | ..N...T... | S...SD.A.. | .QA.R..... | .....I..LT | ......QN.. | ........T. | .C...L...L | ...S..R..K | .QDCT |
| | E-b18 | ..N...T... | S...A.A... | .QA.R..... | .....I..LT | ......QN.. | ........T. | .C...L...L | ...S..R..K | .QDCT |
| | E-b18 | ..N...T... | S....D.A.. | .Q..R..... | .....I..LT | ......QN.. | .......... | .C...L...L | ...S..R..K | ..DCT |
| | E-b18 | ..N...T... | S....D.A.. | .KLA.R.... | .....I..LT | ......QN.. | ........T. | .C...L...L | ...S..R..K | .QDCT |
| | E-b18 | ..N...T... | S....D.A.. | .Q..R..... | .....I..LT | ......QN.. | ........T. | .C...L...L | ...S..R..K | .QDCT |

FIG. 5.

| | | 1577 KQQGLNFSYL | TAYQATVCAR | 1597 AQALPPSWDE | TWKCLVRLKP | 1617 TLHGPTPLLY | 1633 RLGPVQN |
|---|---|---|---|---|---|---|---|
| | E-b1 | .......... | .......... | .......... | .......... | .......... | ....... |
| | E-b2 | .......... | .......... | ...P...... | .....M.... | .......... | ....... |
| | E-b6 | .......... | .......... | ...P...... | .......... | .......... | ....... |
| | E-b7 | .......... | .....A.... | ...P...... | .......... | .......... | ....... |
| ? | Clone A | ..G.D..A.. | .......... | .K.P.....V | ...M...A.. | .......I.. | ..A.T.. |
| | E-b6 | ..S.E.LP.. | V......... | ...P.....Q | ...M...I.. | .......... | ...A... |
| | E-b7 | ..S.E.LP.. | V......... | ...P.....Q | ...M...I.. | .......... | ...A... |
| | Group 1/1 | ..S.E.LP.. | V......... | ...P.....Q | ...M...I.. | .......... | ...A... |
| | 1/2 | ..S.E.LP.. | V......... | ...P.....Q | ...M.R.... | .......... | .......  |
| | 1/3 | ..S.E.P... | V......... | ...P.....Q | ...M...... | .......... | ...A... |
| | 1/4 | ..S.E.P... | V......... | ...P.....Q | ...M....A. | .......... | .......  |
| | 1/4 | ..S.E.P... | V......... | ...P...EQ  | ...M....A. | .......... | ...A... |
| 1 | HCV-1 | ..S.E.LP.. | V......... | ...P.....Q | ...M...... | .......... | ...A... |
| 1 | H77   | ..S.E.P... | V......... | ...P.....Q | ...M...I.. | .......... | ...A... |
| 1 | H90   | ..S.E.P... | V......... | ...P.....Q | ...M...I.. | .......... | ...A... |
| 1 | HCV-J | ..A.D.LP.. | V......... | ...P.....Q | ...M...I.. | .......... | ...A... |
| 1 | HCV-BK | ..A.D..P.. | V......... | .K.P.....Q | ...M...I.. | .......... | ...A... |
| 1 | JH    | ..A.D..P.. | V......... | .......... | ...M...I.. | .......... | ...A... |

| E-b1 | AKPQRKTKRN | TIRRPQDVKF | PGGGQIVGGV | YVLPRRGPRL | GVCATRKTSE | RSQPRGRRQP |
|---|---|---|---|---|---|---|
| 1 HCV-1 | P..K.N.... | .N........ | .......... | ...L...... | .......... | .......... |
| 1 H77 | P......... | .N........ | .......... | ...L...... | .........R | .......... |
| 1 H90 | P......... | .N........ | .......... | ...L...... | .........R | .......... |
| 1 GM1 | .......... | .N........ | .......... | ...L...... | .........R | .......... |
| 1 GM2 | .......... | .N........ | .......... | ...L...... | ......R..P | .......... |
| 1 HCV-J | P......... | .N........ | .......... | ...L...... | .........R | .......... |
| 1 HCV-BK | P......... | .N........ | .......... | ...L...... | .........R | .......... |
| 1 HC-J1 | P......... | .N........ | .......... | ...L...... | ......R..P | .......... |
| 1 HC-J4 | P......... | .......... | .......... | ...L...... | .........R | .......... |
| 1 JH | P......... | .N........ | .......... | ...L...... | ......R..P | .......... |
| 1 J7 | P......... | .N........ | .......... | ...L...... | .........R | ........W. |
|   | P......... | .N........ | .......... | ...L...... | .........R | .......... |

FIG. 7A.

| | E-b1 | IPKARRSEGR | SWAQPGYPWP | LYGNEGCGWA | GVLLSPRGSR | PSWGPNDPRR | RSRNLGKVID | TLTW |
|---|---|---|---|---|---|---|---|---|
| | | ▶65 | | ▶85 | | ▶105 | | ▶128 |
| 1 | HCV-1 | .......... | .......... | .......... | .......... | .......... | .......... | .... |
| 1 | H77 | .....P.... | ..T....... | .......... | .......... | .T........ | .......... | ..C. |
| 1 | H90 | .....P.... | ..T....... | .......... | .......... | .T........ | .......... | ..C. |
| 1 | GM1 | .....P.... | ..T....... | .......M.. | .......... | .T........ | .......... | .F.C |
| 1 | GM2 | .....P.... | ..T....... | .......... | .......... | .T........ | .......... | ..C. |
| 1 | HCV-J | .....P.... | ..T....... | .......... | .......... | .T........ | .......... | ..C. |
| 1 | HCV-BK | .....P.... | ..T....... | ......M... | .......... | .T........ | .......... | ..C. |
| 1 | HC-J1 | ..V..P.... | ..T....... | .....L.... | .......... | .......... | .......... | ..C. |
| 1 | HC-J4 | .....P.... | ..T....... | .....L.... | .......... | .T........ | .......... | ..C. |
| 1 | JH | .....P.... | ..T....... | .....L.... | .......... | .T........ | .......... | ..C. |
| 1 | J7 | .....P.... | ..T....... | .....L.... | .......... | .T........ | .......... | ..C. |

FIG. 7B.

NUCLEOTIDE SEQUENCES

```
       4911                                                            4970
        ▼                                                               ▼
T0040  GACACACCCU GUCACAAAAU ACAUCAUGGC AUGCAUGUCA GCUGAUCUGG AAGUAACCAC
T0038  ??CACACCCC GUCACAAAAU ACAUCAUGGC AUGCAUGUCA GCUGAUCUGG AAGUAACCAC
T0036  ??CACACCCC AUCACAAAAU ACAUCAUGGC AUGCAUGUCA GCUGAUCUGG AAGUAACCAC
T0026  ????CACCCC AUCGCAAAAU ACCUCAUGGC AUGUAUGUCA GCUGAUCUGG AAGUAACCAC
T1787  ????CACCCC AUCACAAAAU ACGUCAUGGC AUGCAUGUCA GCUGAUCUGG AAGUAACCAC
       ---------- ---------- ---------- ---------- ---------- ----------
Cons   GACACACCCU GUCACAAAAU ACAUCAUGGC AUGCAUGUCA GCUGAUCUGG AAGUAACCAC
       4971                                                            5030
        ▼                                                               ▼
T0040  CAGCACCUGG GUGUUGCUUG GAGGGGUCCU CGCGGCCCUA GCGGCCUACU GCUUGUCAGU
T0038  CAGCACCUGG GUGUUGCUUG GAGGGGUCCU CGCGGCCCUA GCGGCCUACU GCUUGUCAGU
T0036  CAGCACCUGG GUGUUGCUUG GAGGGGUCCU CGCGGCCCUA GCGGCCUACU GCUUGUCAGU
T0026  CAGCACCUGG GUGUUGCUUG GAGGAGUCCU CGCUGCCCUA GCGGCCUACU GCUUGUCAGU
T1787  CAGCACCUGG GUGUUGCUUG GAGGGGUCCU CGCGGCCCUA GCGGCCUACU GCUUGUCAGU
       ---------- ---------- ---------- ---------- ---------- ----------
Cons   CAGCACCUGG GUGUUGCUUG GAGGGGUCCU CGCGGCCCUA GCGGCCUACU GCUUGUCAGU
       5031                                                            5090
        ▼                                                               ▼
T0040  CGGCUGCGUU GUGAUUGUGG GUCAUAUUGA GCUGGGGGGC AAGCCCGCA  AUCGUUCCAGA
T0038  CGGCUGCGUU GUGAUUGUGG GCCAUAUUGA GCUGGGGGGC AAGCCCGCA  CUCGUUCCAGA
T0036  CGGCUGCGUU GUGAUUGUGG GCCAUAUUGA GCUGGGGGGC AAGCCCGCA  CUCGUUCCAGA
T0026  CGGCUGCGUU GUGAUUGUGG GUCAUAUUGA GCUGGGGGGC AAGCCAGCA  CUCGUUCCAGA
T1787  CGGCUGCGUU GUGAUUGUGG GUCAUAUUGA GCUGGGAGGC AAGCCGGCA  CUCGUUCCAGA
       ---------- ---------- ---------- ---------- ---------- ----------
Cons   CGGCUGCGUU GUGAUUGUGG GUCAUAUUGA GCUGGGGGGC AAGCCCGCA  AUCGUUCCAGA
       5091                                                            5150
        ▼                                                               ▼
T0040  CAAAGAGGUG UUGUAUCAAC AAUACGAUGA GAUGGAGGAG UGCUCGCAA GCUGCCCCAUA
T0038  CAAAGAAGUG UUGUAUCAAC AAUACGAUGA GAUGGAGGAG UGCUCGCAA GCUGCCCCAUA
T0036  CAAAGAGGUG UUGUAUCAAC AAUACGAUGA GAUGGAGGAG UGCUCGCAA GCUGCCCCAUA
T0026  CAAAGAGGUG UUGUAUCAAC AAUACGAUCA GAUGGAGGAG UGCUCGCAA GCUGCCCCAUA
T1787  CAAGGAGGUG UUGUAUCAAC AAUACGAUGA GAUGGAGGAG UGCUCGCAA GCUGCCCCAUA
       ---------- ---------- ---------- ---------- ---------- ----------
Cons   CAAAGAGGUG UUGUAUCAAC AAUACGAUGA GAUGGAGGAG UGCUCGCAA GCUGCCCCAUA
       5051                                                            5210
        ▼                                                               ▼
T0040  UAUCGAACAA GCUCAGGUCA UAGCCCA CA GUUCAAGGAG AAAGUCCUU GGAUUGCUGCA
T0038  UAUCGAACAA GCUCAAGUAA UAGCCCA CA GUUCAAGGAG AAAGUCCUU GGAUUGCUGCA
T0036  UAUCGAACAA GCUCAGGUAA UAGCCCA CA GUUCAAGGAG AAAGUCCUU GGAUUGCUGCA
T0026  UAUCGAACAA GCUCAGGUAA UAGCCCA CA GUUCAAGGAG AAAGUCCUU GGAUUGCUGCA
T1787  UAUCGAACAA GCUCAGGUAA UAGCCCA CA GUUCAAGGAG AAAGUCCUU GGGUUGCUGCA
       ---------- ---------- ------- -- ---------- ---------- ----------
Cons   UAUCGAACAA GCUCAGGUCA UAGCCCA CA GUUCAAGGAG AAAGUCCUU GGAUUGCUGCA
```

FIG. 9A.

```
       5211                                                              5270
        ▼                                                                 ▼
T0040  GCGAGCCACC  CAACAACAAG  CUGUUAU GA  GCCAAUAGUA  GCUACCUAC  UGGCAAAAGCU
T0038  GCGGGCCACC  CAACAACAAG  CUGUUAU GA  GCCCAUAGUA  GCUACCAAC  UGGCAAAAGCU
T0036  GCGAGCCACC  CAACAACAAG  CUGUUAU GA  GCCAAUAGUA  GCUACCAAC  UGGCAAAA???
T0026  GCGAGCCACC  CAACAACAAG  CUGUCAU GA  GCCCAUAGUA  GCUACCAAC  UGGCAAAA???
T1787  GCGAGCCACC  CAACAACAGC  CUGUCAU GA  GCCCAUAGUA  GCUACCAAC  UGGCAAAAGCU
       ----------  ----------  ---------   ----------  ---------  -----------
Cons   GCGAGCCACC  CAACAACAAG  CUGUUAU GA  GCCCAUAGUA  GCUACCAAC  UGGCAAAAGCU
       5271
        ▼
T0040  UGACACC
T0038  UGACGCC
T0036  ???????
T0026  ???????
T1787  UGAGCCU
       -------
Cons   UGACACC
```

FIG. 9B.

DEDUCED AMINO ACID SEQUENCES

```
        1638                                                                      1787
         ▼                                                                         ▼
T0040  THPVT  KYIMA  CMSAD  LEVTT  STWVL  LGCVL  AALAA  YCLSV  GCVVI  VGHIE
T0038  .HPVT  KYIMA  CMSAD  LEVTT  STWVL  LGCVL  AALAA  YCLSV  GCVVI  VGHIE
T0036  .HPIT  KYIMA  CMSAD  LEVTT  STWVL  LGCVL  AALAA  YCLSV  GCVVI  VGHIE
T0026  .HPIA  KYLMA  CMSAD  LEVTT  STWVL  LGCVL  AALAA  YCLSV  GCVVI  VGHIE
T1787  .HPIT  KYVMA  CMSAD  LEVTT  STWVL  LGCVL  AALAA  YCLSV  GCVVI  VGHIE
       -----  -----  -----  -----  -----  -----  -----  -----  -----  -----
Cons   THPVT  KYIMA  CMSAD  LEVTT  STWVL  LGCVL  AALAA  YCLSV  GCVVI  VGHIE 1688                                                                      1737
         ▼                                                                         ▼
T0040  LGGKP  AIVPD  KEVAY  QQYDE  MEECS  QAAPY  IEQAQ  VIAHQ  FKEKV  LGLLQ
T0038  LGGKP  ALVPD  KEVAY  QQYDE  MEECS  QAAPY  IEQAQ  VIAHQ  FKEKV  LGLLQ
T0036  LGGKP  ALVPD  KEVAY  QQYDE  MEECS  QAAPY  IEQAQ  VIAHQ  FKEKV  LGLLQ
T0026  LGGKP  ALVPD  KEVAY  QQYDE  MEECS  QAAPY  IEQAQ  VIAHQ  FKEKV  LGLLQ
T1787  LGGKP  ALVPD  KEVAY  QQYDE  MEECS  QAAPY  IEQAQ  VIAHQ  FKEKV  LGLLQ
       -----  -----  -----  -----  -----  -----  -----  -----  -----  -----
Cons   LGGKP  ALVPD  KEVAY  QQYDE  MEECS  QAAPY  IEQAQ  VIAHQ  FKEKV  LGLLQ 1738                           1765
         ▼                              ▼
T0040  RATQQ  QAVIE  PIVAT  NWQKL  ETFWH  KHM
T0038  RATQQ  QAVIE  PIVAT  NWQKL  EAFWH  KHM
T0036  RATQQ  QAVIE  PIVAT  NWQ..  .....  ...
T0026  RATQQ  QAVIE  PIVAT  NWQ..  .....  ...
T1787  RATQQ  QAVIE  PIVAT  NWQKL  EAFWH  KHM
       -----  -----  -----  -----  -----  ---
Cons   RATQQ  QAVIE  PIVAT  NWQKL  EAFWH  KHM
```

FIG. 9C.

SEQUENCE COMPARISONS WITH TYPE 3

TYPE 3

| | |
|---|---|
| T0040 | CVVIVGHIELGCGKPALVPDKEVLYQQYDEAEECSQAAPYIEQAQVIAHQFKEKVLGLLQRATQQQAVIEPIVAINWQKLETFWHKHM... |
| T0038 | CVVIVGHIELGCGKPALVPDKEVLYQQYDEAEECSQAAPYIEQAQVIAHQFKEKVLGLLQRATQQQAVIEPIVAINWQKLEAFWHKHM... |
| T0036 | CVVIVGHIELGCGKPALVPDKEVLYQQYDEAEECSQAAPYIEQAQVIAHQFKEKVLGLLQRATQQQAVIEPIVAINW............ |
| T0026 | CVVIVGHIELGCGKPALVPDKEVLYQQYDEAEECSQAAPYIEQAQVIAHQFKEKVLGLLQRATQQQAVIEPIVAINWQ........... |
| T1787 | CVVIVGHIELGCGKPALVPDKEVLYQQYDEAEECSQAAPYIEQAQVIAHQFKEKVLGLLQRATQQQAVIEPIVAINWQKLEAFWHKHM... |

TYPE 2

| | |
|---|---|
| T0351 | ...IL.L.IMQRAVIAPDKEVLYEAFDEMEECASRAALIEEGQRIAEDLRSKIQGLLEQQASKAALIEPAVQASWPKYEQFW...... |
| T0059 | CISIGRLHLNDRYVVTPDKEILYEAFDEMEECASKAALIEEGQRMAEMLKSKIQGLLEQQATRQAADIQPYVQSSWPKLEQFWAKHM... |
| T0940 | CVSIGRLHL..RVV...DK...YE.........AALIEEGQRMAEMLKSKIQGLLEQQATRQAADIQPYVQSSWPKLEQFW....... |
| T0810 | CISIGRLHLNDRYVVAPDKEILYEAFDEMEECASKAALIEEGQRMAEMLKSKIQGLLEQQATRQAADIQPAVQSSWPKLEQFW..... |

TYPE 1

| | |
|---|---|
| T0016 | CVVIVGRIWLSGKPAIIPDRE..........PY..........QTNWQRLETF..... |
| T0042 | CVVIVGRIWLSGKPAIIPDREVLYREFDEMEECSQHLPYIEQGMNLAEQFKQKVALGLLQTASRQAEVIAP..QTNWQRLEAF..... |
| T0077 | CVVIVGRIWLSGKPAIIPDREVLYREFDEMEECSQHLPYIEQGMNLAEQFKQKVALGLLQTASRQAEVIAPAVQTNWQRLEAFW..... |
| T1801 | CVVIVGRIWLSGKPAYIPDREVLYREFDEMEECSQNLPYIEQGMNALAEQFKQKVALGLLQTASRQAEVIAPAVQTNWQKLEAFWAK.. |
| T1825 | CVVIVGRIDLSGKPAVIPDREVLYREFDEMEECSQHLPYIEQGMNALAEQFKQKVALGLLQTASRQAEVITPYVQTNWQKLEAFWAKFHM.. |

FIG. 10A.

DERIVATION OF PEPTIDE SEQUENCES

TYPE 3

```
T0040  CVVIVGHIELGCKPALVPDKEVLYQQYDEMEECSQAAPYIEQAQVIAHQFKEKVLGLLQRATQQQAVIEPIVATNWQKLETFWHKHM
T0038  CVVIVGHIELGCKPALVPDKEVLYQQYDEMEECSQAAPYIEQAQVIAHQFKEKVLGLLQRATQQQAVIEPIVATNWQKLEAFWHKHM
T0036  CVVIVGHIELGCKPALVPDKEVLYQQYDEMEECSQAAPYIEQAQVIAHQFKEKVLGLLQRATQQQAVIEPIVATNW......
T0026  CVVIVGHIELGCKPALVPDKEVLYQQYDEMEECSQAAPYIEQAQVIAHQFKEKVLGLLQRATQQQAVIEPIVATNWQ.
T1787  CVVIVGHIELGCKPALVPDKEVLYQQYDEMEECSQAAPYIEQAQVIAHQFKEKVLGLLQRATQQQAVIEPIVATNWQKLEAFWHKHM
Peptd  CVVIVGHIELGCKPALVPDKEVLYQQYDEMEECSQAAPYIEQAQVIAHQFKEKVLGLLQRATQQQAVIEPIVATNWQKLEAFWHKHM
```

TYPE 2

```
T0351  ........INQRAVIAPQKEVLYEAFDEMEECASRAALIEEGQRIAEMLRSKIQGLLQQASKQAQDIQPAVQASWPKYEQFW......
T0059  CISIIGRLHLNDRWYTPDKEILYEAFDEMEECASKAALIEEGQRMAEMLKSKIQGLLQQATRQAQDIQPAVQSSWPKLEQFWAKHMW
T0940  CISIIGRLH..RVV..DK...YE..........AALIEEGQRMAEMLKSKIQGLLQQATRQAQDIQPVVQSSWPKLEQFW.......
T0810  CISIIGRLHLNDRVVVAPDKEILYEAFDEMEECASKAALIEEGQRMAEMLKSKIQGLLQQATRQAQDIQPAVQSSWPKLEQFW....
Peptd  CISIIGRLHLNDRVVVAPDKEILYEAFDEMEECASKAALIEEGQRMAEMLKSKIQGLLQQATRQAQDIQPAVQSSWPKLEQFWAKHMW
```

TYPE 1

```
T0016  CVVIVGRIVLSGKPAIIPDRE..........PYIEQQMALAEQFKQKALGLLQTASRQAEVIAPAQTNWQRLETT......
T0042  CVVIVGRIVLSGKPAIIPDRENLYREFDEMECSQHLPYIEQQMALAEQFKQKALGLLQTASRQAEVIAPAQTNWQRLEAF
T0077  CVVIVGRIVLSGKPAIIPDRENLYREFDEMECSQHLPYIEQQMALAEQFKQKALGLLQTASRQAEVIAPAVQTNWQRLEAFW......
T1801  CVVIVGRIVLSGKPAVIPDRENLYREFDEMECSQHLPYIEQQMALAEQFKQKALGLLQTASRQAEVIAPAVQTNWQKLEAFWAK....
T1825  CVVIVGRIDLSGKPAVIPDRENLYREFDEMECSQHLPYIEQMALAEQFKQKALGLLQTASRQAEVITPVVQTNWQRLEAFWAKHM...
Peptd  CVVIVGRIDLSGKPAVIPDRENLYREFDEMECSQHLPYIEQMALAEQFKQKALGLLQTASRQAEVITPVVQTNWQRLEAFWAKHMWNF
```

FIG. 10B.

TYPE 3

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

| | |
|---|---|
| P1 | CVVIVGHIE |
| P2 | VVIVGHIEL |
| P3 | VIVGHIELG |
| P4 | IVGHIELGG |
| P5 | VGHIELGGK |
| P6 | GHIELGGKP |
| P7 | HIELGGKPA |
| P8 | IELGGKPAL |
| P9 | ELGGKPALV |
| P10 | LGGKPALVP |

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

| | |
|---|---|
| P11 | GGKPALVPD |
| P12 | GKPALVPDK |
| P13 | KPALVPDKE |
| P14 | PALVPDKEV |
| P15 | ALVPDKEVL |
| P16 | LVPDKEVLY |
| P17 | VPDKEVLYQ |
| P18 | PDKEVLYQQ |
| P19 | DKEVLYQQY |
| P20 | KEVLYQQYD |

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

| | |
|---|---|
| P21 | EVLYQQYDE |
| P22 | VLYQQYDEM |
| P23 | LYQQYDEME |
| P24 | YQQYDEMEE |
| P25 | QQYDEMEEC |
| P26 | QYDEMEECS |
| P27 | YDEMEECSQ |
| P28 | DEMEECSQA |
| P29 | EMEECSQAA |
| P30 | MEECSQAAP |

HCV-3  CVVIVGHIELGGKPALVPDKEVLYQQYDEMEECSQAAPYIEQAQVIAHQFKEKVLGLLQRATQQQAVIEPIVATNWQKLEAFWAKHMWNF

| | |
|---|---|
| P31 | EECSQAAPY |
| P32 | ECSQAAPYI |
| P33 | CSQAAPYIE |
| P34 | SQAAPYIEQ |
| P35 | QAAPYIEQA |
| P36 | AAPYIEQAQ |
| P37 | APYIEQAQV |
| P38 | PYIEQAQVI |
| P39 | YIEQAQVIA |
| P40 | IEQAQVIAH |

FIG. 11A.

HCV-3   CVVIVGHIELGGKPALVPDKEVLYQQYDEMEECSQAAPYIEQAQVIAHQFKEKVLGLLQRATQQQAVIEPIVATNWQKLEAFWAKHMWNF

P41                             EQAQVIAHQ
P42                              QAQVIAHQF
P43                               AQVIAHQFK
P44                                QVIAHQFKE
P45                                 VIAHQFKEK
P46                                  IAHQFKEKV
P47                                   AHQFKEKVL
P48                                    HQFKEKVLG
P49                                     QFKEKVLGL
P50                                      FKEKVLGLL

HCV-3   CVVIVGHIELGGKPALVPDKEVLYQQYDEMEECSQAAPYIEQAQVIAHQFKEKVLGLLQRATQQQAVIEPIVATNWQKLEAFWAKHMWNF

P51                                       KEKVLGLLQ
P52                                        EKVLGLLQR
P53                                         KVLGLLQRA
P54                                          VLGLLQRAT
P55                                           LGLLQRATQ
P56                                            GLLQRATQQ
P57                                             LLQRATQQQ
P58                                              LQRATQQQA
P59                                               QRATQQQAV
P60                                                RATQQQAVI

HCV-3   CVVIVGHIELGGKPALVPDKEVLYQQYDEMEECSQAAPYIEQAQVIAHQFKEKVLGLLQRATQQQAVIEPIVATNWQKLEAFWAKHMWNF

P61                                                 ATQQQAVIE
P62                                                  TQQQAVIEP
P63                                                   QQQAVIEPI
P64                                                    QQAVIEPIV
P65                                                     QAVIEPIVA
P66                                                      AVIEPIVAT
P67                                                       VIEPIVATN
P68                                                        IEPIVATNW
P69                                                         EPIVATNWQ
P70                                                          PIVATNWQK

HCV-3   CVVIVGHIELGGKPALVPDKEVLYQQYDEMEECSQAAPYIEQAQVIAHQFKEKVLGLLQRATQQQAVIEPIVATNWQKLEAFWAKHMWNF

P71                                                           IVATNWQKL
P72                                                            VATNWQKLE
P73                                                             ATNWQKLEA
P74                                                              TNWQKLEAF
P75                                                               NWQKLEAFW
P76                                                                WQKLEAFWA
P77                                                                 QKLEAFWAK
P78                                                                  KLEAFWAKH
P79                                                                   LEAFWAKHM
P80                                                                    EAFWAKHMW

HCV-3   CVVIVGHIELGGKPALVPDKEVLYQQYDEMEECSQAAPYIEQAQVIAHQFKEKVLGLLQRATQQQAVIEPIVATNWQKLEAFWAKHMWNF

P81                                                                     AFWAKHMWN
P82                                                                      FWAKHMWNF

FIG. 11B.

TYPE 2

HCV-2  CISIIGRLHLNDRVVVTPDKEILYEAFDEMEECASKAALIEEGQRMAEMLKSKIQGLLQQATRQAQDIQPVVQSSWPKLEQFWAKHMWNF

```
P 1    CISIIGRLH
P 2     ISIIGRLHL
P 3      SIIGRLHLN
P 4       IIGRLHLND
P 5        IGRLHLNDR
P 6         GRLHLNDRV
P 7          RLHLNDRVV
P 8           LHLNDRVVV
P 9            HLNDRVVVT
P 10            LNDRVVVTP
```

HCV-2  CISIIGRLHLNDRVVVTPDKEILYEAFDEMEECASKAALIEEGQRMAEMLKSKIQGLLQQATRQAQDIQPVVQSSWPKLEQFWAKHMWNF

```
P 11             NDRVVVTPD
P 22              DRVVVTPDK
P 33               RVVVTPDKE
P 44                VVVTPDKEI
P 55                 VVTPDKEIL
P 66                  VTPDKEILY
P 77                   TPDKEILYE
P 88                    PDKEILYEA
P 99                     DKEILYEAF
P 20                      KEILYEAFD
```

HCV

```
HCV-2  CISIIGRLHLNDRVVVTPDKEILYEAFDEMEECASKAALIEEGQRMAEMLKSKIQGLLQQATRQAQDIQPVVQSSWPKLEQFWAKHMWNF
P41                                          EEGQRMAEM
P42                                           EGQRMAEML
P43                                            GQRMAEMLK
P44                                             QRMAEMLKS
P45                                              RMAEMLKSK
P46                                               MAEMLKSKI
P47                                                AEMLKSKIQ
P48                                                 EMLKSKIQG
P49                                                  MLKSKIQGL
P50                                                   LKSKIQGLL

HCV-2  CISIIGRLHLNDRVVVTPDKEILYEAFDEMEECASKAALIEEGQRMAEMLKSKIQGLLQQATRQAQDIQPVVQSSWPKLEQFWAKHMWNF
P51                                                    KSKIQGLLQ
P52                                                     SKIQGLLQQ
P53                                                      KIQGLLQQA
P54                                                       IQGLLQQAT
P55                                                        QGLLQQATR
P56                                                         GLLQQATRQ
P57                                                          LLQQATRQA
P58                                                           LQQATRQAQ
P59                                                            QQATRQAQD
P60                                                             QATRQAQDI

HCV-2  CISIIGRLHLNDRVVVTPDKEILYEAFDEMEECASKAALIEEGQRMAEMLKSKIQGLLQQATRQAQDIQPVVQSSWPKLEQFWAKHMWNF
P61                                                              ATRQAQDIQ
P62                                                               TRQAQDIQP
P63                                                                RQAQDIQPV
P64                                                                 QAQDIQPVV
P65                                                                  AQDIQPVVQ
P66                                                                   QDIQPVVQS
P67                                                                    DIQPVVQSS
P68                                                                     IQPVVQSSW
P69                                                                      QPVVQSSWP
P70                                                                       PVVQSSWPK

HCV-2  CISIIGRLHLNDRVVVTPDKEILYEAFDEMEECASKAALIEEGQRMAEMLKSKIQGLLQQATRQAQDIQPVVQSSWPKLEQFWAKHMWNF
P71                                                                         VVQSSWPKL
P72                                                                          VQSSWPKLE
P73                                                                           QSSWPKLEQ
P74                                                                            SSWPKLEQF
P75                                                                             SWPKLEQFW
P76                                                                              WPKLEQFWA
P77                                                                               PKLEQFWAK
P78                                                                                KLEQFWAKH
P79                                                                                 LEQFWAKHM
P80                                                                                  EQFWAKHMW

HCV-2  CISIIGRLHLNDRVVVTPDKEILYEAFDEMEECASKAALIEEGQRMAEMLKSKIQGLLQQATRQAQDIQPVVQSSWPKLEQFWAKHMWNF
P81                                                                                   QFWAKHMWN
P82                                                                                    FWAKHMWNF
```

FIG. 11D.

TYPE 1

HCV-1 CVVIVGRIVLSGKPAIIPDREVLYREFDEMEECSQHLPYIEQGMMLAEQFKQKALGLLQTASRQAEVIAPAVQTNWQRLEAFWAKHMWNF

```
P 1    CVVIVGRIV
P 2     VVIVGRIVL
P 3      VIVGRIVLS
P 4       IVGRIVLSG
P 5        VGRIVLSGK
P 6         GRIVLSGKP
P 7          RIVLSGKPA
P 8           IVLSGKPAI
P 9            VLSGKPAII
P 10            LSGKPAIIP
```

HCV-1 CVVIVGRIVLSGKPAIIPDREVLYREFDEMEECSQHLPYIEQGMMLAEQFKQKALGLLQTASRQAEVIAPAVQTNWQRLEAFWAKHMWNF

```
P 11             SGKPAIIPD
P 12              GKPAIIPDR
P 13               KPAIIPDRE
P 14                PAIIPDREV
P 15                 AIIPDREVL
P 16                  IIPDREVLY
P 17                   IPDREVLYR
P 18                    PDREVLYRE
P 19                     DREVLYREF
P 20                      REVLYREFD
```

HCV-1 CVVIVGRIVLSGKPAIIPDREVLYREFDEMEECSQHLPYIEQGMMLAEQFKQKALGLLQTASRQAEVIAPAVQTNWQRLEAFWAKHMWNF

```
P 21                       EVLYREFDE
P 22                        VLYREFDEM
P 23                         LYREFDEME
P 24                          YREFDEMEE
P 25                           REFDEMEEC
P 26                            EFDEMEECS
P 27                             FDEMEECSQ
P 28                              DEMEECSQH
P 29                               EMEECSQHL
P 30                                MEECSQHLP
```

HCV-1 CVVIVGRIVLSGKPAIIPDREVLYREFDEMEECSQHLPYIEQGMMLAEQFKQKALGLLQTASRQAEVIAPAVQTNWQRLEAFWAKHMWNF

```
P 31                                 EECSQHLPY
P 32                                  ECSQHLPYI
P 33                                   CSQHLPYIE
P 34                                    SQHLPYIEQ
P 35                                     QHLPYIEQG
P 36                                      HLPYIEQGM
P 37                                       LPYIEQGMM
P 38                                        PYIEQGMML
P 39                                         YIEQGMMLA
P 40                                          IEQGMMLAE
```

FIG. 11E.

HCV-1  CVVIVGRIVLSGKPAIIPDREVLYREFDEMEECSQHLPYIEQGMMLAEQFKQKALGLLQTASRQAEVIAPAVQTNWQRLEAFWAKHMWNF

```
P41                             EQGMMLAEQ
P42                              QGMMLAEQF
P43                               GMMLAEQFK
P44                                MMLAEQFKQ
P45                                 MLAEQFKQK
P46                                  LAEQFKQKA
P47                                   AEQFKQKAL
P48                                    EQFKQKALG
P49                                     QFKQKALGL
P50                                      FKQKALGLL
```

HCV-1  CVVIVGRIVLSGKPAIIPDREVLYREFDEMEECSQHLPYIEQGMMLAEQFKQKALGLLQTASRQAEVIAPAVQTNWQRLEAFWAKHMWNF

```
P51                                       KQKALGLLQ
P52                                        QKALGLLQT
P53                                         KALGLLQTA
P54                                          ALGLLQTAS
P55                                           LGLLQTASR
P56                                            GLLQTASRQ
P57                                             LLQTASRQA
P58                                              LQTASRQAE
P59                                               QTASRQAEV
P60                                                TASRQAEVI
```

HCV-1  CVVIVGRIVLSGKPAIIPDREVLYREFDEMEECSQHLPYIEQGMMLAEQFKQKALGLLQTASRQAEVIAPAVQTNWQRLEAFWAKHMWNF

```
P61                                                 ASRQAEVIA
P62                                                  SRQAEVIAP
P63                                                   RQAEVIAPA
P64                                                    QAEVIAPAV
P65                                                     AEVIAPAVQ
P66                                                      EVIAPAVQT
P67                                                       VIAPAVQTN
P68                                                        IAPAVQTNW
P69                                                         APAVQTNWQ
P70                                                          PAVQTNWQR
```

HCV-1  CVVIVGRIVLSGKPAIIPDREVLYREFDEMEECSQHLPYIEQGMMLAEQFKQKALGLLQTASRQAEVIAPAVQTNWQRLEAFWAKHMWNF

```
P71                                                           AVQTNWQRL
P72                                                            VQTNWQRLE
P73                                                             QTNWQRLEA
P74                                                              TNWQRLEAF
P75                                                               NWQRLEAFW
P76                                                                WQRLEAFWA
P77                                                                 QRLEAFWAK
P78                                                                  RLEAFWAKH
P79                                                                   LEAFWAKHM
P80                                                                    EAFWAKHMW
```

HCV-1  CVVIVGRIVLSGKPAIIPDREVLYREFDEMEECSQHLPYIEQGMMLAEQFKQKALGLLQTASRQAEVIAPAVQTNWQRLEAFWAKHMWNF

```
P81                                                                     AFWAKHMWN
P82                                                                      FWAKHMWNF
```

FROM FIG. 15A.

| | | 183 | 203 | 223 | 243 | 262 |
|---|---|---|---|---|---|---|
| | | GCCTATCCCC AAAGCTCGTC | GGCCCGAGGG CAGGACCTGG | GCTCAGCCCG GGTACCCTTG | GCCCCTCTAT GGCAATGAGG | |
| 1a | HCV-1 | .......... .......... | .......... .......... | .......... .......... | .......... .......... | |
| 1b | HCV-J | A......... .........C | .......... T......... | .......... .......... | .......... .........C | |
| 2a | HC-J6 | ..C......T ....A...G. | .CT..ACT.. ..AAT..... | .GAA...A.. .A....C... | ...A.T..C. .....G.C.. | |
| 2b | HC-J8 | ..C......G ....A...G. | .CT..ACC.. ..A.T..... | .GAA...A.. .A....T... | ...A.C..C. .....A.C.. | |
| 3a | Eb-29 | .......... ......G... | .AG...A... ...T...... | .......... ......G... | ......T..C ......T.C. | |
| | Eg-29(1) | A......... .G.G..G... | .AT....... .A..T..... | .A.A...A.. .A..T.A... | ...T...C.. ...T...... | |
| | Eg-33(2) | A......... .G.G..G... | .AT....... .A..T..... | ..A....A.. .A..T.A... | ...T...C.. ...T...... | |
| | Eg-21(3) | .......... .G.G..G... | .AT....... .A..T..... | ..A....A.. .A.TT.A... | ...TT...C. ...A.A---- | |

| | | 5 | 25 | 45 | 65 | 85 |
|---|---|---|---|---|---|---|
| | | PKPQKKNKRN TNRRPQDVKF | PGGGQIVGGV YLLPRRGPRL | GVRATRKTSE RSQPRGRRQP | IPKARRPEGR TWAQPGYPWP | LYGNE |
| 1a | HCV-1 | .......... .......... | .......... .......... | .......... .......... | .......... .......... | ..... |
| 1b | HCV-J | .......... .......... | .......... .......... | .......... .......... | .......... .......... | ..... |
| 2a | HC-J6 | ...R.T.... .......... | .......... .......... | .......... .......... | ...D.ST.K. S.GK...... | ..... |
| 2b | HC-J8 | ...R.T.... .......... | .......... .......... | .......... .......... | ...D.ST.K. S.GK...... | ..... |
| 3a | Eb-1 | A..R.T.... ...I...... | .......... ...V...... | .......... .......... | ......S... S......... | ..... |
| | Eg-29,33 | .R........ ..M....... | .......... .......... | ..C....... .......... | ......S... S......... | ..... |
| | Eg-21 | .......... ..T....... | .......... .......... | ....G..... .......... | ......S... S......... | ....F |

FIG. 15B.

SEQUENCE LISTING (1) GENERAL INFORMATION:

(iii) NUMBER OF SEQUENCES: 53

(2) INFORMATION FOR SEQ ID NO: 1:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Hepatitis-C virus (xi) SEQUENCE DESCRIPTION: SEQ ID NO: 1:

Lys Pro Ala Leu Val Pro Asp Lys Glu Val Leu Tyr Gln Gln Tyr Asp
1               5                   10                  15

Glu Met (2) INFORMATION FOR SEQ ID NO: 2:

```
    (i) SEQUENCE CHARACTERISTICS:
        (A) LENGTH: 19 amino acids
        (B) TYPE: amino acid
        (C) STRANDEDNESS: <Unknown>
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Hepatitis-C virus (xi) SEQUENCE DESCRIPTION: SEQ ID NO: 2:

Glu Cys Ser Gln Ala Ala Pro Tyr Ile Glu Gln Ala Gln Val Ile Ala
1               5                   10                  15

His Gln Phe (2) INFORMATION FOR SEQ ID NO: 3:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Hepatitis-C virus (xi) SEQUENCE DESCRIPTION: SEQ ID NO: 3:

Arg Val Val Val Thr Pro Asp Lys Glu Ile Leu Tyr Glu Ala Phe Asp
1               5                   10                  15

Glu Met (2) INFORMATION FOR SEQ ID NO: 4:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Hepatitis-C virus (xi) SEQUENCE DESCRIPTION: SEQ ID NO: 4:

Arg Ala Val Ile Ala Pro Asp Lys Glu Val Leu Tyr Glu Ala Phe Asp
1               5                   10                  15

Glu Met (2) INFORMATION FOR SEQ ID NO: 5:

(i) SEQUENCE CHARACTERISTICS:
        (A) LENGTH: 19 amino acids
        (B) TYPE: amino acid
        (C) STRANDEDNESS: <Unknown>
        (D) TOPOLOGY: linear
```

```
        (ii) MOLECULE TYPE: peptide (iii) HYPOTHETICAL: NO (v) FRAGMENT TYPE: internal (vi) ORIGINAL SOURCE:
             (A) ORGANISM: Hepatitis-C virus (xi) SEQUENCE DESCRIPTION: SEQ ID NO: 5:

Glu Cys Ala Ser Lys Ala Ala Leu Ile Glu Glu Gly Gln Arg Met Ala
1               5                   10                  15

Glu Met Leu (2) INFORMATION FOR SEQ ID NO: 6:

(i) SEQUENCE CHARACTERISTICS:
            (A) LENGTH: 19 amino acids
            (B) TYPE: amino acid
            (C) STRANDEDNESS: <Unknown>
            (D) TOPOLOGY: linear (ii) MOLECULE TYPE: peptide (iii) HYPOTHETICAL: NO (v) FRAGMENT TYPE: internal (vi) ORIGINAL SOURCE:
             (A) ORGANISM: Hepatitis-C virus (xi) SEQUENCE DESCRIPTION: SEQ ID NO: 6:

Glu Cys Ala Ser Arg Ala Ala Leu Ile Glu Glu Gly Gln Arg Ile Ala
1               5                   10                  15

Glu Met Leu (2) INFORMATION FOR SEQ ID NO: 7:

(i) SEQUENCE CHARACTERISTICS:
            (A) LENGTH: 18 amino acids
            (B) TYPE: amino acid
            (C) STRANDEDNESS: <Unknown>
            (D) TOPOLOGY: linear (ii) MOLECULE TYPE: peptide (iii) HYPOTHETICAL: NO (v) FRAGMENT TYPE: internal (vi) ORIGINAL SOURCE:
             (A) ORGANISM: Hepatitis-C virus (xi) SEQUENCE DESCRIPTION: SEQ ID NO: 7:

Lys Pro Ala Ile Ile Pro Asp Arg Glu Val Leu Tyr Arg Glu Phe Asp
1               5                   10                  15

Glu Met (2) INFORMATION FOR SEQ ID NO: 8:

(i) SEQUENCE CHARACTERISTICS:
            (A) LENGTH: 18 amino acids
            (B) TYPE: amino-acid
            (C) STRANDEDNESS: <Unknown>
            (D) TOPOLOGY: linear (ii) MOLECULE TYPE: peptide (iii) HYPOTHETICAL: NO
```

```
        (v) FRAGMENT TYPE: internal (vi) ORIGINAL SOURCE:
             (A) ORGANISM: Hepatitis-C virus (xi) SEQUENCE DESCRIPTION: SEQ ID NO: 8:

Lys Pro Ala Val Ile Pro Asp Arg Glu Val Leu Tyr Arg Glu Phe Asp
1               5                   10                  15

Glu Met (2) INFORMATION FOR SEQ ID NO: 9:

(i) SEQUENCE CHARACTERISTICS:
             (A) LENGTH: 18 amino acids
             (B) TYPE: amino acid
             (C) STRANDEDNESS: <Unknown>
             (D) TOPOLOGY: linear (ii) MOLECULE TYPE: peptide (iii) HYPOTHETICAL: NO (v) FRAGMENT TYPE: internal (vi) ORIGINAL SOURCE:
             (A) ORGANISM: Hepatitis-C virus (xi) SEQUENCE DESCRIPTION: SEQ ID NO: 9:

Arg Pro Ala Val Xaa Pro Asp Arg Glu Val Leu Tyr Gln Glu Phe Asp
1               5                   10                  15

Glu Met (2) INFORMATION FOR SEQ ID NO: 10:

(i) SEQUENCE CHARACTERISTICS:
             (A) LENGTH: 17 amino acids
             (B) TYPE: amino acid
             (C) STRANDEDNESS: <Unknown>
             (D) TOPOLOGY: linear (ii) MOLECULE TYPE: peptide (iii) HYPOTHETICAL: NO (v) FRAGMENT TYPE: internal (vi) ORIGINAL SOURCE:
             (A) ORGANISM: Hepatitis-C virus (xi) SEQUENCE DESCRIPTION: SEQ ID NO: 10:

Glu Cys Ser Gln His Leu Pro Tyr Ile Glu Gly Met Leu Ala Glu Gln
1               5                   10                  10

Phe (2) INFORMATION FOR SEQ ID NO: 11:

(i) SEQUENCE CHARACTERISTICS:
             (A) LENGTH: 17 amino acids
             (B) TYPE: amino acid
             (C) STRANDEDNESS: <Unknown>
             (D) TOPOLOGY: linear (ii) MOLECULE TYPE: peptide (iii) HYPOTHETICAL: NO (v) FRAGMENT TYPE: internal (vi) ORIGINAL SOURCE:
             (A) ORGANISM: Hepatitis-C virus
```

(xi) SEQUENCE DESCRIPTION: SEQ ID NO: 11:

Glu Cys Ser Gln His Leu Pro Tyr Ile Glu Gly Ala Leu Ala Glu Gln
1               5                   10                  10

Phe (2) INFORMATION FOR SEQ ID NO: 12:

(i) SEQUENCE CHARACTERISTICS:
            (A) LENGTH: 194 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 12:

NNNNNNNNNN CGAGTGTCGT GCAGCCTCCA GGMCYCCCCC TCCCGGGAGA GCCATAGTGG      60

TCTGCGGAAC CGGTGAGTAC ACCGGAATCG CTGGGGTGAC CGGGTCCTTT CTTGGARCAA     120

CCCGCTCAAT ACCCAGAAAT TTGGGCGTGC CCCCGCRAGA YCACTAGCCG AGTAGTGTTG    180

GGTCGCGAAA GGCC                                                      194

(2) INFORMATION FOR SEQ ID NO: 13:

(i) SEQUENCE CHARACTERISTICS:
            (A) LENGTH: 85 amino acids
            (B) TYPE: amino acid
            (C) STRANDEDNESS: <Unknown>
            (D) TOPOLOGY: linear (ii) MOLECULE TYPE: peptide (iii) HYPOTHETICAL: yes (v) FRAGMENT TYPE: internal (vi) ORIGINAL SOURCE:
            (A) ORGANISM: Hepatitis-C virus (xi) SEQUENCE DESCRIPTION: SEQ ID NO: 13:

Xaa Xaa Xaa Xaa Xaa Xaa Xaa Xaa Xaa Xaa Glu Ile Tyr Gln Cys Cys
1               5                   10                  15

Asn Leu Glu Pro Glu Ala Arg Lys Val Ile Ser Ser Leu Thr Glu Arg
                20                  25                  30

Leu Tyr Cys Gly Gly Pro Met Phe Asn Ser Lys Gly Ala Gln Cys Gly
            35                  40                  45

Tyr Arg Arg Cys Arg Ala Ser Gly Val Leu Pro Thr Ser Phe Gly Asn
        50                  55                  60

Thr Ile Thr Cys Tyr Ile Lys Ala Thr Ala Ala Cys Xaa Ala Ala Gly
65                  70                  75                  80

Leu Arg Asn Pro Asp
                85

(2) INFORMATION FOR SEQ ID NO: 14:

(i) SEQUENCE CHARACTERISTICS:
            (A) LENGTH: 57 amino acids
            (B) TYPE: amino acid
            (C) STRANDEDNESS: <Unknown>

```
            (D) TOPOLOGY: linear (ii) MOLECULE TYPE: peptide (iii) HYPOTHETICAL: yes (v) FRAGMENT TYPE: internal (vi) ORIGINAL SOURCE:
             (A) ORGANISM: Hepatitis-C virus (xi) SEQUENCE DESCRIPTION: SEQ ID NO: 14:

Lys Gln Gln Gly Leu Asn Phe Ser Tyr Leu Xaa Ala Tyr Gln Ala Thr
1               5                  10                  15

Val Cys Ala Arg Ala Gln Ala Xaa Pro Pro Ser Trp Asp Glu Xaa Trp
                20                  25                  30

Lys Cys Leu Val Arg Leu Lys Pro Thr Leu His Gly Pro Thr Pro Leu
                35                  40                  45

Leu Tyr Arg Leu Gly Pro Val Gln Asn
            50                  55

(2) INFORMATION FOR SEQ ID NO: 15:

(i) SEQUENCE CHARACTERISTICS:
             (A) LENGTH: 124 amino acids
             (B) TYPE: amino acid
             (C) STRANDEDNESS: <Unknown>
             (D) TOPOLOGY: linear (ii) MOLECULE TYPE: peptide (iii) HYPOTHETICAL: yes (v) FRAGMENT TYPE: internal (vi) ORIGINAL SOURCE:
             (A) ORGANISM: Hepatitis-C virus (xi) SEQUENCE DESCRIPTION: SEQ ID NO: 15:

Ala Lys Pro Gln Arg Lys Thr Lys Arg Asn Thr Ile Arg Arg Pro Gln
1               5                  10                  15

Asp Val Lys Phe Pro Gly Gly Gly Gln Ile Val Gly Gly Val Tyr Val
                20                  25                  30

Leu Pro Arg Arg Gly Pro Arg Leu Gly Val Cys Ala Thr Arg Lys Thr
                35                  40                  45

Ser Glu Arg Ser Gln Pro Arg Gly Arg Gln Pro Ile Pro Lys Ala
            50                  55                  60

Arg Arg Ser Glu Gly Arg Ser Trp Ala Gln Pro Gly Tyr Pro Trp Pro
65                  70                  75                  80

Leu Tyr Gly Asn Glu Gly Cys Gly Trp Ala Gly Trp Leu Leu Ser Pro
                85                  90                  95

Arg Gly Ser Arg Pro Ser Trp Gly Pro Asn Asp Pro Arg Arg Arg Ser
                100                 105                 110

Arg Asn Leu Gly Lys Val Ile Asp Thr Leu Thr Trp
                115                 120

(2) INFORMATION FOR SEQ ID NO: 16:

(i) SEQUENCE CHARACTERISTICS:
             (A) LENGTH: 367 base pairs
             (B) TYPE: nucleic acid
             (C) STRANDEDNESS: double
             (D) TOPOLOGY: linear (ii) MOLECULE TYPE: cDNA
```

(iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO: 16:

```
NNNNCACCCY RUCRCRAAAU ACVUCAUGGC AUGYAUGUCA GCUGAUCUGG AAGUAACCAC    60

CAGCACCUGG GUGUUGCUUG GAGGRGUCCU CGCKGCCCUA GCGGCCUACU GCUUGUCAGU   120

CGGCUGCGUU GUGAUUGUGG GYCAUAUUGA GCUGG (iv) ANTI-SENSE: NO (vi) ORIGINAL SOURCE:
            (A) ORGANISM: Hepatitis-C virus (xi) SEQUENCE DESCRIPTION: SEQ ID NO: 18:

TGAGTGTYGT RCAGCCTCCA GGAYYCCCCC NNNNNNNNNN NNNNNNNNNN NNNNNNNNNN        60

CGGTGAGTWC ACCGGAATCG CCGGGAYGAC CGGGTCCTTT CTTGGANNHW ACCCGCTCMA       120

TGCCCGGAAA TNNNNNNNNN NNNNNGCRAG ACYGCTAGCC GAGTAGTGTT GGGTCGC         177

(2) INFORMATION FOR SEQ ID NO: 19:

(i) SEQUENCE CHARACTERISTICS:
            (A) LENGTH: 240 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 19:

AAACCAAAAG AAACACCATC CGTCGCCCAC AGGACGTCAA GTTCCCGGGT GGCGGACAGA        60

TCGTTGGTGG AGTATACGTG TTGCCGCGCA GGGGCCCACG ATTGGGTGTG TGCGCGACGC       120

GTAAAACTTC TGAACGGTCA CAGCCTCGCG GACGACGACA GCCTATCCCC AAAGCGCGTC       180

GGAGCGAAGG CAGGTCCTGG GCTCAGCCCG GGTACCCGTG GCCCCTCTAT GGTAACGAGG       240

(2) INFORMATION FOR SEQ ID NO: 20:

(i) SEQUENCE CHARACTERISTICS:
            (A) LENGTH: 240 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 20:

NNNNNNNNNN TAACACCAAC CGCCGCCCCA YGGACGTTAA GTTCCCGGGT GGTGGYCAGA        60

TCGTTGGCGG AGTTTACTTG TTGCCGCGCA GGGGCCCYMG KTTGGGTGTG CGCGCGACTS      120

GRAAGACTTC GGAGCGGTCG CAACCTCGTG GGAGACGYCA RCCTATCCCM AAGGCGCGTC      180

GATCCGAGGG AAGGTCCTGG GCACARCCAG GATWTCCATG NNNNNNNNNN NNNNNNNNNN     240

(2) INFORMATION FOR SEQ ID NO: 21:

(i) SEQUENCE CHARACTERISTICS:
            (A) LENGTH: 82 amino acids
            (B) TYPE: amino acid
            (C) STRANDEDNESS: <Unknown>
            (D) TOPOLOGY: linear (ii) MOLECULE TYPE: peptide (iii) HYPOTHETICAL: yes (v) FRAGMENT TYPE: internal (vi) ORIGINAL SOURCE:
                  (A) ORGANISM: Hepatitis-C virus (xi) SEQUENCE DESCRIPTION: SEQ ID NO: 21:

Xaa Xaa Xaa Xaa Lys Arg Asn Thr Asn Arg Arg Pro Xaa Asp Val Lys
1               5                   10                  15

Phe Pro Gly Gly Gly Gln Ile Val Gly Val Tyr Leu Leu Pro Arg
            20                  25                  30

Arg Gly Pro Arg Leu Gly Val Arg Ala Thr Xaa Lys Thr Ser Glu Arg
        35                  40                  45

Ser Gln Pro Arg Gly Arg Arg Gln Pro Ile Pro Lys Ala Arg Arg Ser
    50                  55                  60

Glu Gly Arg Ser Trp Ala Gln Pro Gly Xaa Pro Trp Pro Leu Tyr Xaa
65                  70                  75                  80

Xaa Xaa (2) INFORMATION FOR SEQ ID NO: 22:

(i) SEQUENCE CHARACTERISTICS:
                  (A) LENGTH: 29 base pairs
                  (B) TYPE: nucleic acid
                  (C) STRANDEDNESS: single
                  (D) TOPOLOGY: linear (ii) MOLECULE TYPE: other nucleic acid
                  (A) DESCRIPTION: /desc = "synthetic DNA (iii) HYPOTHETICAL: NO (iv) ANTI-SENSE: NO (vi) ORIGINAL SOURCE:
                  (A) ORGANISM: Hepatitis-C virus (xi) SEQUENCE DESCRIPTION: SEQ ID NO: 22:

ATACTCGAGG TGCACGGTCT ACGAGACCT                                          29

(2) INFORMATION FOR SEQ ID NO: 23:

(i) SEQUENCE CHARACTERISTICS:
                  (A) LENGTH: 26 base pairs
                  (B) TYPE: nucleic acid
                  (C) STRANDEDNESS: single
                  (D) TOPOLOGY: linear (ii) MOLECULE TYPE: other nucleic acid
                  (A) DESCRIPTION: /desc = "synthetic DNA (iii) HYPOTHETICAL: NO (iv) ANTI-SENSE: NO (vi) ORIGINAL SOURCE:
                  (A) ORGANISM: Hepatitis-C virus (xi) SEQUENCE DESCRIPTION: SEQ ID NO: 23:

CACTCTCGAG CACCCTATCA GGCAGT                                             26

(2) INFORMATION FOR SEQ ID NO: 24:

(i) SEQUENCE CHARACTERISTICS:
                  (A) LENGTH: 20 base pairs
                  (B) TYPE: nucleic acid
                  (C) STRANDEDNESS: single
                  (D) TOPOLOGY: linear (ii) MOLECULE TYPE: other nucleic acid
            (A) DESCRIPTION: /desc = "synthetic DNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 24:

CTGTGAGGAA CTACTGTCTT                                                     20

(2) INFORMATION FOR SEQ ID NO: 25:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 25:

TTCACGCAGA AAGCGTCTAG                                                     20

(2) INFORMATION FOR SEQ ID NO: 26:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 26:

ATGTACCCCA TGAGGTCGGC                                                     20

(2) INFORMATION FOR SEQ ID NO: 27:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 27:

AGGTCTCGTA GACCGTGCAT CATGAGCAC                                           29

(2) INFORMATION FOR SEQ ID NO: 28:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (iii) HYPOTHETICAL: NO (vi) ORIGINAL SOURCE:
        (A) ORGANISM: Hepatitis-C virus (xi) SEQUENCE DESCRIPTION: SEQ ID NO: 28:

CCGGCATGCA TGTCATGATG TAT                                                 23

(2) INFORMATION FOR SEQ ID NO: 29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO: 29:

GTATTTGGTG ACTGGGTGCG TC                                                  22

(2) INFORMATION FOR SEQ ID NO: 30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO: 30:

TCTTGAATTT TGGGAGGGCG TCTT                                                24

(2) INFORMATION FOR SEQ ID NO: 31:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "synthetic DNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 31:

CATATAGATG CCCACTTCCT ATC                                                23

(2) INFORMATION FOR SEQ ID NO: 32:

(i) SEQUENCE CHARACTERISTICS:
             (A) LENGTH: 32 base pairs
             (B) TYPE: nucleic acid
             (C) STRANDEDNESS: single
             (D) TOPOLOGY: linear (ii) MOLECULE TYPE: other nucleic acid
            (A) DESCRIPTION: /desc = "synthetic DNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 32:

AACTCGAGTA TCCCACTGAT GAAGTTCCAC AT                                       32

(2) INFORMATION FOR SEQ ID NO: 33:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
            (A) DESCRIPTION: /desc = "synthetic DNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 33:

CACATGTGCT TCGCCCAGAA                                                    20

(2) INFORMATION FOR SEQ ID NO: 34:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid
            (A) DESCRIPTION: /desc = "synthetic DNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 34:

```
GGACCTACGC CCCTTCTATA                                                    20

(2) INFORMATION FOR SEQ ID NO: 35:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic DNA (iii) HYPOTHETICAL: NO (iv) ANTI-SENSE: NO (vi) ORIGINAL SOURCE:
         (A) ORGANISM: Hepatitis-C virus (xi) SEQUENCE DESCRIPTION: SEQ ID NO: 35:

TCGGTTGGGG CCTGTCCAAA ATG                                                23

(2) INFORMATION FOR SEQ ID NO: 36:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic DNA (iii) HYPOTHETICAL: NO (iv) ANTI-SENSE: NO (vi) ORIGINAL SOURCE:
         (A) ORGANISM: Hepatitis-C virus (xi) SEQUENCE DESCRIPTION: SEQ ID NO: 36:

GGTCCCACCC CTCTCCTGTA                                                    20

(2) INFORMATION FOR SEQ ID NO: 37:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic DNA (iii) HYPOTHETICAL: NO (iv) ANTI-SENSE: NO (vi) ORIGINAL SOURCE:
         (A) ORGANISM: Hepatitis-C virus (xi) SEQUENCE DESCRIPTION: SEQ ID NO: 37:

CCGCTTGGGT TCCGTTACCA ACG                                                23

(2) INFORMATION FOR SEQ ID NO: 38:

(i) SEQUENCE CHARACTERISTICS:
         (A) LENGTH: 20 base pairs
         (B) TYPE: nucleic acid
         (C) STRANDEDNESS: single
         (D) TOPOLOGY: linear
```

```
    (ii) MOLECULE TYPE: other nucleic acid
         (A) DESCRIPTION: /desc = "synthetic DNA (iii) HYPOTHETICAL: NO (iv) ANTI-SENSE: NO (vi) ORIGINAL SOURCE:
         (A) ORGANISM: Hepatitis-C virus (xi) SEQUENCE DESCRIPTION: SEQ ID NO: 38:

GGGCCAACAC CCCTGCTATA                                              20

(2) INFORMATION FOR SEQ ID NO: 39:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic DNA (iii) HYPOTHETICAL: NO (iv) ANTI-SENSE: NO (vi) ORIGINAL SOURCE:
         (A) ORGANISM: Hepatitis-C virus (xi) SEQUENCE DESCRIPTION: SEQ ID NO: 39:

CAGACTGGGC GCCGTTCAGA ATG                                          23

(2) INFORMATION FOR SEQ ID NO: 40:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic DNA (iii) HYPOTHETICAL: NO (iv) ANTI-SENSE: NO (vi) ORIGINAL SOURCE:
         (A) ORGANISM: Hepatitis-C virus (xi) SEQUENCE DESCRIPTION: SEQ ID NO: 40:

GGCGGAATTC CTGGTCATAG CCTCCGTGAA                                   30

(2) INFORMATION FOR SEQ ID NO: 41:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "synthetic DNA (iii) HYPOTHETICAL: NO (iv) ANTI-SENSE: NO (vi) ORIGINAL SOURCE:
         (A) ORGANISM: Hepatitis-C virus
```

(xi) SEQUENCE DESCRIPTION: SEQ ID NO: 41:

CCACGACTAG ATCATCTCCG                                              20

(2) INFORMATION FOR SEQ ID NO: 42:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO: 42:

TGGGGATCCC GTATGATACC CGCTGCTTTG A                                 31

(2) INFORMATION FOR SEQ ID NO: 43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO: 43:

CTCAACCGTC ACTGAACAGG ACAT                                         24

(2) INFORMATION FOR SEQ ID NO: 44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO: 44:

GCCGCCCCAT ATATCGAACA                                              20

(2) INFORMATION FOR SEQ ID NO: 45:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: other nucleic acid
        (A) DESCRIPTION: /desc = "synthetic DNA (iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO: 45:

GCTCAGGTAA TAGCCCACCA                                                    20

(2) INFORMATION FOR SEQ ID NO: 46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO: 46:

AAAGCCGCCC TCATTGAGGA                                                    20

(2) INFORMATION FOR SEQ ID NO: 47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO: 47:

GGGCAGCGGA TGGCGGAGAT                                                    20

(2) INFORMATION FOR SEQ ID NO: 48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (iii) HYPOTHETICAL: NO (iv) ANTI-SENSE: NO (vi) ORIGINAL SOURCE:
        (A) ORGANISM: Hepatitis-C virus

```
            (xi) SEQUENCE DESCRIPTION: SEQ ID NO: 48:

CACTTACCGT ACATCGAGCA                                                    20

(2) INFORMATION FOR SEQ ID NO: 49:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 49:

GGGATGATGC TCGCCGAGCA                                                    20

(2) INFORMATION FOR SEQ ID NO: 50:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 50:

CAYGTRAGGG TATCGATGAC                                                    20

(2) INFORMATION FOR SEQ ID NO: 51:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA (iii) HYPOTHETICAL: NO (iv) ANTI-SENSE: NO (vi) ORIGINAL SOURCE:
            (A) ORGANISM: Hepatitis-C virus (xi) SEQUENCE DESCRIPTION: SEQ ID NO: 51:

ACTGCCTGAT AGGGTGCTTG CGAG                                               24

(2) INFORMATION FOR SEQ ID NO: 52:

(i) SEQUENCE CHARACTERISTICS:
            (A) LENGTH: 24 base pairs
            (B) TYPE: nucleic acid
```

-continued

```
        (C) STRANDEDNESS: single
        (D) TOPOLOGY: linear (ii) MOLECULE TYPE: other nucleic acid
        (A) DESCRIPTION: /desc = "synthetic DNA (iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO: 52:

AGGTCTCGTA GACCGTGCAT CATG                                              24

(2) INFORMATION FOR SEQ ID NO: 53:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA (iii) HYPOTHETICAL: NO (iv) ANTI-SENSE: NO (vi) ORIGINAL SOURCE:
        (A) ORGANISM: Hepatitis-C virus (xi) SEQUENCE DESCRIPTION: SEQ ID NO: 53:

TTGCGBGACC TWCGCCGGGG GTC                                               23
```

HEPATITIS-C VIRUS TESTING

CROSS REFERENCE TO RELATED APPLICATION

This application is a divisional of U.S. application Ser. No. 12/728,030, filed Mar. 19, 2010, which is a divisional of U.S. application Ser. No. 11/652,862, filed Jan. 12, 2007, now U.S. Pat. No. 7,709,006, which is a continuation of U.S. application Ser. No. 10/396,964, filed Mar. 25, 2003, now U.S. Pat. No. 7,179,470, which is a continuation of U.S. application Ser. No. 09/039,130, filed Mar. 13, 1998, which is a divisional of U.S. application Ser. No. 08/244,116, filed Jul. 15, 1994, now U.S. Pat. No. 5,763,159, which is a continuation of PCT Application No. GB 92/02143, filed Nov. 20, 1992, and also claims the benefit of Great Britain Application No. 9124696.7, filed Nov. 21, 1991, and Great Britain Application No. 9213362.8, filed Jun. 24, 1992, all of which are herein incorporated by reference in their entirety and for all purposes.

TECHNICAL FIELD

The present invention relates to the discovery of new types of hepatitis C virus, that we have termed type 3 (HCV-3) and type 4 (HCV-4). In particular, it relates to the etiologic agent of hepatitis C virus type 3 and 4, and to polynucleotides and immunoreactive polypeptides which are useful in immunoassays for the detection of HCV-3 and HCV-4 in biological samples; and also to the use of antigenic HCV-3 and HCV-4 specific polypeptides in vaccines.

BACKGROUND OF THE INVENTION

Acute viral hepatitis is a disease which may result in chronic liver damage. It is clinically diagnosed by a well-defined set of patient symptoms, including jaundice, hepatic tenderness, and an increase in the serum levels of alanine aminotransferase and aspartate aminotransferase. Serologic immunoassays are generally performed to diagnose the specific type of viral causative agent. Historically, patients presenting with symptoms of hepatitis and not otherwise infected by hepatitis A, hepatitis B, Epstein-Barr or cytomegalovirus were clinically diagnosed as having non-A, non-B hepatitis (NANBH) by default.

For many years, the agent of non-A, non-B hepatitis remained elusive. It has now been established that many cases of NANBH are caused by a distinct virus termed hepatitis C virus (HCV). European Patent Application EP-A-0318216 discloses CDNA sequences derived from HCV, polynucleotide probes and polypeptides for use in immunoassays. Further information is provided in European Application EP-A-0388232.

The HCV genome encodes a large polyprotein precursor, which contains structural and non-structural regions. The single protein is apparently cleaved into a variety of proteins after production. Most of the structural and non-structural proteins have now been identified from in vitro RNA translation and expression as recombinant proteins. The C and E regions encode for nucleocapsid structural proteins and for envelope structural proteins, respectively. At least five additional regions follow, which encode for non-structural (NS) protein of undefined function. The organization is believed to be as follows (A. Alberti, *Journal of Hepatology*, 1991; 12; 279 to 282)

```
5'                                                    3'
NCR: C : E1 : E2 : NS1 : NS2 : NS3 : NS4 : NS5
```

Certain immunoreactive proteins have been described as recombinant proteins, for example C22 (in the core region), C33 (in NS3 region), 5-1-1 and C100 (both in the NS4 region), and NS5 (NS5 region). Diagnosis of hepatitis C is still largely based on methods which detect antibodies against the product of the C-100 clone. This clone was ligated with overlapping clones to produce a larger viral antigen (C100) corresponding to part of the NS3-NS4 genomic region. C100 was then fused with the human superoxide dismutase (SOD) gene, expressed in use as a large recombinant fusion protein (C100-3) and used on solid phase to develop radio-labelled (RIA) and enzyme-linked immunosorbent assays (ELISA).

Polynucleotides useful for screening for HCV are disclosed in European Patent Specification EP-A-0398748. European Patent Specification EP-A-0414475 purports to disclose the propagation of HCV in culture cells and the production of antigens for use in diagnostics. European Patent Specification EP-A-0445423 discloses an improved immunoassay for detecting HCV antibodies.

Blood banks in the United Kingdom have recently begun routine testing of blood donors for antibodies to components of HCV. One assay involves the detection of HCV antibodies to C100-3 polypeptides. The C100-3 antibody recognizes a composite polyprotein antigen within non-structural regions of the virus and is a consistent marker of HCV infection. However, in acute infections this antibody is unreliable because of the delay (typically 22 weeks) in seroconversion after exposure. Furthermore, the C100-3 antibody test lacks specificity for the hepatitis C virus.

Second generation antibody tests employ recombinant antigens or synthetic linear peptides representing structural antigens from the highly conserved core region of the virus as well as non-structural antigens. However, it is found that some second-generation ELISA tests can yield false-positive reactions. The recombinant immunoblot assay (RIBA-2) incorporating four antigens from the HCV genome, provides a method for identifying genuine-anti-HCV reactivity. However, the result can be "indeterminate." The present workers have reported (*The Lancet*, 338; Oct. 19, 1991) varying reactivity of HCV-positive blood donors to 5-1-1, C100, C33C and C22 antigens, and compared these with the results of the direct detection of HCV RNA present in the blood samples using polymerase chain reaction (PCR) to amplify HCV polynucleotides. However, the work demonstrates that the unambiguous diagnosis of HCV infections is not yet possible.

Recently there has been discovered a second type of HCV (References 1, 2) called K2 that differs considerably in sequence from the published prototype (Reference 3) or the first type K1 sequences (References 4 and 5).

SUMMARY OF THE INVENTION

The present invention is based on the discovery of previously unknown type 3 and 4 variants of HCV, by a comparison to sequences amplified by PCR in certain regions of the HCV genome and confirmed by phylogenetic analysis. The invention has thus identified polynucleotide sequences and peptides which are HCV-3 and HCV-4 specific. These may be used to diagnose HCV-3 and HCV-4 infection and should thus be included in any definitive test for HCV infection.

One aspect of the invention provides polynucleotide sequences unique to hepatitis C virus types 3 and 4 (HCV-3 and HCV-4). The sequences may be RNA or DNA sequences. In principal any HCV-3 or HCV-4 specific polynucleotide sequence from non-coding, core, E1, E2 or NS1-5 genome regions can be used as a hybridization probe. The sequences may be recombinant (i.e. expressed in transformed cells) or synthetic and may be comprised within longer sequences if necessary. Equally, deletions, insertions or substitutions may also be tolerated if the polynucleotide may still function as a specific probe. Polynucleotide sequences such as core, NS3, NS4 and NS5 which code for antigenic peptides are particularly useful.

Another aspect provides an antigenic HCV-3 or HCV-4 specific peptide, particularly from the core, NS3, NS4 or NS5 regions (e.g. the HCV-3 or HCV-4 counterparts of C100 peptide, 5-1-1 peptide, C33 peptide or C22 peptide or epitopes thereof) or peptides including these antigens.

The peptide may be a fusion peptide which comprises at least two of the antigenic HCV-3 or HCV-4 specific peptides. A fusion peptide may also comprise at least one of the antigenic peptides fused to β-galactosidase, GST, trpE, or polyhedron coding sequence.

A further aspect of the invention provides labelled antigenic HCV-3 or HCV-4 specific peptide (or mixtures thereof, particularly from the core and NS4 regions) for use in an immunoassay.

A further aspect of the invention provides antibodies to HCV-3 or HCV-4 specific antigens, particularly monoclonal antibodies for use in therapy and diagnosis. Thus labelled antibodies may be used for in vivo diagnosis. Antibodies carrying cytotoxic agents may be used to attack HCV-3 or HCV-4 infected cells.

A further aspect of the invention provides a vaccine comprising immunogenic HCV-3 or HCV-4 specific peptide.

The HCV-3 or HCV-4 specific polynucleotide sequences may be used for identification of the HCV virus itself (usually amplified by PCR) by hybridization techniques.

Oligonucleotides corresponding to variable regions in the NS-4 region could be used for type-specific PCR. Outer sense and inner sense primers may be used in combination with the two conserved anti-sense primers for a specific detection method for HCV types 1, 2, 3 and 4.

Immunoreactive HCV-3 or HCV-4 specific peptides (particularly from the core and NS4 regions) may be used to detect HCV-3 and HCV-4 antibodies in biological samples, and may also provide the basis for immunogens for inclusion in vaccines (especially the E1 polypeptide). The term "peptide" is used herein to include epitopic peptides having the minimum number of amino acid residues for antigenicity, oligopeptides, polypeptides and proteins. The peptide may be a recombinant peptide expressed from a transformed cell, or could be a synthetic peptide produced by chemical synthesis.

In particular, the invention allows blood donor screening by conventional assays (using HCV type 1 encoded antigens) to be supplemented with a second test that contains two oligopeptides corresponding to first and second antigenic regions found in the NS-4 sequence of HCV type 3 (positions 1691 to 1708; sequence KPALVPDKEVLYQQYDEM (SEQ ID NO:1) and positions 1710 to 1728; sequence ECSQAAPYIEQAQVIAHQF (SEQ ID NO:2) and two derived from the equivalent regions of HCV type 2, R(A/V)V(V/I)(A/T)PDKE(I/V)LYEAFDEM (SEQ ID NO:3 or 4) and ECAS(K/R)AALIEEGQR(M/I)AEML (SEQ ID NO:5 or 6).

The corresponding HCV-4 antigens from substantially positions 1691 to 1708 and 1710 to 1728 may be used for HCV-4 detection.

Thus, the present invention has also identified corresponding polynucleotide and peptide sequences which may be used to identify hepatitis C type 2 viral infection.

Production and detection of the antigen-antibody immune complex may be carried out by any methods currently known in the art. For example, a labelling system such as enzyme, radioisotope, fluorescent, luminescent or chemiluminescent labels may be employed, usually attached to the antigen. Labelled anti-antibody systems may also be used. The recombinant antigen may be either used in liquid phase or absorbed onto a solid substrate.

Oligopeptides corresponding to the antigenic regions of all three major types may also be used separately to serologically distinguish individuals infected with different HCV types. Such an assay could be in the format of an indirect enzyme immunoassay (EIA) that used sets of wells or beads coated with peptides of the two major antigenic regions for HCV types 4, 3 (SEQ ID NO:1 or 2) and 2 (SEQ ID NO:3, 4, 5 or 6), and with type 1 (KPA(V/I)IPDREVLYREFDEM (SEQ ID NO:7 or 8) and RPAV(I/V)PDREVLYQEFDEM (SEQ ID NO:9) and ECSQHLPYIEG(M/A)AEQF) (SEQ ID NO:10 or 11). Minor degrees of cross-reactivity, should they exist, can be absorbed out by dilution of the test serum in a diluent that contained blocking amounts of soluble heterologous-type oligopeptides, to ensure that only antibody with type-specific antibody reactivity bound to the solid phase.

Immunogens for use in vaccine formulations may be formulated according to techniques currently known in the art, including the use of suitable adjuvant and immune-stimulation systems.

Furthermore, the present invention also encompasses assay devices or kits including peptides which contain at least one epitope of HCV-3 or HCV-4 antigen (or antibodies thereto), as well as necessary preparative reagents, washing reagents, detection reagents and signal producing reagents. The antigen may be from the core or NS4 regions. The assay device may be in the form of a plate having a series of locations respectively containing HCV-1, HCV-2, HCV-3, and optionally HCV-4, specific antigens.

The invention also provides a method of in vitro testing for HCV which comprises reverse transcribing any HCV polynucleotide present and amplifying by polymerase chain reaction (PCR), and detecting the amplified HCV polynucleotide employing an HCV-2, HCV-3 or HCV-4 specific polynucleotide probe.

The invention further provides a method of in vitro HCV typing which comprises carrying out endonuclease digestion of an HCV-containing sample employing ScrFI or HaeIII/RsaI endonuclease; and comparing the restriction patterns with characteristic type-specific patterns.

The endonuclease digestion may also employ Hinf1 in a separate or the same digestion.

The invention furthermore provides a method of in vitro HCV typing which comprises carrying out endonuclease digestion of an HCV-containing sample employing ScrFI endonuclease, the restriction pattern being characteristic of HCV-1, HCV-2 and HCV-3; carrying out endonuclease digestion employing Hinf1 endonuclease, the restriction pattern being characteristic of HCV-4.

DESCRIPTION OF THE DRAWINGS

Examples of the invention will now be described by way of example only.

FIGS. 1A to 1H give cDNA sequences obtained from PCR amplification of a region −255 to −62 of the 5' non-coding region of HCV samples from 18 blood donors and a comparison with previously published nucleotide sequences (see Table 2); sequence numbering corresponding to the prototype HCV-1 sequence (ref 4) and previous designations of type 1 or 2 being indicated: samples E-b1 through E-b8 represent HCV-3 sequences (SEQ ID NO:12).

FIG. 2 is a phylogenetic analysis showing clustering of the sequences into three types viz; HCV-1, HCV-2 and HCV-3 for the 5' NCR results of FIG. 1 using the maximum likelihood algorithm, shown as an unrooted tree. Numbers 1-18 in full circles correspond to blood donor sequences E-b1 through E-b18. Numbers 1 to 26 in open circles correspond to the previously published sequences identified in Table 2.

FIG. 3 is a comparison of deduced amino acid sequences in the NS-5 region of blood donors (E-b1, E-b2, E-b3, E-b7 (type 3) (SEQ ID NO:13) and E-b12 (type 2) with those previously published (Table 2). Amino acid residue numbering follows that of the HCV-1 polyprotein (4) and uses single letter amino acid codes.

FIG. 5 is a comparison of deduced amino acid sequences in the NS-3 region of blood donors (E-b1, E-b2, E-b6, E-b7 (type 3) (SEQ ID NO:14) with those previously published (Table 2). Group 1/1: amino acid sequence of f1, f3, f4, f5, h2, h3, h4 (one), i2, i3, i4, p1, p2; Group 1/2: amino acid sequence of i5; Group 1/3: amino acid sequence of h2, h3, h4 (one), h5, f2, p3, i1; Group 1/4: amino acid sequence of h1 (one); Group 1/5: amino acid sequence of h1 (one). Numbering, symbols and abbreviations are as described for FIG. 3.

Figure 6:
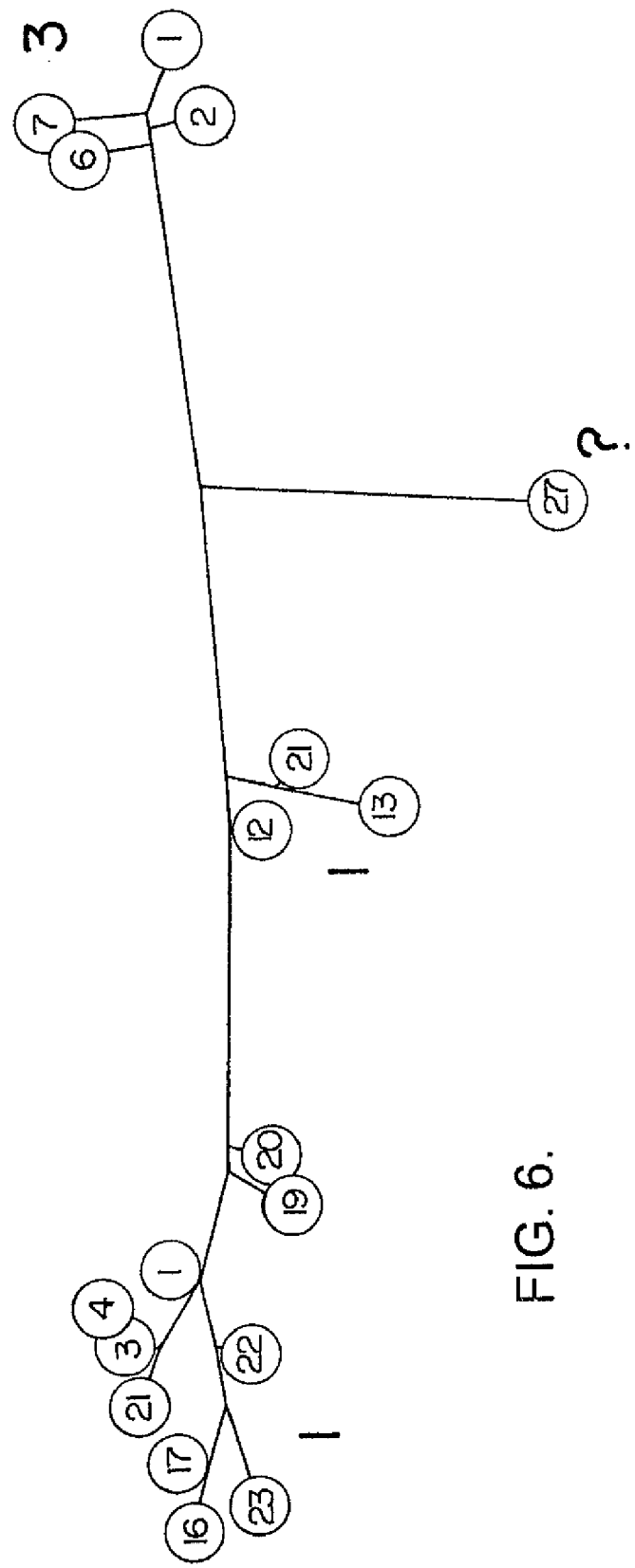

FIG. 6 is a phylogenetic analysis of the NS-3 region using the maximum likelihood algorithm, shown as an unrooted tree. Representative nucleotide sequences of the 5 groups of type 1 sequences shown in FIG. 5 coded as follows: 19 (full circle) i3; 20 (full circle) i4; 21 (full circle) h5; 22 (full circle) h3; 23 (full circle) h1. Symbols are as described for FIG. 2.

FIGS. 7A and 7B are a comparison of deduced amino acid sequences in the core region of blood donor E-b1 (type 3) (SEQ ID NO:15) with those previously published (Table 2). Numbering, symbols and abbreviations are as described for FIG. 3.

Figure 8:
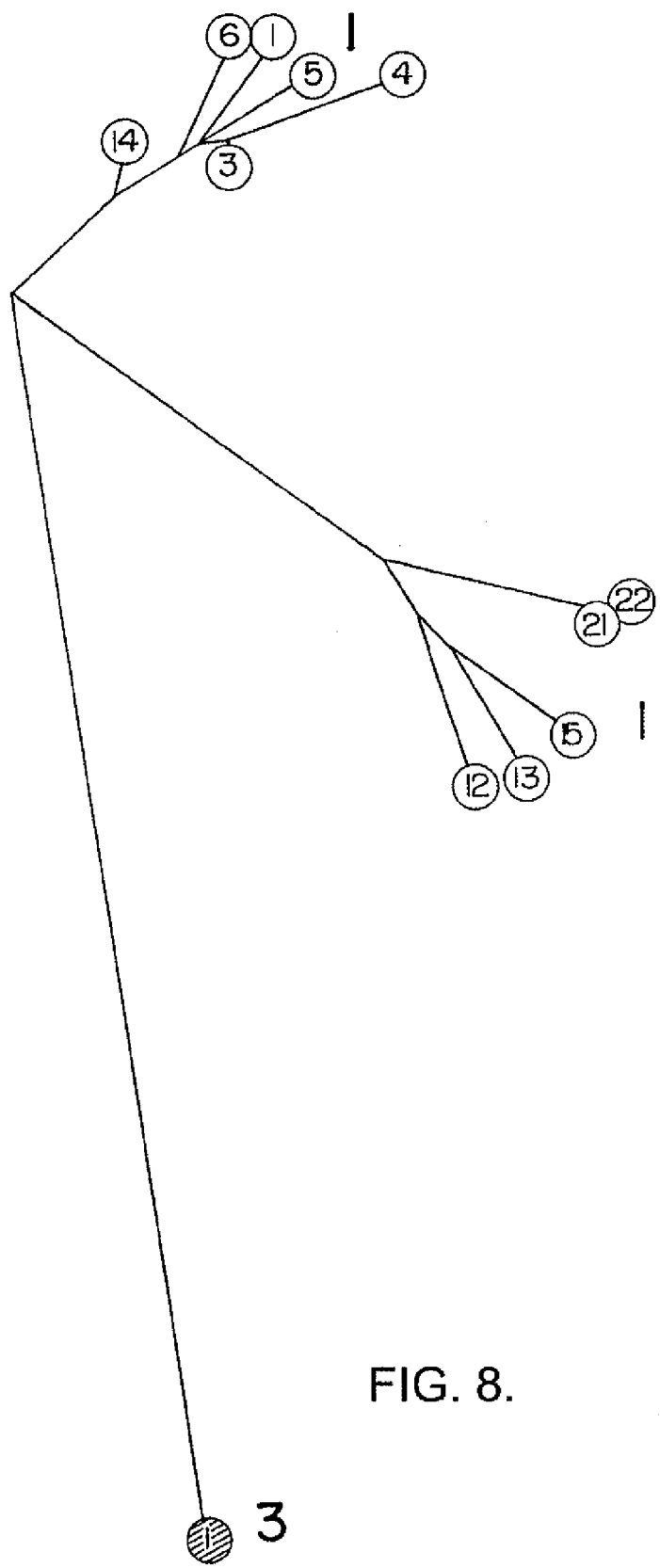

FIG. 8 is a phylogenetic analysis of the core region using the maximum likelihood algorithm, shown as an unrooted tree. Symbols are as described for FIG. 2.

FIGS. 9A and 9B (SEQ ID NO:16) show nucleotide, and FIG. 9C (SEQ ID NO:17) shows deduced amino acid sequences of HCV type 3 variants amplified from 5 Scottish blood donors (nos. 40, 38, 36, 26 and 1787) in the putative NS-4 region of HCV (nucleotides and amino acid residues numbered as in Choo et al., (1991). Nucleotide codes: G: guanidine; C: cytidine; A: adenine; U: uridine; amino acid codes: A: alanine; R: arginine; N: asparagine; D: aspartic acid; C: cysteine; Q: glutamine; E: glutamic acid; G: glycine; H: histidine; I: isoleucine; L: leucine; K: lysine; M: methionine; F: phenylalanine; P: proline; S: serine; T: threonine; W: tryptophan; Y: tyrosine; V: valine. ".": sequence not determined; difference from consensus shown in bold.

FIG. 10A shows a comparison of amino acid sequences between residues 1679 and 1768 (Choo et al., 1991) of the three major variants of HCV. T16, T42, T77, T1801, T1825: Scottish blood donors infected with HCV type 1; T351: Scottish blood donor infected with HCV type 2; T59, T940, T810: Scottish blood donors infected with HCV type 2; T40, T38, T36, T26, T1787: Scottish blood donors infected with HCV type 3 (residues 42 to 128 of SEQ ID NO:17); and FIG. 10B shows the derivation of consensus sequences for HCV types 3 (residues 42 to 128 of SEQ ID NO:17), 2 and 1 oligopeptide series. Differences from consensus shown in bold. Amino acid codes: A: alanine; R: arginine; N: asparagine; D: aspartic acid; C: cysteine; Q: glutamine; E: glutamic acid; G: lycine; H: histidine; I: isoleucine; L: leucine; K: lysine; M: methionine; F: phenylalanine; P: proline; S: serine; T: threonine; W: tryptophan; Y: tyrosine; V: valine; ".": not determined.

Figure 12A:
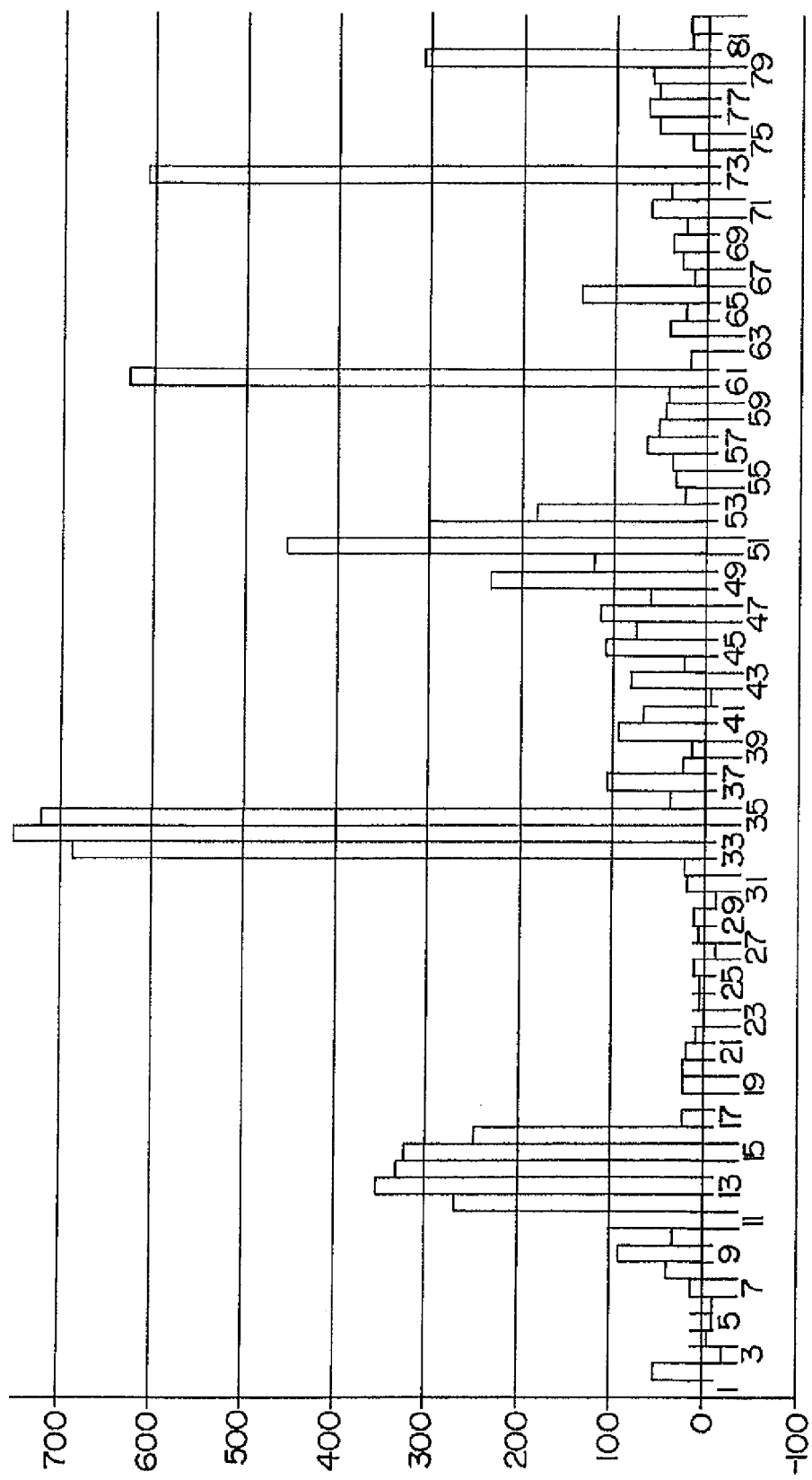
Figure 12B:
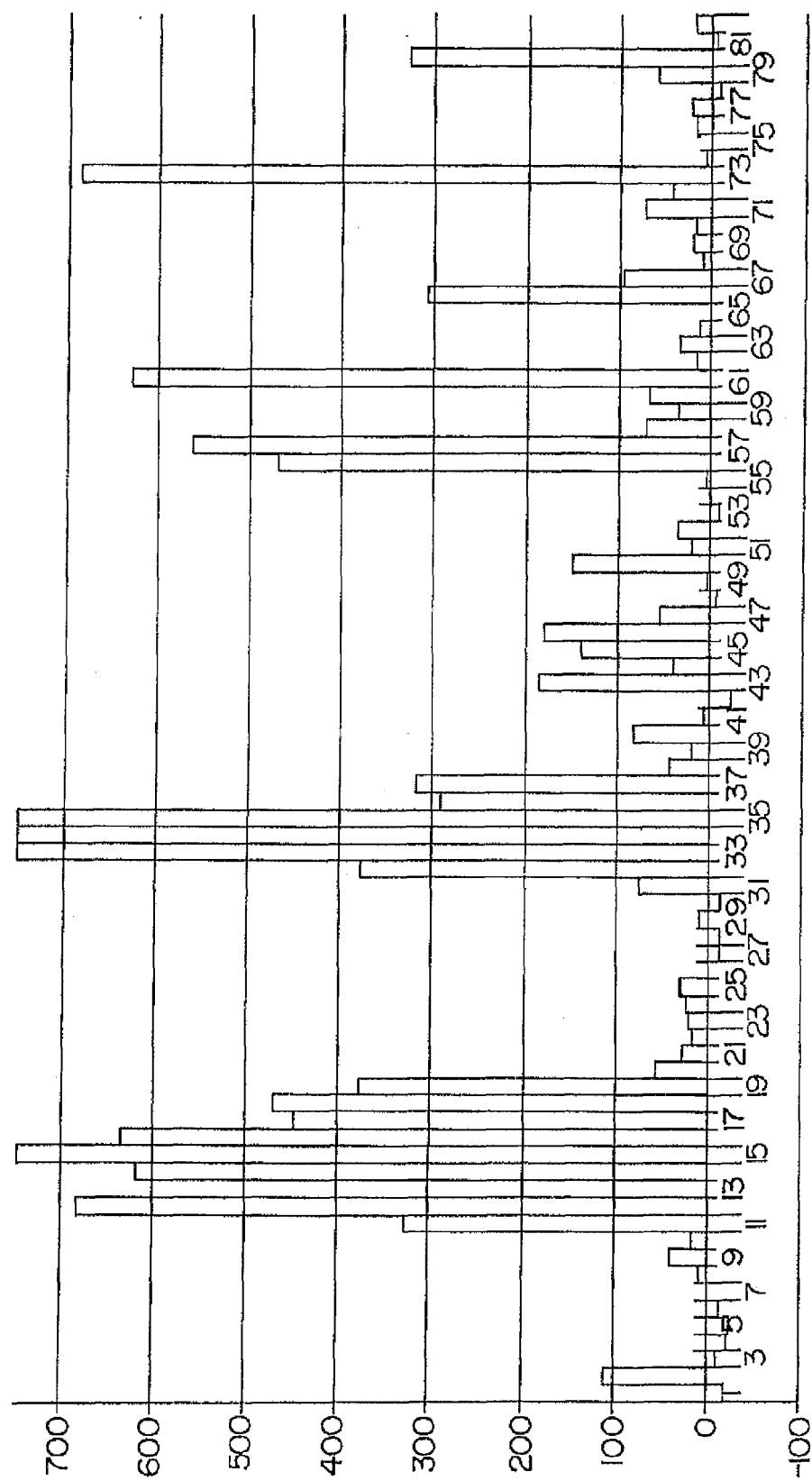
Figure 12C:
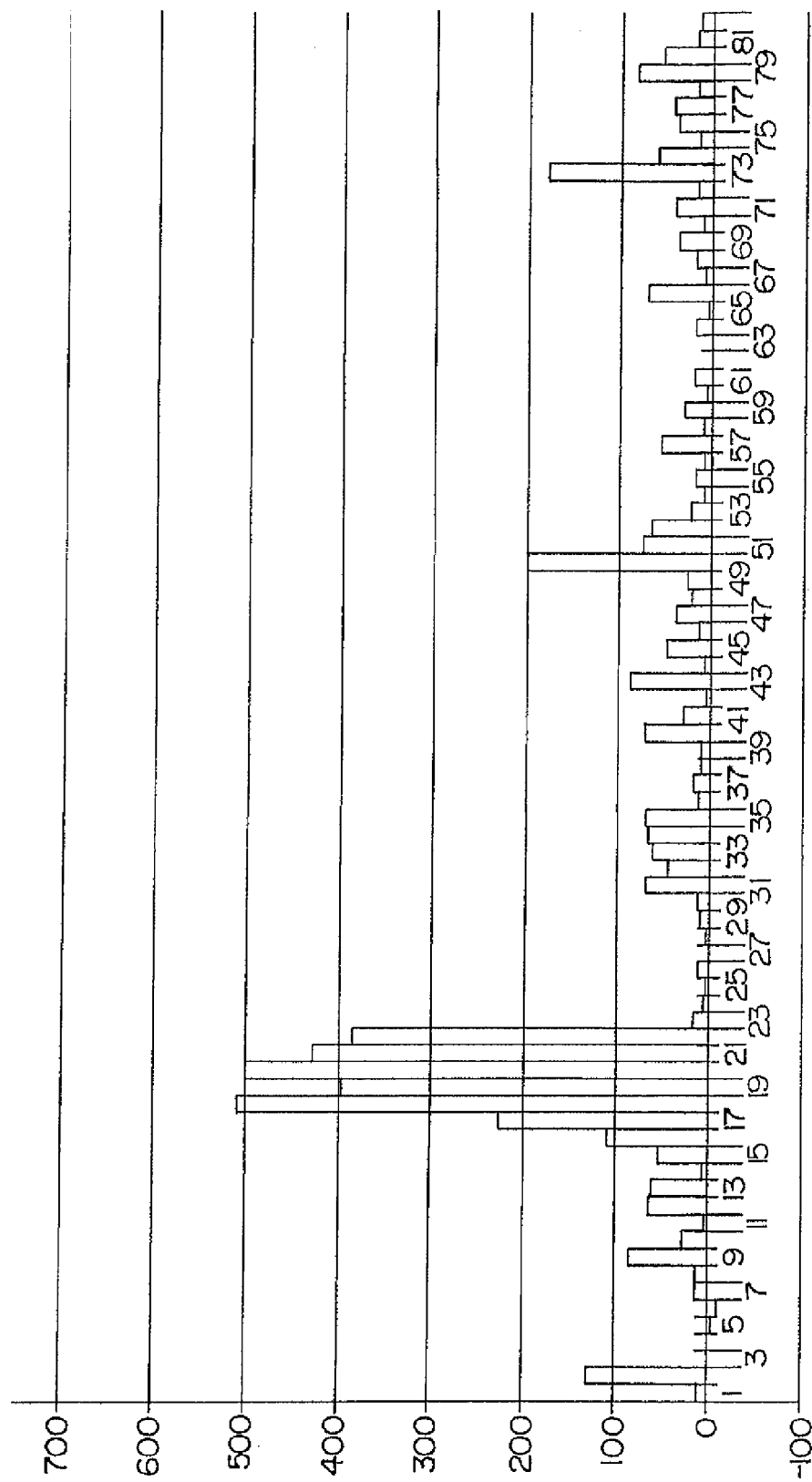
Figure 13D:
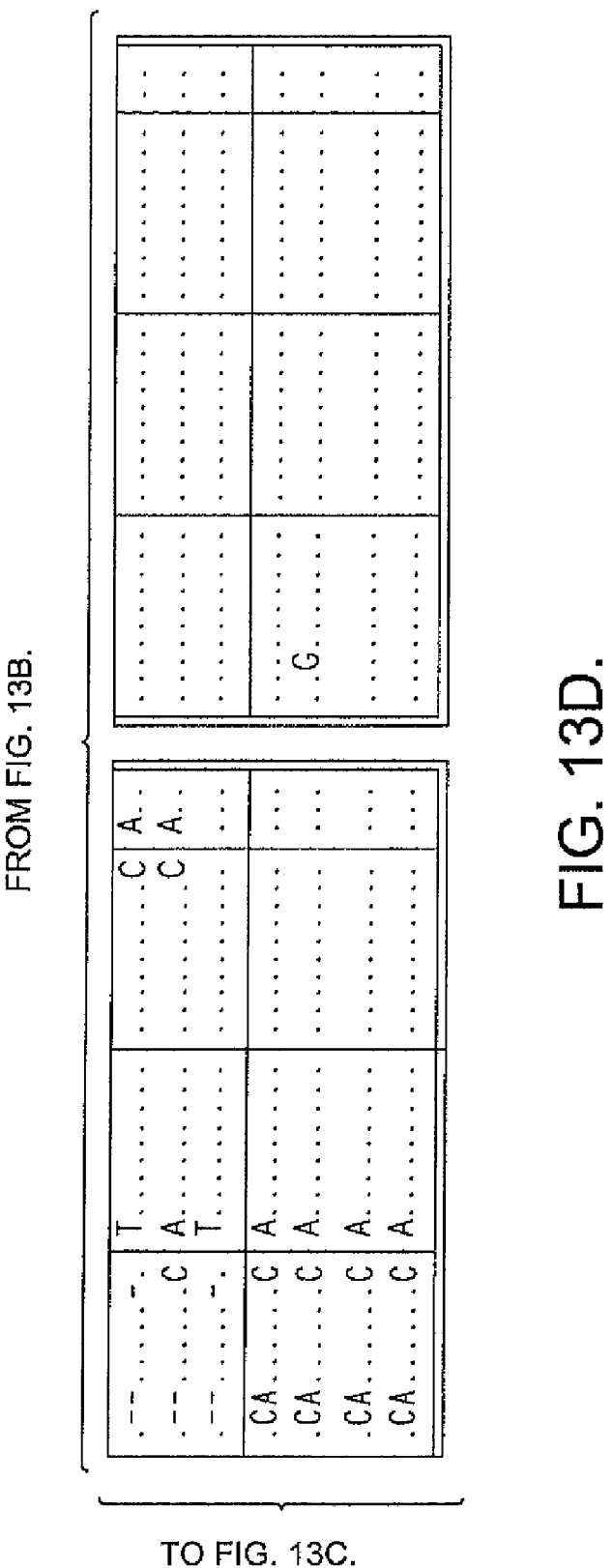

FIGS. 11A to 11F show amino acid sequences of non-americ oligopeptides used for epitope mapping, derived from consensus HCV type 3 (residues 42 to 128 of SEQ ID NO:17), type 2 and type 1 sequences respectively. Amino acid codes: A: alanine; R: arginine; N: asparagine; D: aspartic acid; C: cysteine; Q: glutamine; E: glutamic acid; G: glycine; H: histidine; I: isoleucine; L: leucine; K: lysine; M: methionine; F: phenylalanine; P: proline; S: serine; T: threonine; W: tryptophan; Y: tyrosine; V: valine;

FIGS. 12A, 12B and 12C show antibody reactivity of three sera from blood donors infected with HCV type 3 with HCV type 3-encoded oligopeptides in the antigenic region of NS-4 (sequences 1-82 shown in FIG. 11a) (derived from residues 42 to 128 of SEQ ID NO:17). Antibody reactivity to oligopeptides (x-axis), recorded as optical densities in the range from −01 to 0.75 (and >0.75) recorded on the y-axis.

FIGS. 13A to 13D are a comparison of divergent HCV sequences with representative type 1, 2 and 3 (SEQ ID NO:18) sequences in variable regions of the 5'NCR. Sequences from −255 to −246, −215 to −186, −115 to −102 and −69 to −62 identical to prototype sequence. ".": sequence identity with HCV-1; "..": gap introduced in sequences to preserve alignment; "−": sequence not determined. Origins of sequences: Eg-1-33: Egypt; NL-26: Holland; HK-1-4: Hong Kong; IQ-48: Iraq; XX-96: xxxxx. Figures in parentheses number each non-identical sequence.

Figure 14:
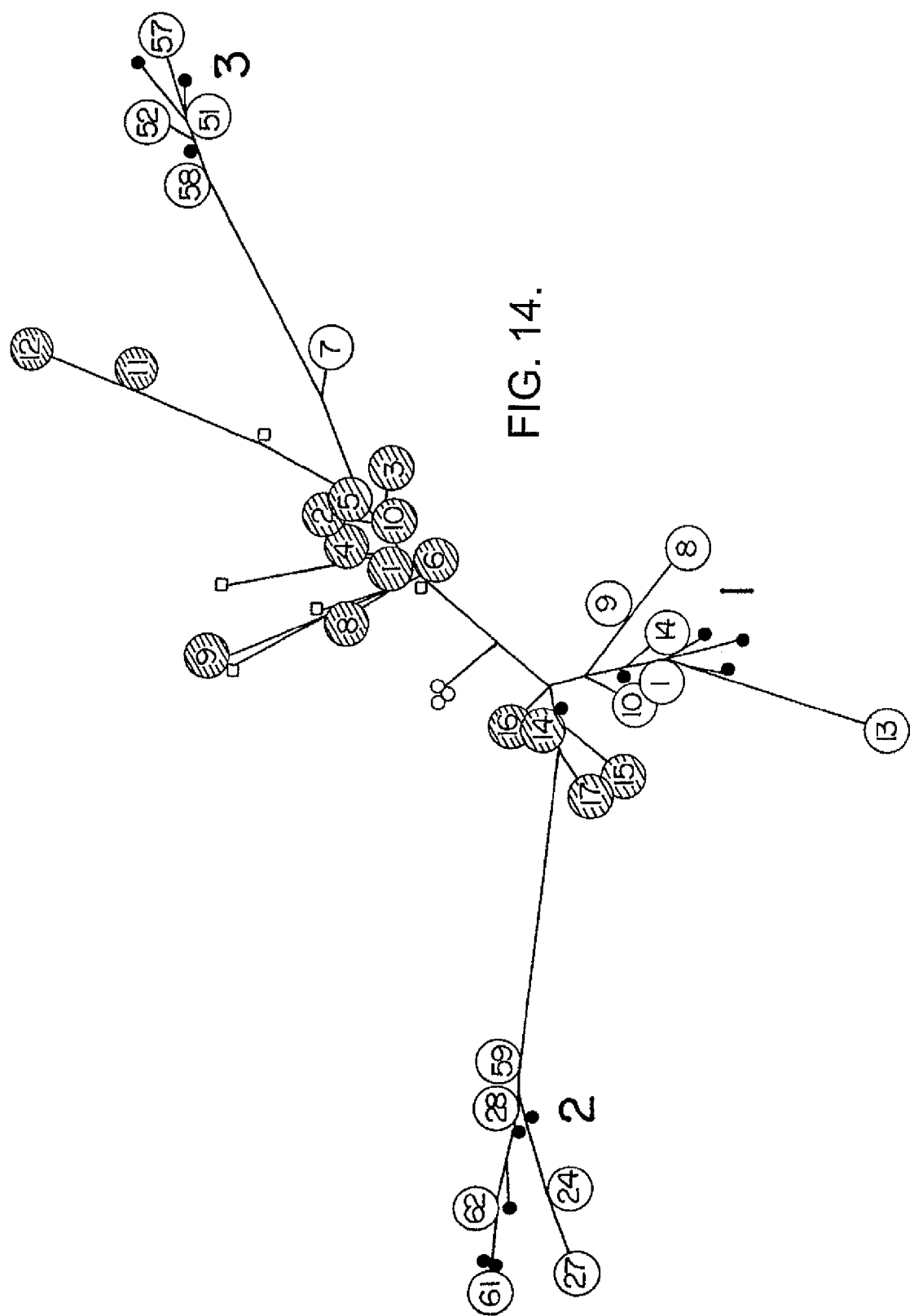

FIG. 14 is a phylogenetic analysis of the 5'NCR region using the maximum likelihood algorithm, shown as an unrooted tree. Sequences 1-17 in solid circles are numbered as in FIG. 13; previously published sequences numbered as in table 1 of (992). Scottish blood donor sequences Eb-1-Eb-12 numbered 51-62 in hollow circles. For clarity, only non-identical sequences are shown in tree; e.g. Sequence 1 corresponds to those found in samples Eg-16 and Eg-29 etc. (FIG. 1). Hollow squares are published sequences from Zaire; Hollow small circles are sequences from South Africa; Hollow small solid circles are sequences obtained elsewhere in the world.

FIGS. 15A and 15B are a comparison of HCV types 1, 2, 3 (SEQ ID NO:19) and 4 (SEQ ID NO:20) nucleotide (A) and HCV types 1, 2, 3 (residues 1 to 89 of SEQ ID NO:15) and 4 (SEQ ID NO:21) amino acid (B) sequences in the core region. Symbols as for FIG. 13. Single letter amino acid codes are used.

Figure 16:
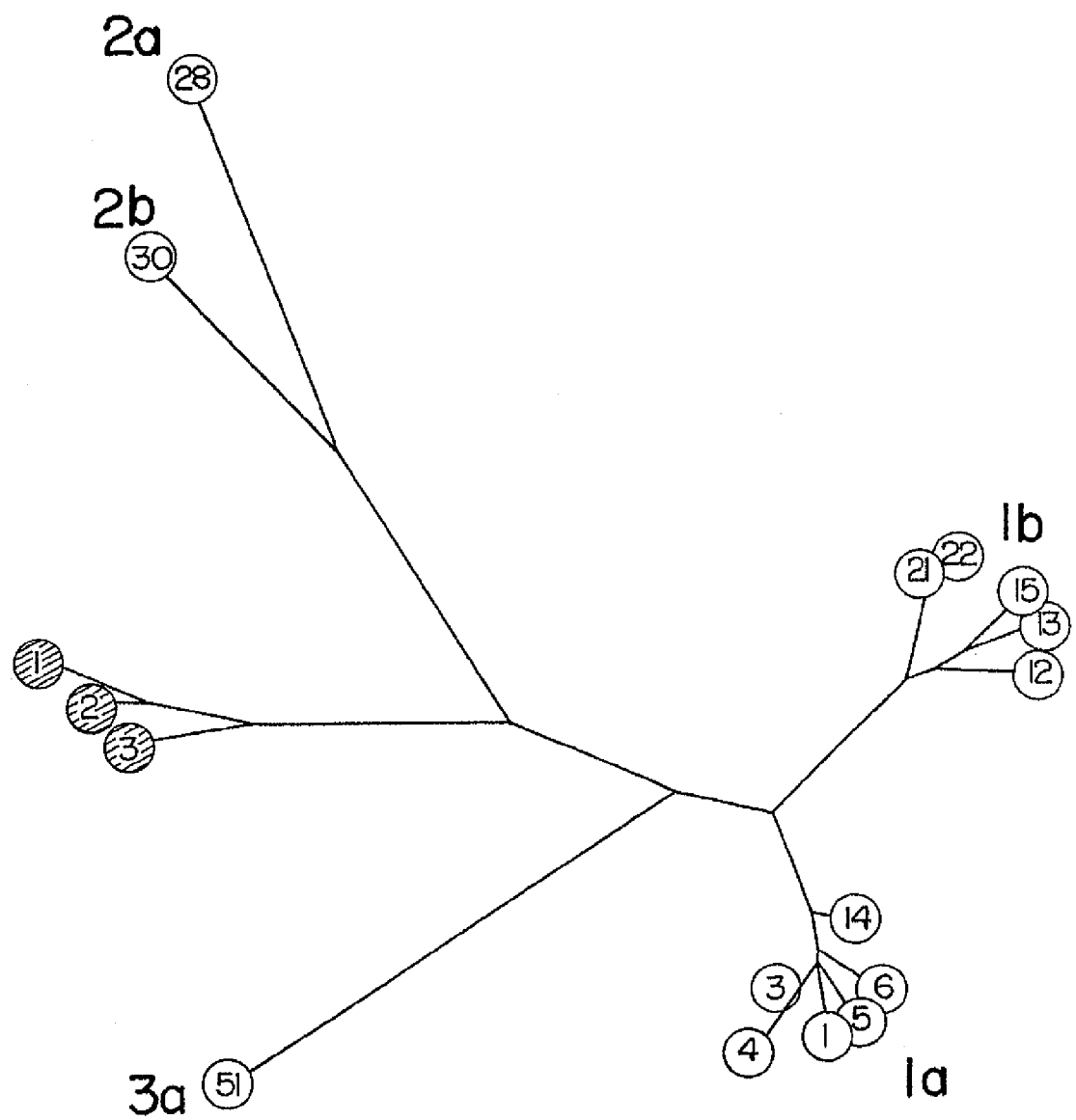

FIG. 16 is a phylogenetic analysis of part of the core region using the maximum likelihood algorithm, shown as an unrooted tree. Sequences are numbered as in FIG. 14; sequence 30 is that of HC-J8 (Okamato et al. *Virology* 188: 331-341).

Figure 17A:
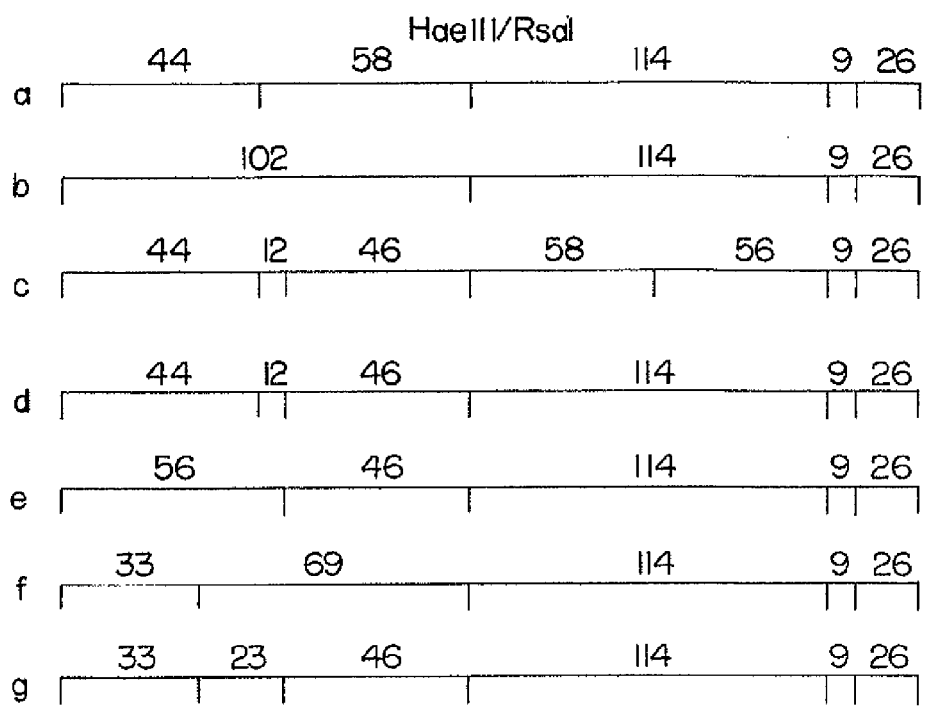
Figure 17B:
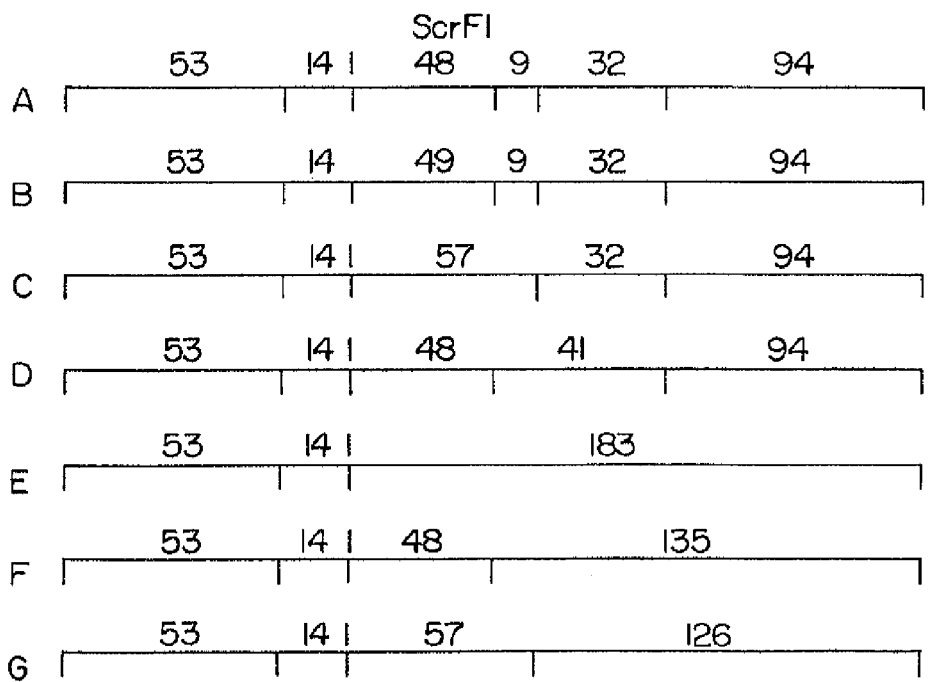

FIGS. 17A and 17B show cleavage patterns for A) HaeIII/RsaI and B) ScrFI in 5'NCR.

DETAILED DESCRIPTION

I. Analysis of Hepatitis C Virus and Phylogenetic Relationship of Types 1, 2 and 3

Introduction

Sequence analysis of the 5' non-coding region of hepatitis C virus (HCV) amplified from the plasma of individuals infected in Britain revealed the existence of three distinct groups of HCV, differing by 9-14% in nucleotide sequence. Two of the groups identified were similar to those of HCV variants previously termed type 1 and type 2, while the third group appeared to represent a novel virus type. Sequence comparisons were then made between the three virus types in other regions of the viral genome. In the NS-5 region, a high degree of nucleotide and amino acid sequence diversity was observed, with samples classified here as type "3" (SEQ ID NO:13) again forming a distinct group that was phylogenetically distinct from type 1 and type 2 variants. Type 3 sequences were similarly differentiated in the NS-3 (SEQ ID NO:14) and core (SEQ ID NO:15 and 19) regions from HCV type 1 sequences. The designation of virus types, including an observed sub-division of type 1 sequences into geographically distinct variants is discussed in relation to the new sequence data obtained in this study.

Discussion

Replication of nucleotide sequences by polymerase chain reaction (PCR) is a recently established technique. Synthetic complementary primer sequences are hybridized to single-stranded DNA on either side of a genome region to be copied. The second strand is built up under the action of a heat-stable polymerase in the region between the primers. Heating then dissociates the two-strands and the replication process starts again. The PCR technique allows tiny amounts of polynucleotide to be amplified provided that there is sufficient sequence information to synthesize the primer sequences.

The major problem associated with the use of the PCR to assess sequence variation using the PCR is the possibility that mismatches between the primers and the variant sequence will prevent amplification. We have used several strategies to overcome this problem. For initial virus detection, we used primers in the 5'NCR, which are reported to be highly conserved amongst type 1 variants (4, 11, 13, 16, 23, 24, 26, 33), and between K1 and K2 (23). Sequence analysis of the blood donors allowed the identification of type 1 and type 2 variants by comparison with published sequence data. This analysis also revealed the existence of a third "type" of HCV (SEQ ID NO:12) that appeared to be as distinct from type 1 as type 2 was (FIGS. 1, 2; Table 3). Based on our initial tentative classification, we sought corroboration of our findings in other (coding) and more variable regions of the viral genome.

Figure 4:
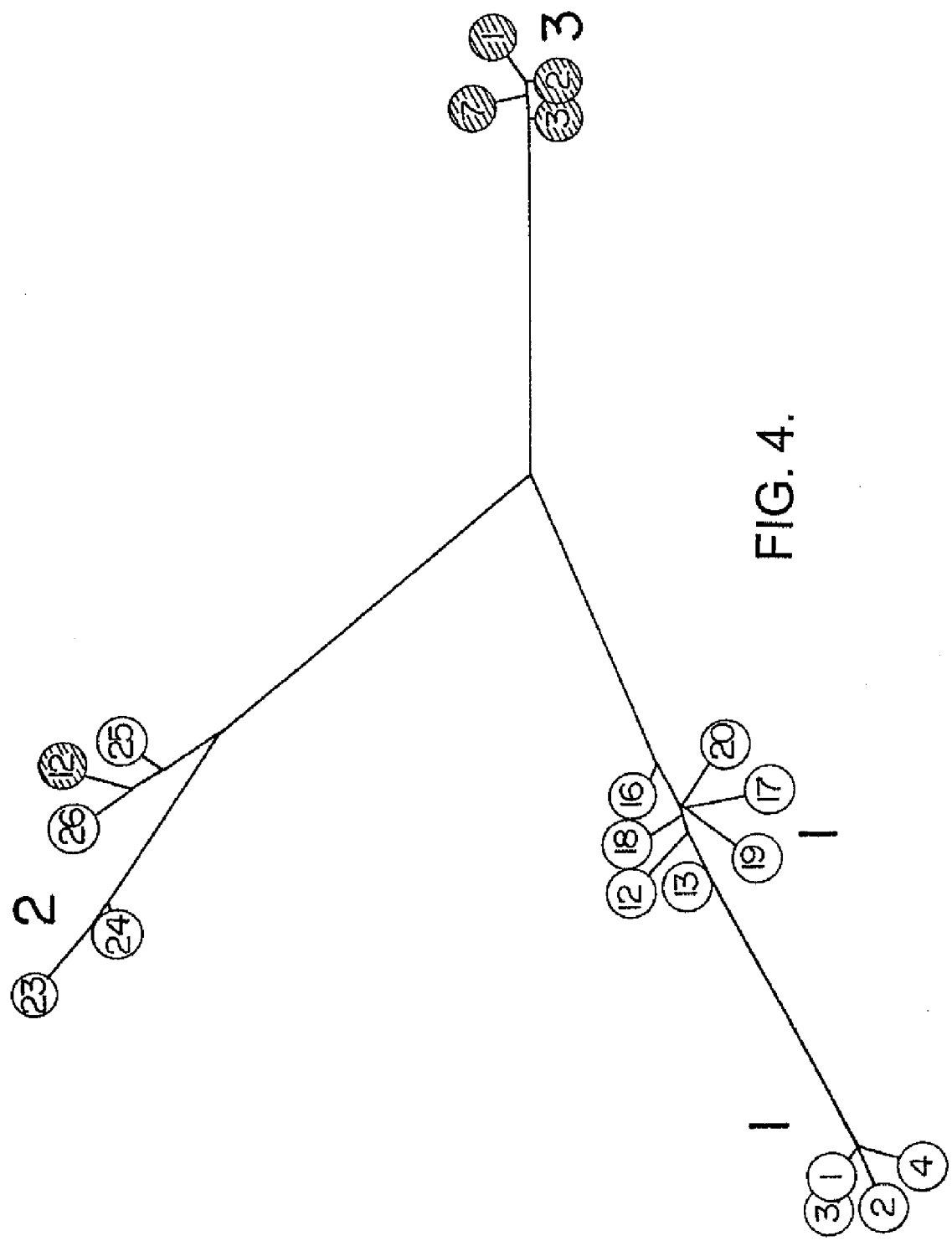
FIG. 4 is a phylogenetic analysis of the NS-5 region using the maximum likelihood algorithm, shown as an unrooted tree. Symbols are as described for FIG. 2.

Analysis of the NS-5 region, which was based on several sequences of each of the three types (FIGS. 3, 4; Table 3), conformed the existence of 3 major groups, with type 3 sequences (SEQ ID NO:13) forming a relatively homogeneous group that was quite distinct from types 1 and 2. The proposed separation of type 1 sequences into PT and K1 "sub-types" and type 2 sequences into K2a and K2b is supported by this analysis, in which the single type 2 blood donor sequence obtained in this study appears most similar to K2b. Differential n of HCV type 1 sequences into two groups is also clearly shown in the core (FIG. 7) and NS-3 regions (FIG. 5), in both cases with the type 3 sequences (SEQ ID NO:15 and 14, respectively) appearing considerably more distant.

The clustering of phylogenetically distinct groups, their mixed distributions in a single geographic area (1, 7, 23, 27, 35) and our own finding of dual or triple infections in individual hemophiliacs all strongly suggest that the three types described here are distinct viruses rather than simply representing geographical or epidemiologically clustered variants of a single, highly variable but monophyletic group.

Our own phylogenetic analysis of the 5'NCR reveals the existence of three distinct groups. This contrasts with analyses of coding region, where there appears to be a very prominent differentiation of type 1 sequences into two "subtypes". However, unlike type 2 and 3 variants, the two subtypes are geographically distinct, one sub-type comprising sequences obtained exclusively from Japanese patients, and the other comprising predominantly USA/European sequences (Table 2). Indeed the only exception to this geographical classification is the HC-J1 sequence (26); one apparent exception (Pt-1) was obtained from a Japanese hemophiliac treated with imported factor VIII of USA origin (7, 23), which is likely to have contained HCV variants corresponding to the other sub-type. There is insufficient sequence data to indicate whether the two proposed type 2 subtypes, K2a and K2b (7, 23) represent geographically distinct variants.

The genomic organization of HCV corresponds to that of flaviviruses and pestiviruses, with a single open reading frame encoding a polyprotein that is subsequently cleaved into structural and non-structural proteins. Weak sequence homologies have been detected with several other virus groups that have positive-sense RNA genomes (19, 21). Although the overall degree of sequence dissimilarity between types 1, 2 and 3 cannot be measured by comparison of the small regions of sequence analyzed in this study, a rough estimate of the extent of divergence in protein coding regions is given by an examination of the divergence of the partial core sequence. This shows that the difference between HCV type 1 and type 3 (SEQ ID NO:15) core region (approximately 10% amino acid sequence divergence) is comparable to that which exists between different serotypes of the flavivirus, tick-borne encephalitis virus (14%; ref. 20), but lower than that which is found between serotypes of a mosquito borne flavivirus, dengue fever virus (33%), and the West Nile (WN) subgroup (28-43% divergence). The 5'NCR sequences of the different members of WN subgroup are also considerably more diverse than those of the three types of HCV (=50% similarity; ref. 5), although within each of the members e.g. Murray Valley encephalitis virus, the 5'NCR is extremely well conserved (>95% similarity; ref 5). On the basis of these analogies, we speculate that the major types of HCV represent distinct "serotypes," each capable of human infection irrespective of the immune response mounted against other HCV types.

Methods

Samples. Plasma from 18 different blood donors (E-b1 through E-b18), that were repeatedly reactive on screening by Abbott 2nd generation enzyme immunoassay (EIA), and confirmed or indeterminate by a recombinant immunoblot assay (RIBA; Ortho; ref 1) were the principal samples used in this study. Sequences in the NS-3 region from 5 anti-HCV positive IVDUs (abbreviated as i1-i5 in ref. 31), 5 hemophiliacs who had received non-heat treated clotting concentrate, and who were also anti-HCV positive (h1-h5), 3 pools of 1000 donations collected in 1983 (p1-p3), and 5 separate batches of commercially available non-heat treated factor VIII (f1-f5) correspond to those described previously (31).

Primers. The primers used for cDNA synthesis and polymerase chain reaction (PCR) are listed in Table 1 (SEQ ID NO:22 through 43). They were synthesized by Oswel DNA Service, Department of Chemistry, University of Edinburgh.

RNA Extraction and PCR. HCV virions in 0.2-1.0 ml volumes of plasma were pelleted from plasma by ultracentrifugation at 100,000 g for 2 hours at 4° C. RNA was extracted from the pellet as previously described (2, 31). First strand cDNA was synthesized from 3 µl of RNA sample at 42° C. for 30 min. with 7 units of avian myeloblastosis virus reverse transcriptase (Promega) in 20 µl buffer containing 50 mM Tris-HCl (pH 8.0), 5 mM $MgCl_2$, 5 mM dithiothreitol, 50 mM KCl, 0.05 µg/µl BSA, 15% DMSO, 600 µM each of dATP, dCTP, dGTP and TTP, 1.5 µM primer and 10 U RNAsin (Promega).

PCR was performed from 1 µl of the cDNA over 25 cycles with each consisting of 25 sec. at 94° C., 35 sec. at 50° C. and 2.5 min. at 68° C. The extension time for the last cycle was increased to 9.5 min. The reactions were carried out with 0.4 unit Taq polymerase (Northumbria Biologicals Ltd.) in 20 µl buffer containing 10 mM Tris-HCl, pH 8.8, 50 mM KCl, 1.5 mM $MgCl_2$, 0.1% Triton X-100, 33 uM each of dATP, dCTP, dGTP and dTTP and 0.5 µM of each of the outer nested primers. One µl of the reaction mixture was then transferred to a second tube containing the same medium but with the inner pair of nested primers, and a further 25 heat cycles were carried out with the same program. The PCR products were electrophoresed in 3% low melting point agarose gel (IBI) and the fragments were detected by ethidium bromide staining and UV illumination. For sequence analysis, single molecules of cDNA were obtained at a suitable limiting dilution at which a Poisson distribution of positive and negative results was obtained (30).

Direct Sequencing of PCR Products. The PCR products were purified by glass-milk extraction ("GeneClean1"; Bio101, Inc.). one quarter of the purified products was used in sequencing reactions with T7 DNA polymerase (Sequenase; United States Biologicals) performed according to the manufacturer's instructions except that the reactions were carried out in 10% DMOS and the template DNA was heat denatured before primer annealing.

Phylogenetic Methods. The sequences were compiled by version 2.0 of the programs of Staden (32) and analyzed by programs available in the University of Wisconsin Genetics Computer Group sequence analysis package, version 7.0 (6). Phylogenetic trees were inferred using two different programs available in the PHYLIP package of Felsenstein (version 3.4 June 1991; ref. 9). The program DNAML finds the tree of the highest likelihood (the maximum likelihood tree) given a particular stochastic model of molecular evolution and has been shown to perform well in simulation studies (28). In the analyses performed here the global (G) option was used as this searches a greater proportion of all possible trees. The second program used was NEIGHBOR which clusters (following the algorithm of Saitou & Nei: ref 29) a matrix of nucleotide distances previously estimated using the program DNADIST (which itself was set, using the D option, to use the same stochastic model as underlies DNAML in order to estimate distances corrected for the probabilities of multiple substitution). In all cases the maximum likelihood and neighbor joining procedures produced congruent trees and thus only the former have been presented here.

To establish the interrelationships of the major types of HCV, we have separately analyzed several regions of the viral genome that differ in sequence variability and evolutionary constraint. Thus the conclusions drawn from the sequence comparisons are not subject to spurious evolutionary phenomena that may affect a particular region. However, one problem with the analysis presented here was the absence of a viral sequence that was sufficiently distantly related to HCV to serve as an out-group. Thus, although we describe the interrelationships of different sequence variants of HCV, it should be stressed that we have no means of deciding which sequence is ancestral to the others. The trees are thus drawn in the less familiar un-rooted form to indicate this.

Results

1) Analysis of the 5' non-coding region. Samples were obtained from 18 blood donors that were repeatedly reactive in the Abbott 2nd Generation enzyme immunoassay and which were confirmed or indeterminate in the Chiron 4-RIBA (E-b1 through E-b18, ref 10). HCV sequences present in stored plasma samples from each donor were amplified with primers corresponding to sites in the 5'NCR (SEQ ID NO:22 through 25) (12, 25) that are well conserved between all known HCV type 1 and type 2 variants (4, 11, 13, 16, 23, 24, 26, 33). Sequencing of the PCR product, after limiting dilution to isolate single molecules of CDNA before amplification, allowed approximately 190 bps in the centre of the region to be compared with equivalent published sequences (FIG. 1).

Within the sequences, constant as well as variable regions can be found. Six sequences from donors E-b13 through E-b18 closely resembled those previously described as type 1 (4, 11, 13, 16, 23, 24, 26, 33) and others resembled type 2 (23) sequences (E-b9 through E-b12). However, eight sequences (E-b1 through E-b8) were distinct from both types, and have been provisionally termed type 3 (SEQ ID NO:12). Division of the sequences into three types is supported by formal phylogenetic analysis using the maximum likelihood (FIG. 2) and neighbor joining algorithms (data not shown) of the blood donor sequences along with previously published sequences (identified in Table 2). Sequence variability within the three groups is in each case considerably less than that which separates the types. No sequence intermediate between the three types were found. This tree shows that the provisionally identified type 3 group (SEQ ID NO:12) is equally distinct from type 1 as is type 2. Using the DNAML model, the corrected distances between sequences within each type were in each case less than 3%. Between groups, they ranged from 9% (between type 1 and type 3 (SEQ ID NO:12), and between type 1 and 2), to 14% between type 2 and type 3 (SEQ ID NO:13) (Table 3).

2) Analysis of the NS-5 Region. The nucleotide sequence of the NS-5 region has been found to vary significantly between the previously described K1 and K2 variants of HCV (7). To investigate whether type 3 (SEQ ID NO:13) sequences were equally distant from the other two types in this region as well as in the 5'NCR, we compared sequences from four type 3 blood donors (E-b1, E-b2, E-b3 and E-b7) and one type 2 donor (E-b12) with previously published sequences (FIG. 3; FIG. 4; Table 3).

A remarkable variation was observed between sequences of the three types in this region. Again, type 3 sequences (SEQ ID NO:13) form a separate group from type 1 and type 2 in this region. However, unlike the 5'NCR, there appear to be subdivisions within the type 1 and type 2 groups. Type 1 sequences are split between those found in Japanese infected individuals (e.g. HCV-J; HCV-BK; sequence numbers 12, 13, 16-20 in Table 2) and those of USA origin (HCV-1, Pt-1, H77, H90; sequence numbers 1-4; FIG. 4). There is also some evidence for a split between type 2 sequences, those corresponding to their previous designation as K2a (7) appearing distinct from type K2b sequences and the Scottish blood donor, E-b12.

Table 3 shows that the average nucleotide distances between the two groups of HCV type 1 sequences is 25% (indicated here as type 1a [USA] and type 1b [Japanese]), with variation of only 4-7% within each group. The nucleotide sequence divergence within the two type 1 groups is similar to that which exists between K2a and K2b (Table 3).

However, both of these distances are considerably less than those which exist between type 1 and type 2 sequences (52-62%), and type 3 (SEQ ID NO:13) (48-49%), and the distance between type 2 and type 3 (SEQ ID NO:13) sequences (53-60%).

3) Analysis of the NS-3 region. Amplification reactions were carried out using previously published primer sequences in the NS-3 region (37), and a pair of empirically derived inner primers (SEQ ID NO:28 and 29) (31). Although these primers amplified HCV sequences from a high proportion of anti-C-100 positive sera from hemophiliacs (31), they were less effective with sera from IVDUs (31), and with blood donor samples (3 positive out of 15 tested; data not shown). Two conserved sites in the amplified fragment were identified by sequence analysis of the NS-3 region from the hemophiliac and IVDU patients, and two new primers corresponding to these were specified (207 (SEQ ID NO:31), 208 (SEQ ID NO:30); Table 1). The combination of 288 (SEQ ID NO:28)-208 (SEQ ID NO:30) (first round) and 290 (SEQ ID NO:29)-207 (SEQ ID NO:31) (second round) primers successfully amplified samples from four donors infected with HCV type 3 (E-b1, E-b2, E-b6 and E-b7) but none of those infected with HCV type 2 (data not shown). This enabled a comparison of the new type (SEQ ID NO:14) with our own (31) and previously published type 1 sequences (FIGS. 5, 6; Table 3). For clarity, only seven of the type 1 sequences obtained in this study (E-b16, E-b17, i3, i3, h5, h3 and h1) are shown in the tree. These sequences are representative of the range of variation found in this region in individuals infected in Britain; comparison of the tree previously published (31) with FIG. 6 shows that the former forms a very small component of the overall tree obtained once Japanese type 1 and type 3 sequences are added.

The maximum likelihood tree shows that type 1 and type 3 (SEQ ID NO:14) have diverged considerably from each other. As was found in the NS-5 region, subtypes of type 1 sequences are found in NS-3. Again, sequences of Japanese origin (HCV-J, HCV-BK and JH) are distinct from the prototype (PT) sequence, and those found in Scottish blood donors (E-b16, E-b17, p1-3), IVDUs (i1-5) and hemophiliacs (h1-5), all of which correspond to the prototype sequence (FIG. 5). However, the average subtype difference (23%) is lower than those that exist between HCV-1 and HCV-J with the four type 3 sequences (SEQ ID NO:14) (37-43%). As reported previously (31), the majority of nucleotide substitutions that exist between type 1 sequences are silent (i.e. do not affect the encoded amino acid sequence), while numerous amino aced substitutions exist between type 1 and type 3 (SEQ ID NO:14) sequences (FIG. 5). The analysis of the NS-3 region includes the sequence of clone A (35) which was obtained from Japanese patients with NANB hepatitis, and which was reported to be distinct from existing HCV type 1 sequences. In FIG. 6, this sequence appears to be distinct from both HCV type 1 and type 3 (SEQ ID NO:14), with corrected sequence distances of 33-43% and 36% respectively. Although it is not possible to assign this sequence to any known group at this stage, these distances are not inconsistent with the hypothesis that it represents a type 2 sequence, or an equally distinct novel HCV type.

4) Partial Sequence of the Putative Core Region of HCV. The region encoding the putative core protein is comparatively well conserved in its nucleotide sequence between known type 1 variants, showing nucleotide and amino acid sequence similarities of 90-98% and 98-99% respectively (11, 24). Part of the core region from the blood donor Eb1, who has type 3 sequences in other regions analyzed was amplified with primers 410 (SEQ ID NO:26) and 406 (SEQ ID NO:27) and compared with previously published type 1 sequences (FIGS. 7, 8; Table 3). This analysis confirms that the type 3 sequence (SEQ ID NO:15) was distinct from those of type 1, and again there was a prominent subdivision of type 1 sequences into Japanese (HCV-J, HCV-BK, HC-J4, JH and J7) and USA/European (HCV-1, H77, H90, GM1, GM2) sequences. As was found in NS-3, very little amino acid sequence variation is found in the core regions of type 1 sequences; almost all of the nucleotide differences between the two groups are at "silent" sites. By contrast, the type 3 sequence (SEQ ID NO:15) shows 7-8 amino acid substitutions on comparison with type 1 sequences.

TABLE 1

SEQUENCES AND SOURCES OF PRIMERS USED FOR AMPLIFICATION OF HCV GENOME

| Name | Region | Position of 5'base' | Sense[b] | Sequences 5'-3' | Ref. |
|------|--------|---------------------|----------|-----------------|------|
| 209 | 5'NCR | 8 | − | ATACTCGAGGTGCACGGTCTACGAGACCT (SEQ ID NO: 22) | (12) |
| 211 | 5'NCR | −29 | − | CACTGCTCGACCCTATCAGGCAGT (SEQ ID NO: 23) | (12) |
| 939 | 5'NCR | −297 | + | CTGTGAGGAACTACTGTCIT (SEQ ID NO: 24) | (25) |
| 940 | 5'NCR | −279 | + | TTCACGCAGAAAGCGTCTAG (SEQ ID NO: 25) | (25) |
| 410 | CORE | 410 | − | ATGTACCCCATGAGGTCGGC (SEQ ID NO: 26) | |
| 406 | CORE | −21 | + | AGGTCTCGTAGACCGTGCATCATGAGCAC (SEQ ID NO: 27) | |
| 288 | NS-3 | 4951 | − | CCGGCATGCATGTCATGATGTAT (SEQ ID NO: 28) | (31) |
| 290 | NS-3 | 4932 | − | GTATTTGGTGACTGGGTGCGTC (SEQ ID NO: 29) | (31) |
| 208 | NS-3 | 4662 | + | TCITGAATTTTGGGAGGGCGTCTT (SEQ ID NO: 30) | |
| 207 | NS-3 | 4699 | + | CATATAGATGCCCACITCCTATC (SEQ ID NO: 31) | |
| 007 | NS-4 | 5293 | − | AACTCGAGTATCCCACTGATGAAGTTCCACAT (SEQ ID NO: 32) | |
| 220 | NS-4 | 5278 | − | CACATGTGCITCGCCCAGAA (SEQ ID NO: 33) | |

TABLE 1-continued

SEQUENCES AND SOURCES OF PRIMERS USED FOR AMPLIFICATION OF HCV GENOME

| Name | Region | Position of 5'base[a] | Sense[b] | Sequences 5'-3' | Ref. |
|---|---|---|---|---|---|
| HCV type 3:¶ | | | | | |
| 221 | NS-4 | 4858 | + | GGACCTACGCCCCITCTATA (SEQ ID NO: 34) | |
| 008 | NS-4 | 4878 | + | TCGGTTGGGGCCTGTCCAAAATG (SEQ ID NO: 35) | |
| HCV type 2: | | | | | |
| 281 | NS-4 | 4858 | | GGTCCCACCCCTCTCCTGTA (SEQ ID NO: 36) | |
| 509 | NS-4 | 4878 | | CCGCITGGGTTCCGTTACCAACG (SEQ ID NO: 37) | |
| HCV type 1: | | | | | |
| 253 | NS-4 | 4858 | | GGGCCAACACCCCTGCTATA (SEQ ID NO: 38) | |
| 196 | NS-4 | 4878 | | CAGACTGGGCGCCGTTCAGAATG (SEQ ID NO: 39) | |
| 242 | NS-5 | 8304 | − | GGCGGAATTCCTGGTCATA000TCCGTGAA (SEQ ID NO: 40) | (7) |
| 555 | NS-5 | 8227 | − | CCACGACTAGATCATCTCCG (SEQ ID NO: 41) | |
| 243 | NS-5 | 7904 | + | TGGGGATCCCGTATGATACCCGCTGCTTTGA (SEQ ID NO: 42) | (7) |
| 554 | NS-5 | 7935 | + | CTCAACCGTCACTGAACAGGACAT (SEQ ID NO: 43) | |

[a]Position of 5'base relative to HCV genomic sequence in ref. no. (4)
[b]Orientation of primer sequence (+: sense: −: anti-sense)
‡Abbreviations: A: adenine. C: cytidine: G: guanidine. T: thymidine.
¶Separate sense primers required to enable amplification of each HCV type

TABLE 2

SOURCE AND CITATION OF PREVIOUSLY PUBLISHED HCV SEQUENCES USED IN THIS STUDY

| No | Type | Abbreviation | Geographical Source | Reference | Ref. No. |
|---|---|---|---|---|---|
| 1 | 1 | HCV-1 | U.S.A | Choo et al., 1991 | (4) |
| 2 | 1 | Pt-1 | Japan | Nakao et al., 1991 | (23) |
| | | | | Enomoto et al., 1990 | (7) |
| 3, 4 | 1 | H77. H90 | U.S.A | Ogata et al., 1991 | (24) |
| 5.6 | 1 | GM-1. GM-2 | Germany | Fuchs et al., 1991 | (11) |
| 7 | 1 | I1 | Japan | Han et al., 1991 | (13) |
| 8 | 1 | A1 | Australia | Han et al., 1991 | (13) |
| 9 | 1 | S 1 | S. Africa | Han et al., 1991 | (13) |
| 10 | 1 | T1 | Taiwan | Han et al., 1991 | (13) |
| 11 | 1 | U18/I24 | U.S.A/Italy | Han et al., 1991 | (13) |
| 12 | 1 | HCV-J | Japan | Kato et al., 1990 | (16) |
| 13 | 1 | HCV-BK | Japan | Takamizawa et al., 1991 | (33) |
| 14-15 | 1 | HC-J1.4 | Japan | Okamoto et al., 1990 | (26) |
| 16-20 | 1 | Kl. Kl-1-4 | Japan | Enomoto et al., 1990 | (7) |
| 21 | 1 | JH | Japan | Kubo et al., 1990 | (17) |
| 22 | 1 | J7 | Japan | Takeuchi et al., 1990 | (34) |
| 23-26 | 2 | K2a. K2a-1 02 b. K2b-1 | Japan | Nakao et al., 1991 Enomoto et al., 1990 | (23) (7) |
| 27 | ? | Clone A | Japan | Tsukiyama-Kohara 1991 | (35) |

TABLE 3

NUCLEOTIDE DISTANCES BETWEEN THE THREE HCV TYPES IN FOUR REGIONS OF THE GENOME.

| REGION | TYPES (n1) | Ia | 1b | 2a | 2b | 3 |
|---|---|---|---|---|---|---|
| 5'NCR | 1 (20) | 0.0163 | n/a[b] | | | |
| | 2 (6) | 0.0869 | n/a | 0.0214 | | |
| | 3 (8) | 0.0948 | n/a | 0.1331 | n/a | 0.0123 |
| CORE | 1a (6) | 0.0358 | | | | |
| | 1b (5) | 0.0855 | 0.0227 | | | |
| | 3 (1) | 0.1801 | 0.1511 | n/d[c] | n/d | 0.0000 |
| NS-3 | 1a (34) | 0.0699 | | | | |
| | 1b (3) | 0.2270 | 0.0535 | | | |
| | 3 (4) | 0.3689 | 0.4279 | n/d | n/d | 0.0460 |
| NS-5 | 1 a (4) | 0.0743 | | | | |
| | 1b (7) | 0.2477 | 0.0372 | | | |
| | 2a (2) | 0.6092 | 0.6206 | 0.0612 | | |
| | 2b (3) | 0.5214 | 0.5732 | 0.2252 | 0.0655 | |
| | 3 (4) | 0.4754 | 0.4890 | 0.5983 | 0.5299 | 0.0322 |

[a]number of sequences analysed
[b]n/a: not applicable
[c]n/d: not done

II. Serological Reactivity of Blood Donors Infected with Three Different Types of Hepatitis C Virus HCV sequences were amplified in the 5' non-coding region (5'NCR), core, NS-3 and NS-5 regions from blood donors, hemophiliacs and intravenous drug abusers.

Blood donations that were repeatedly reactive on screening with Abbott 2nd generation enzyme immunoassay (EIA) and positive or indeterminate by Ortho recombinant immunoblot assay (RIBA) were amplified by primers in the 5'NCR (ref 10). The first fourteen PCR-positive blood donations (where PCR was used to amplify and thus detect HCV RNA present in the blood) were then typed by sequence analysis of the amplified region, and compared with their serological reactivity to a range of structural and non-structural peptides in two 1st generation EIAs (Ortho HCV ELISA; Abbott HCV EIA) and two RIBA assays (Ortho RIBA and Innogenetics LIA; Table 4). The five donations containing HCV type 1 sequences were positive in both EIAS, reacted with all antigens in the Ortho RIBA assay, and were broadly reactive in the LIA. However, all but two of the sera from donors with type 2 and 3 infections were completely negative an anti-C100 EIA screening and failed to react with 5-1-1, C100 (RIBA) and NS4 (LIA).

Furthermore, some carriers of HCV type 3 variants reacted poorly with the C33 (NS-3) peptide in the Ortho RIBA, and yielded two "indeterminate" results (donor nos. 11 and 13).

Thus, current tests using Ortho RIBA and (to a lesser extent) Innogenetics LIA tests are unable to reliably detect HCV-2 and HCV-3 genotypes. For reliable testing for all HCV types, antigens from 5-1-1, C100 and NS4 for each of the three types of HCV should preferably be included in the panel of antigens.

sequences yielded an uninterrupted consensus amino acid sequence that was used to define a series of overlapping oligopeptides for epitope mapping.

Epitope mapping and determination of antibody specificities. Overlapping synthetic peptides were synthesized on polypropylene pins using kits commercially available from Cambridge Research Biochemicals Ltd. The principle of the addition reactions is described in refs (Geysen et al., 1984; Geysen et al., 1985). Antibody reactions were carried out on pins disrupted by sonication (30 minutes) in 1% sodium dodecyl sulphate, 0.1% 2-mercaptoethanol, 0.1 M sodium dihydrogen orthophosphate. Pins were pre-coated in 1%

TABLE 4

SEROLOGICAL REACTIVITY OF SERA FROM BLOOD DONORS INFECTED WITH THREE TYPES OF HEPATITIS C VIRUS

| Donor Number | HCV genotype | Anti C100 0 | A† | Ortho RIBA 5-1-1 | C100 | C33 | C22 | Innogenetics LIA NS4 | NS5 | C1 | C2 | C3 | C4 |
|---|---|---|---|---|---|---|---|---|---|---|---|---|---|
| E-b13 | 1 | + | + | 3§ | 4 | 4 | 4 | 2§ | 3 | 1 | 2 | 1 | 1 |
| E-b15 | | + | + | 4 | 4 | 4 | 4 | 2 | 3 | 3 | 2 | 2 | 1 |
| E-b16 | | + | + | 4 | 4 | 4 | 4 | 2 | 3 | 2 | 3 | 3 | – |
| E-b17 | | + | + | 4 | 4 | 4 | 4 | 3 | 3 | 3 | 2 | 1 | 1 |
| E-b18 | | + | + | 4 | 4 | 4 | 4 | 3 | – | 2 | 1 | 1 | – |
| E-b9 | 2 | + | + | – | 1 | 3 | 4 | – | – | 3 | 1 | 1 | 3 |
| E-b10 | | – | – | – | – | 4 | 4 | – | 3 | 2 | 2 | 2 | – |
| E-b11 | | – | – | – | – | 4 | 4 | – | 3 | 4 | 2 | 2 | 3 |
| E-b12 | | – | – | – | – | 4 | 4 | – | 1 | 3 | 1 | 2 | 2 |
| E-b1 | 3 | – | – | – | – | – | 4 | – | 1 | 3 | 1 | – | 3 |
| E-b2 | | – | – | – | – | 4 | 4 | – | 2 | 1 | 1 | 1 | 2 |
| E-b3 | | + | + | – | – | 2 | 4 | 2 | 2 | 1 | 2 | 2 | 1 |
| E-b5 | | – | – | – | – | 2 | 4 | – | – | 3 | 1 | 2 | 3 |
| E-b7 | | – | – | – | – | – | 4 | – | 2 | 3 | 1 | 1 | 4 |

*Ortho HCV ELISA (Recombinant C100-3)
†Abbott HCV EIA (Hepatitis C Recombinant DNA Antigen)
‡Core oligopeptides. 1-4
§Bands scored – (negative) to 4 (strong-positive) according to manufacturers instructions.

III. Mapping of Antigenic Determinants in NS-4

Introduction

With an overall aim of improving serological screening assays, we have obtained sequence data from the antigenic region of region corresponding to c100-3 for types 2 and 3. This information was used to epitope map the region, to define additional immunoreactive peptides that could be used to improve serological anti-HCV assays.

Methods

PCR and sequencing. Plasma samples from Scottish blood donors yielding repeatedly reactive donations on 2nd generation anti-HCV screening (Abbott or Ortho), and which were confirmed or indeterminate on confirmatory testing by RIBA (Chiron) were referred to the Department of Medical Microbiology from the Scottish National Blood Transfusion Service Microbiology Reference Laboratory. HCV RNA within the plasma samples was extracted and amplified with primers in the 5'NCR as described previously (Chan et al., 1992). HCV was typed by sequence analysis of the amplified DNA as described previously (Simmonds et al., 1990) and by RFLP analysis.

Five samples from different donors infected with HCV type 3 (nos. 40, 38, 36, 26 and 1787), four infected with type 2 (nos. 31, 59, 940 and 810) and five with type 1 infection (nos. 16, 42, 77, 1801 and 1825) were amplified with primers corresponding to sense and anti-sense sequences (SEQ ID NO:32 through 39) spanning the antigenic region of NS-4 (Table 1). Nucleotide sequences obtained from the amplified DNA were compared and used to define consensus sequences for each HCV type. In-frame translation of the nucleotide ovalbumin, 1% bovine serum albumin, 0.1% Tween-20 in phosphate buffered saline (PBS) for one hour at room temperature. Serum or plasma was diluted 1.40 in PBS+0.1% Tween-20 (PBST) and incubated with the blocked pins at 4° C. for 18 hours. After washing in 4 changes of PBST (10 minutes at room temperature, with agitation), bound antibody was detected by incubation in a 1/20000 dilution of affinity isolated anti-human IgG, peroxidase conjugate (Sigma) for one hour at room temperature. Following washing (4 changes in PBST), pins were incubated in a 0.05% solution of azino-di-3-ethyl-benzthiazodinsulphonate in 0.1 M sodium phosphate/sodium citrate buffer (pH 4.0) containing 0.03% hydrogen peroxide for 20 minutes. Optical densities were read at 410 nm.

Results

HCV RNA in plasma samples from five donors infected with HCV type 3 by sequence analysis of the 5'NCR, and by RFLP were amplified in the NS-4 region using primers (SEQ ID NO:32 through 39) listed in Table 1. Because of the high degree of sequence variability in this region, it was necessary to use separate sense primers (SEQ ID NO:34 through 39) for the amplification of different HCV types. However, the antisense primers (SEQ ID NO:32 and 33) were in a highly conserved region and could be used for amplification of all three types. Sequence analysis was carried out as previously described. This gave a continuous sequence from position 4911 to 5271 (numbered as in Choo et al., 1991) (HCV-3— SEQ ID NO:16) (FIG. 9A Little sequence variability (highlighted) was observed between the four different donors in this region.

The nucleotide sequences were used to deduce the sequence of the encoded peptide (FIG. 9B). The putative protein contains mainly hydrophilic residues but no potential sites for N-linked glycosylation. Amino acid sequence variability with HCV type 3 was confined to only five residues (SEQ ID NO:17) (FIG. 9B. However, this region differed considerably from the amino acid sequences of other blood donors infected with HCV types 1 and 2 (T16, 42, 77, 1801, 1825, 351, 940 and 810; FIG. 10A). Sequence comparison between the major HCV types from residues 1679 to 1769 reveals three regions of considerable amino acid sequence variability. Most of the observed differences between types involve non-synonymous amino acid substitutions, particularly alternation of acidic and basic residues in the hydrophilic regions. These changes would be expected to profoundly alter the overall conformation of the protein, and its antigenicity.

The consensus amino acid sequences in this region of types 1, 2 and 3 (SEQ ID NO:17) (FIG. 10B) were used to define three series of 82 nonameric oligopeptides (spanning residues 42 to 128 of (SEQ ID NO:17) overlapping by eight of the nine residues with those before and after in the series (FIG. 11A-C). These were synthesized on a 12×8 arrays of polypropylene pins as described in Methods. Antibody reactivity to the immobilized antigens on the pins was determined by indirect ELISA using an overnight incubation with a 1/40 dilution of test serum overnight at 4° C., followed by washing, and detection with an anti-human IgG-peroxidase conjugate and appropriate substrate (see Methods).

Reactivity of an anti-HCV negative, PCR-negative donor, with no known risk factors for HCV infection with the three series of peptides was determined. No significant reactivity is shown with any of the HCV-encoded oligopeptides. Reactivity of sera from three donors infected with HCV type 3 (derived from residues 42 to 128 of SEQ ID NO:17) to each of the oligopeptides is shown in FIGS. 12A-12C. All three sera reacted with peptides ranging from No. 13 (sequence KPALVPDKE amino acids 54 to 62 in (SEQ ID NO:17; FIG. 7) to No. 22 (sequence VLYQQYDEM; residues 63 to 71 in SEQ ID NO:17) in the first antigenic region, although the precise peptides recognized varied slightly between individuals. All three sera reacted to varying extents with a second antigenic region, lying in the range from oligopeptides 32 to 42 (of sequence ECSQAAPYI, residues 73 to 81 of SEQ ID NO:17, to QAQVIAHQF, residues 83 to 91 of SEQ ID NO:17). Weaker and more variable reactivity was observed to peptides 48 (residues 88 to 96 of SEQ ID NO:17) to 53 (residues 94 to 102 of SEQ ID NO:17). Finally, significant reactivity was also observed to single oligonucleotides 2 (residues 43 to 51 of SEQ ID NO:17) (2 of 3 samples), 61 (residues 102-110 of SEQ ID NO:17) (2 of 3), 66 (residues 107 to 115 of SEQ ID NO:17) (3 of 3), 73 (residues 114 to 122 of SEQ ID NO:17) (3 of 3) and 80 (residues 121 to 129 of SEQ ID NO:17) (2 of 3).

The sequences of the major antigenic regions of HCV type 3 differ considerably from those encoded by any of the type 1 or type 2 variants. The region bounded by peptides 13 to 22 (SEQ ID NO:1) shows average homologies of 50% with HCV type 2 (SEQ ID NO:3 and 4) variants and 67% with type 1 (SEQ ID NO:7 and 8). Between peptides 32 to 42 (SEQ ID NO:2), there are homologies of 39% with type 2 (SEQ ID NO:5 and 6) and 58% with type 1 (SEQ ID NO:10 and 11) variants. Thus, although similar regions of each NS-4 sequence are antigenic, the actual epitopes differ considerably between HCV types.

Discussion

The NS-4 region of HCV type 3 (SEQ ID NO:16 and 17) shows considerable sequence divergence from other variants of HCV, that exceeds that found in the core, NS-3 or NS-5 regions previously analyzed (Chan et al., 1992). The function of the protein encoded by this region of the HCV genome is unknown, and the consequences of this variability on virus replication and pathogenesis are unknown. The function of the NS-4 region in flaviviruses and pestiviruses is also poorly defined.

The degree of amino acid sequence variability, and the nature of the amino acid substitutions indicate that the major sites of antibody reactivity are also those of antigenic variability. This undoubtedly underlies the restricted cross-reactivity of HCV type 1 NS-4 encoded antigens with sera from individuals infected with different HCV types. Serological diagnosis of infection is currently based entirely on recombinant or synthetic oligopeptide sequences derived ultimately from HCV type 1 sequences (Choo et al., 1991). The serological response to infection is often very restricted in its initial stages, with antibody to only one of the recombinant antigens used for screening. Not only does this present difficulties with supplementary antibody tests, where reactivity to two HCV-encoded antigens is required for confirmation, but can lead to an increased probability of failing to detect early infection with HCV types 2 and 3.

Table 7 relates HCV typing determined by PCR, using type-specific sense primers (SEQ ID NO:44 through 49) and the nontype-specific anti-sense primers (SEQ ID NO:22 and 23) (Table 6), to results obtained using type-specific antigens (TSA) and shows good correlation for HCV1-3 types.

TABLE 5

SEQUENCES OF NS-4 ENCODED ANTIGENS FOR (A) IMPROVED SEROLOGICAL DIAGNOSIS. AND (B) FOR SEROLOGICAL DISCRIMINATION OF INFECTION WITH DIFFERENT HCV TYPES

| Type | Region 1 (1691-1708)* | Region 2 (1710-1728) |
|---|---|---|
| A) | | |
| 3 | KPALVPDKEVLYQQYDEM† (SEQ ID NO: 1) | ECSQAAPYIEQAQVIAHQF (SEQ ID NO: 2) |
| 2‡ | RVVVTPDKEILYEAFDEM (SEQ ID NO: 3) | ECASKAALIFEGQRMAEML (SEQ ID NO: 5) |
| | RAVIAPDKEVLYEAFDEM (SEQ ID NO: 4) | ECASRAALIEEGQRIAEL (SEQ ID NO: 6) |
| B) | | |
| 3 | KPALVPDKEVLYQQYDEM (SEQ ID NO: 1) | ECSQAAPYIEQAQVIAHQF (SEQ ID NO: 2) |
| 2 | RVVVTPDKEILYEAFDEM (SEQ ID NO: 3) | ECASKAALIEEGQRMAEML (SEQ ID NO: 5) |
| | RAVIAPDKEVLYEAFDEM (SEQ ID NO: 4) | ECASRAALIIEEGQRIAEML (SEQ ID NO: 6) |

TABLE 5-continued

SEQUENCES OF NS-4 ENCODED ANTIGENS FOR (A) IMPROVED
SEROLOGICAL DIAGNOSIS. AND (B) FOR SEROLOGICAL
DISCRIMINATION OF INFECTION WITH DIFFERENT HCV TYPES

| Type | Region 1 (1691-1708)* | Region 2 (1710-1728) |
|---|---|---|
| 1 | KPAIIPDREVLYREFDEM (SEQ ID NO: 7) | ECSQHLPYIEGMLAEQF (SEQ ID NO: 10) |
|   | KPAVIPDREVLYREFDEM (SEQ ID NO: 8) | ECSQHLPYIEGALAEQF (SEQ ID NO: 11) |

*Amino acrid positions numbered as in Choo et al., (1991).
†Amino acid codes: A: alanine. R: arginine: N: asparagine. D: aspartic acid: C: cysteine: Q: glutamine: E: glutamic acid: G: glycine: H: histidine: I: isoleucine: L: leucine: K: lysine: M: methionine: F: phenylalanine: P: proline: S: serine: T threonine. W: tryptophan. Y: tyrosine: V: valine.
‡T Alternative peptides. where there is variability within an HCV type.

TABLE 6

SEQUENCES OF OLIGONUCLEOTIDES SUITABLE FOR DIRECT DETECTION OF
HCV TYPE 3 IN CLINICAL SPECIMENS BY POLYMERASE CHAIN REACTION

| Name | Region | Position of 5'base* | Pol.† | Sequences 5'-3'‡ |
|---|---|---|---|---|
| 007 | NS-4 | 5293 | − | AACTCGAGTATCCCACTGATGAAGTTCCACAT (SEQ ID NO: 32) |
| 220 | NS-4 | 5278 | − | CACATGTGCTTCGCCCAGAA (SEQ ID NO: 33) |
| Type 3¶ | | | | |
| TS-3a | NS-4 | 5140 | + | GCCGCCCCATATATCGAACA (SEQ ID NO: 44) |
| TS-3b | NS-4 | 5161 | + | GCTCAGGTAATAGCCCACCA (SEQ ID NO: 45) |
| Type 2: | | | | |
| TS-2a | NS-4 | 5140 | + | AAAGCCGCCCTCATTGAGGA (SEQ ID NO: 46) |
| TS-2b | NS-4 | 5161 | + | GGGCAGCGGATGGCGGAGAT (SEQ ID NO: 47) |
| Type 1: | | | | |
| Type 1: TS-1a | NS-4 | 5140 | + | CACTTACCGTACATCGAGCA (SEQ ID NO: 48) |
| TS-1b | NS-4 | 5161 | + | GGGATGATGCTCGCCGAGCA (SEQ ID NO: 49) |

*Position of 5' base relative to HCV genomic sequence in Choo et al. (1991).
†Orientation of primer sequence (+: sense: −: anti-sense)
‡Abbreviations: A: adenine. C: cytidine: G: guanidine. T: thymidine.
¶Type-specific sense primers for amplification of HCV types 3, 2 and 1 variants.

TABLE 7

COMPARISON OF SEROLOGICAL
TYPING BY HCV-TSA WITH PCR

| PCR[a] | Number tested | TYPE-SPECIFIC ANTIBODY | | | | | | | |
|---|---|---|---|---|---|---|---|---|---|
| | | 1 | 2 | 3 | 1 + 2 | 1 + 3 | 2 + 3 | NTS[b] | NR[c] |
| 1 | 57 | 63 | — | — | — | 1 | — | 3 | 3 |
| 2 | 12 | — | 11 | — | — | — | 1 | 1 | 0 |
| 3 | 47 | 1 | — | 45 | — | 2 | — | 4 | 4 |
| Hem[d] | 27 | 11 | — | 4 | 1 | 4 | — | 3 | 4 |

[a]"Genotype of HCV sequences amplified by PCR and typed by RFLP (McOmish et al. 1992)
[b]NTS: No type-specific antibody detected
[c]NR: non-reactive with NS-4 peptides
[d]Samples from HCV-infected hemophiliacs un-typed by PCR.

IV. Identification of HCV Type-4
Introduction

Investigations were carried out on sequence variations in the 5' non-coding region (5'NCR) of HCV samples from a variety of worldwide geographical locations (FIG. 13), and also in the core region (FIGS. 15A and 15B). Phylogenetic analysis (FIGS. 14 and 16) revealed a new distinct HCV type which we refer to herein as HCV-4.

Methods

Samples. RNA was extracted from plasma samples that were repeatedly reactive on second generation screening assays for HCV, and which were either confirmed (significant reactivity with two or more antigens in the Chiron recombinant immunoblot assay; Chiron Corporation, Emeryville, Calif., USA) or indeterminate (reactive with only one antigen) from blood donors and patients with NANBH. Most of the samples containing sequences that differed substantially fcm known HCV types came from Egypt (EG 1-33). Others came from Holland (NL-26), Hong Kong (HK 1-4), Iraq (IQ-48) and XX (xx-(6).

Sequence determination. HCV sequences were reverse transcribed and amplified with primers matching conserved regions in the 5'NCR as previously described (1). For analysis of the core region, RNA was reverse transcribed using a primer of sequence CA(T/C)GT(A/G)AGGGTATCGAT-GAC (SEQ ID NO:50) (5' base: xxx, numbered as in [20]). cDNA was amplified using this primer and a primer in the 5'NCR of sequence ACTGCCTGATAGGGTGCTTGCGAG (SEQ ID NO:51) (5' base: −54). The second PCR used primers of sequences AGGTCTCGTAGACCGTGCATCATG (SEQ ID NO:52) (5' base: −21) and TTGCG(G/T/C)GACCT (A/T)CGCCGGGGGTC (SEQ ID NO:53) (5' base: xxx). Amplified DNA in both regions was directly sequenced as described previously (ref 1a).

Sequence analysis. Sequences were aligned using the CLUSTAL program in the University of Wisconsin GCG package (ref. 6). Phylogenetic trees were constructed by the DNAML program in the PHYLIP package of Felsenstein (version 3.4, June 1991; (ref 9), using the global option. RNA secondary structures in the 5'NCR of 4 representative HCV variants (refs) were predicted using the program FOLD. Three predictions were made from each sequence between nucleotides −341 to −1, −341 to +300, and −341 to +900 to allow for possible long range interactions. Comparison of the predicted conformations for each sequence over the different lengths showed that only relatively small scale features, such as the stem/loop analyzed in the results were at all conserved (data not shown).

All sequences reported in this part have been submitted to GenBank.

Results

Divergent 5'NCR sequences (SEQ ID NO:58). Several sequences in the 5'NC region detected in samples of blood donors from Saudi Arabia, Holland and Hong Kong, and from NANBH patients in Iraq and xxx differed substantially from those found in Scottish blood donors—and those reported elsewhere (FIG. 13). Instead of showing the well characterized nucleotide substitutions that distinguish HCV types 1, 2 and 3 from each other, a new set of sequence differences were observed in the new variants that appeared to place them outside the existing system of virus classification. This can be more simply represented by reconstructing a phylogeny of the sequences and presenting the results as an evolutionary tree (FIG. 14). This analysis confirms that sequences 1-10 cluster separately from the variants previously typed as 1, 2 and 3 (SEQ ID NO:12). For convenience we will refer to sequences within this new group as HCV type 4 (SEQ ID NO:18). Mean distances within type 4 and between type 4 and the other HCV types in the 5'NCR were comparable to those previously described for type 1-3. Although sequences within type 4 (SEQ ID NO:18) are relatively closely grouped, sequences 11, 12 and 13 differ considerably from any of the known types.

Using this phylogenetic tree, it can be seen that the majority of previously published 5'NCR sequences can be readily identified as types 1, 2 or 3 (SEQ ID NO:12). Furthermore, almost all of the sequences from Zaire (shown as hollow squares) cluster closely within type 4, suggesting a wider distribution in Africa. However, a further complication is that three identical sequences obtained from South African patients appeared distinct from both the type 1 and the type 4 (SEQ ID NO:18) group, and may represent yet another HCV type.

RNA from three representative type 4 variants (Eg 29, 33, 21; corresponding to 5'NCR sequences nos. 1-3) was amplified using primers in the core region of HCV polyprotein. All three sequences differed considerably at both the nucleotide (SEQ ID NO:20) and amino acid (SEQ ID NO:21) level from HCV types 1, 2 and 3 (SEQ ID NO:19 and residues 1 to 89 of SEQ ID NO:15, respectively) (FIGS. 15A/B). Phylogenetic analysis of these sequences and those previously analyzed indicated that they formed a separate, relatively homogeneous group distinct from the other types (FIG. 16). Reconstructed nucleotide distances between type 4 (SEQ ID NO:20) and types 1, 2 and 3 (SEQ ID NO:19) were comparable to those that exist between the three known HCV types of HCV. Although most of the nucleotide sequence differences were silent, there were between 4 and 9 amino acid differences between the new variants (SEQ ID NO:21) and other types.

V. HCV Typing

Introduction

In view of the sequence variations between HCV types 1, 2, 3 and 4, differences in restriction enzyme cleavage sites exist, leading to different endonuclease cleavage patterns. This technique was used to identify HCV genotypes in blood samples from a variety of sources worldwide.

(A) Typing of HCV1-3

Methods

Serum Samples. Samples from blood donors in six countries, Scotland, Finland, Netherlands, Hong Kong and Australia and Japan, were available from routine 2nd Generation anti-HCV ELISA screening (Ortho or Abbott). Donor samples that were repeatedly reactive in the above tests were further investigated using a supplementary test (Ortho RIBA: Finland, Netherlands, Australia, Egypt, Abbott Matrix: Hong Kong) or samples were titered for anti-HCV by ELISA (Japan). Samples that were positive (significant reactivity with two or more HCV antigens (1+ to 4+) or indeterminate (reactivity with one antigen only) in the RIBA test or had a titer of >X 4096 by ELISA (Japan only) were tested for viral RNA by Polymerase Chain Reaction (PCR).

RNA PCR: PCR for the detection of HCV RNA was carried out as previously described by Chan et al. (ref 1a) using primers in the 5' non-coding region (5'NCR) in a nested PCR, with primers 209 (SEQ ID NO:22)/939 (SEQ ID NO:24) and 211 (SEQ ID NO:23)/940 (SEQ ID NO:25) in first and second reactions respectively.

HCV TYPING. The existence of relatively conserved patterns of substitutions in the 5'NCR that are characteristic of different HCV types provide useful signature sequences for identification of HCV genotypes. Having compared large numbers of different HCV type 1, 2 and 3 sequences, we developed a method that differentiated HCV types 1-3 by restriction endonuclease cleavage of amplified DNA. However, the 19 type 4 sequences would appear as type 1 (electrophoretic types Aa and Ab), and for concurrent studies it has been necessary to modify the conditions to identify the new HCV type. All type 4 sequences showed a T→C change at position −167 (position 78 in SEQ ID NO:18) that creates a novel Hinf1 site that is absent in all type 1 (and type 2) sequences. In combination with ScrFI, and HaeIII/RsaI, it has now proved possible to identify the new type reliably in numerous countries in the Middle East and elsewhere.

Results

The results are summarized in Table 8 for HCV types 1, 2 and 3. The Egyptian samples gave aberrant restriction patterns on the single ScrFI digest and were identified as type 4.

TABLE 8

PREVALENCE OF HCV TYPES IN DIFFERENT COUNTRIES

| COUNTRY | HCV TYPES (%) | | |
| --- | --- | --- | --- |
| | HCV-1 | HCV-2 | HCV-3 |
| Scotland | 86 (51%) | 21 (13%) | 60 (36%) |
| Finland | 3 (25%) | 5 (42%) | 4 (33%) |
| Netherlands | 18 (60%) | 7 (23%) | 5 (17%) |
| Hong Kong | 22 (63%) | 0 (0%) | 0 (0%) |
| Australia | 13 (57%) | 3 (13%) | 7 (30%) |
| Japan | 31 (77%) | 9 (23%) | 0 (0%) |
| Egypt | 0 (0%) | 0 (0%) | 0 (0%) |

(B) Modification of PCR-Based Typing Assay to Detect Infection with HCV Type 4 in Clinical Specimens
Methods Extraction of RNA. RNA was extracted from 100 µl aliquots of plasma of non-A, non-B patients by addition of 1 ml RNAzol solution (2M guanidinium thiocyanate, 12.5 mM sodium citrate [pH 7.0], 0.25% w/v N-lauroylsarcosine, 0.05 M 2-mercaptoethanol, 100 mM sodium acetate [pH 4.0], 50% w/v water saturated phenol) as previously described (Chomczynski et al. 1987), and mixed until precipitate dissolved. After addition of 100 µl chloroform, each sample was spun for 5 minutes at 14000×g and the aqueous phase re-extracted with 0.5 ml chloroform. RNA was precipitated by addition of an equal volume of isopropanol and incubation at −20° C. for at least 1 hour. An RNA pellet was produced by centrifugation at 14000×g for 15 minutes at 4° C., washed in 1 ml 70% cold ethanol solution, dried and resuspended in 20 µl diethylpyrocarbonate treated distilled water. Of the 100 directly extracted samples, a total of 19 were PCR-negative (see below). Two ml volumes of the negative samples were ultracentrifuged at 200000×g for 2 hours and the pellet re-extracted as described above. Extraction from the larger volume of plasma yielded an additional 3 positive samples (numbers 66, 80, 85).

PCR and typing. RNA was reverse transcribed with primer 940 (SEQ ID NO:25) and cDNA amplified in a two stage nested PCR reaction with primers 940 (SEQ ID NO:25)/939 (SEQ ID NO:24), followed by 209 (SEQ ID NO:22)/211 (SEQ ID NO:23) as previously described (Chan et al. 1992). PCR product was radiolabeled with [$^{35}$S]-dATP analyzed by restriction endonuclease cleavage (McOmish et al. *Transfusion*, 32:no. 11 1992). Samples were cleaved with ScrFI and a combination of HaeIII/RsaI in two separate reactions to identify HCV types 1/4, 2, 3. FIG. 17 shows endonuclease cleavage patterns. HCV types 1 and 4 were differentiated by a third reaction with Hinfl (see Results). Two samples yielded restriction patterns that were different from those of the four known types of HCV and were analyzed further by direct sequence analysis of the amplified DNA (Chan et al. 1992). These two samples contained 5'NCR sequences distinct from those of known HCV types and currently remain unclassified.

Results

Modification of RFLP method to identify HCV type 4. Previous sequence analysis in the 5'NCR of HCV amplified from plasma of Egyptian blood donors revealed a relatively homogeneous group of novel sequence variants in both the 5'NCR (SEQ ID NO:18) and core (SEQ ID NO:20 and 21) region which were as distinct from HCV types 1, 2 and 3 (SEQ ID NO:19 and residues 1 to 89 of SEQ ID NO:15 as these latter types were from each other (see previous submission). This new group was designated as HCV type 4.

Comparison of cleavage patterns of type 4 sequences with those of type RFLP analysis of the previously identified type 4 sequences produced a distribution of electropherotypes with ScrFI and HaeIII/RsaI similar to that HCV type 1 (Table 9). Type 1 sequences yielded 9 patterns of aA/B, 35 of bA/B and 1 bC. With these enzymes alone, type 4 sequences were thus indistinguishable from type 1 (14 aA/B, 4 bA/B). However, type 1 and type 4 sequences consistently differ in the number of Hinfl sites. All 18 type 4 sequences contain one or two potential cleavage sites (producing patterns band c; Table 5) while none are found in any of the 45 type 1 sequences analyzed (pattern a). One of the type 4 sequences was further differentiated from type 1 and other HCV types by the loss of a restriction site for RsaI, leading to a new pattern of bands designated h (44, 172, 9, 26; first column, Table 9). Finally, a single sequence, EG-28 lost two sites to produce bands of 216, 9, and 26 bps (pattern i; Table 9). This sequence was distinct from that of any of the known HCV types (including type 4) and is shown in the table in the column labelled U (unclassified)

Typing of study subjects. RNA was extracted from 100 samples of patients with NANB hepatitis and amplified with primers in the 5'NCR. Of these, 84 were PCR positive, and enabled HCV typing to be carried out by RFLP. This was initially carried out with HaeIII/RsaI and ScrFl, and allowed the identification of 10 type 2 and 10 type 3 variants (Table 10). Samples showing electrophoretic patterns aA/B or bA/B were further analyzed by cleavage with Hinfl, yielding 38 samples with pattern a, thus identified as type 1, 22 with pattern b and 2 with pattern c, both identified as type 4. Finally, two samples showed the unusual cleavage patterns h and i with HaeII/RsaI and pattern b with Hinfl, and were therefore directly sequenced. These two sequences were similar to each other but were unlike any of the known HCV types, and also distinct from EG-28, the other sequence showing pattern i with HaeIII/RsaI (Table 10). As they cannot be currently classified, they will be referred to as type U.

TABLE 9

PREDICTED CLEAVAGE PATTERNS OF PUBLISHED 5'NCR SEQUENCES OF HCV TYPES 1, 2, 3 AND 4 WITH RsaI/HaeIII, ScrFI AND Hinfl

| Predicted cleavage pattern[a] | | | HCV type | | | | |
|---|---|---|---|---|---|---|---|
| HaeIII/RsaI | ScrFI | Hinfl | 1 | 2 | 3 | 4 | U[b] |
| a | A/B | a[c] | 9 | — | — | — | — |
| b | A/B | a | 35 | — | — | — | — |
| b | C | a | 1 | — | — | — | — |
| a | A/B | b[d] | — | — | — | 13 | — |
| a | A/B | c[e] | — | — | — | 1 | — |
| b | A/B | b | — | — | — | 4 | — |
| c | D | a | — | 5 | — | — | — |
| d | D | a | — | 1 | — | — | — |
| d | E | a | — | 2 | — | — | — |
| e | D | a | — | 1 | — | — | — |
| e | E | a | — | 1 | — | — | — |
| f | G | b | — | — | 14 | — | 1 |
| f | G | c | — | — | 1 | — | — |
| g | G | b | — | — | 8 | — | — |
| h[f] | A/B | b | — | — | — | 1 | — |
| i[g] | A/B | b | — | — | — | — | — |

[a]Cleavage patterns designated for HaeIII/RsaI and ScrFI as described previously (McOmish et al. 1992).
[b]Cleavage pattern of an HCV variant of undesigned type
[c]Pattern a: uncleaved by Hinfl
[d]Pattern b: DNA cleaved to generate two fragments of sizes 107 and 142 bps (in order 5' → 3')
[e]Pattern c: DNA cleaved to generate three fragments of 56, 51 and 142 bps
[f]New cleavage pattern for HaeIII/RsaI designated h (bands of 44 bps, 172 bps, 9 bps, 26 bps)
[g]New cleavage pattern for HaeIII/RsaI designated i (216 bps, 9 bps, 26 bps)

TABLE 10

IDENTIFICATION OF HCV TYPES 1-4 IN STUDY SUBJECTS BY RFLP ANALYSIS OF 5'NCR SEQUENCES WITH RsaI/HaeIII, ScrFI AND Hinfl

| Observed cleavage pattern | | | Inferred HCV type | | | | |
|---|---|---|---|---|---|---|---|
| HaeIII/RsaI | ScrFI | Hinfl | 1 | 2 | 3 | 4 | U[a] |
| a | A/B | a | 2 | — | — | — | — |
| b | A/B | a | 36 | — | — | — | — |
| a | A/B | b | — | — | — | 16 | — |
| a | A/B | c | — | — | — | 2 | — |
| b | A/B | b | — | — | — | 6 | — |
| c | D | n.d. | — | 7 | — | — | — |
| d | E | n.d. | — | 3 | — | — | — |

TABLE 10-continued

IDENTIFICATION OF HCV TYPES 1-4 IN STUDY SUBJECTS
BY RFLP ANALYSIS OF 5'NCR SEQUENCES WITH
RsaI/HaeIII, ScrFI AND HinfI

| Observed cleavage pattern | | | Inferred HCV type | | | | |
|---|---|---|---|---|---|---|---|
| HaeIII/RsaI | ScrFI | HinfI | 1 | 2 | 3 | 4 | U[a] |
| f | G | n.d. | — | — | 7 | — | — |
| g | G | n.d. | — | — | 3 | — | — |
| h | A/B | b | — | — | — | — | 1 |
| i | A/B | b | — | — | — | — | 1 |
| TOTALS | | | 38 | 10 | 10 | 24 | 2 |

[a]Two samples yielded unusual restriction patterns with HaeIII/RsaI (h. i). Sequence analysis of the 5'NCR placed them outside existing HCV classification (samples IQ-48, EG-96).

VI. Expression and Assay Etc. Techniques

The present invention also provides expression vectors containing the DNA sequences as herein defined, which vectors being capable, in an appropriate host, of expressing the DNA sequence to produce the peptides as defined herein.

The expression vector normally contains control elements of DNA that effect expression of the DNA sequence in an appropriate host. These elements may vary according to the host but usually include a promoter, ribosome binding site, translational start and stop sites, and a transcriptional termination site. Examples of such vectors include plasmids and viruses. Expression vectors of the present invention encompass both extrachromosomal vectors and vectors that are integrated into the host cell's chromosome. For use in *E. coli*, the expression vector may contain the DNA sequence of the present invention optionally as a fusion linked to either the 5'- or 3'-end of the DNA sequence encoding, for example, β-galactosidase or to the 3'-end of the DNA sequence encoding, for example, the trp E gene. For use in the insect baculovirus (AcNPV) system, the DNA sequence is optionally fused to the polyhedron coding sequence.

The present invention also provides a host cell transformed with expression vectors as herein defined.

Examples of host cells of use with the present invention include prokaryotic and eukaryotic cells, such as bacterial, yeast, mammalian and insect cells. Particular examples of such cells are *E. coli, S. cerevisiae, P. pastoris*. Chinese hamster ovary and mouse cells, and *Spodoptera frugiperda* and *Tricoplusia ni*. The choice of host cell may depend on a number of factors but, if post-translational modification of the HCV viral peptide is important, then an eukaryotic host would be preferred.

The present invention also provides a process for preparing a peptide as defined herein which comprises isolating the DNA sequence, as herein defined, from the HCV genome, or synthesizing DNA sequence encoding the peptides as defined herein, or generating a DNA sequence encoding the peptide, inserting the DNA sequence into an expression vector such that it is capable, in an appropriate host, of being expressed, transforming host cells with the expression vector, culturing the transformed host cells, and isolating the peptide.

The DNA sequence encoding the peptide may be synthesized using standard procedures (Gait, *Oligonucleotide Synthesis: A Practical Approach,* 1984, Oxford, IRL Press).

The desired DNA sequence obtained as described above may be inserted into an expression vector using known and standard techniques. The expression vector is normally cut using restriction enzymes and the DNA sequence inserted using blunt-end or staggered-end ligation. The cut is usually made at a restriction site in a convenient position in the expression vector such that, once inserted, the DNA sequences are under the control of the functional elements of DNA that effect its expression.

Transformation of a host cell may be carried out using standard techniques. Some phenotypic marker is usually employed to distinguish between the transformants that have successfully taken up the expression vector and those that have not. Culturing of the transformed host cell and isolation of the peptide as required may also be carried out using standard techniques.

The peptides of the present invention may be prepared by synthetic methods or by recombinant DNA technology. The peptides are preferably synthesized using automatic synthesizers.

Antibody specific to a peptide of the present invention can be raised using the peptide. The antibody may be polyclonal or monoclonal. The antibody may be used in quality control testing of batches of the peptides; purification of a peptide or viral lysate; epitope mapping; when labelled, as a conjugate in a competitive type assay, for antibody detection; and in antigen detection assays.

Polyclonal antibody against a peptide of the present invention may be obtained by injecting a peptide, optionally coupled to a carrier to promote an immune response, into a mammalian host, such as a mouse, rat, sheep or rabbit, and recovering the antibody thus produced. The peptide is generally administered in the form of an injectable formulation in which the peptide is admixed with a physiologically acceptable diluent. Adjuvants, such as Freund's complete adjuvant (FCA) or Freund's incomplete adjuvant (FIA), may be included in the formulation. The formulation is normally injected into the host over a suitable period of time, plasma samples being taken at appropriate intervals for assay for anti-HCV viral antibody. When an appropriate level of activity is obtained, the host is bled. Antibody is then extracted and purified from the blood plasma using standard procedures, for example, by protein A or ion-exchange chromatography.

Monoclonal antibody against a peptide of the present invention may be obtained by fusing cells of an immortalizing cell line with cells which produce antibody against the viral or topographically related peptide, and culturing the fused immortalized cell line. Typically, a non-human mammalian host, such as a mouse or rat, is inoculated with the peptide. After sufficient time has elapsed for the host to mount an antibody response, antibody producing cells, such as the splenocytes, are removed. Cells of an immortalizing cell line, such as a mouse or rat myeloma cell line, are fused with the antibody producing cells and the resulting fusions screened to identify a cell line, such as a hybridoma, that secretes the desired monoclonal antibody. The fused cell line may be cultured and the monoclonal antibody purified from the culture media in a similar manner to the purification of polyclonal antibody.

Diagnostic assays based upon the present invention may be used to determine the presence or absence of HCV infection. They may also be used to monitor treatment of such infection, for example in interferon therapy.

In an assay for the diagnosis of viral infection, there are basically three distinct approaches that can be adopted involving the detection of viral nucleic acid, viral antigen or viral antibody. Viral nucleic acid is generally regarded as the best indicator of the presence of the virus itself and would identify materials likely to be infectious. However, the detection of nucleic acid is not usually as straightforward as the detection of antigens or antibodies since the level of target can be very low. Viral antigen is used as a marker for the presence of virus and as an indicator of infectivity. Depending upon the virus, the amount of antigen present in a sample can be very low and difficult to detect. Antibody detection is relatively straightforward because, in effect, the host immune system is amplifying the response to an infection by producing large amounts of circulating antibody. The nature of the antibody response can often be clinically useful, for example IgM rather than IgG class antibodies are indicative of a recent infection, or the response to a particular viral antigen may be associated with clearance of the virus. Thus the exact approach adopted for the diagnosis of a viral infection depends upon the particular circumstances and the information sought. In the case of HCV, a diagnostic assay may embody any one of these three approaches.

In an assay for the diagnosis of HCV involving detection of viral nucleic acid, the method may comprise hybridizing viral RNA present in a test sample, or cDNA synthesized from such viral RNA, with a DNA sequence corresponding to the nucleotide sequences of the present invention or encoding a peptide of the invention, and screening the resulting nucleic acid hybrids to identify any HCV viral nucleic acid. The application of this method is usually restricted to a test sample of an appropriate tissue, such as a liver biopsy, in which the viral RNA is likely to be present at a high level. The DNA sequence corresponding to a nucleotide sequence of the present invention or encoding a peptide of the invention may take the form of an oligonucleotide or a cDNA sequence optionally contained within a plasmid. Screening of the nucleic acid hybrids is preferably carried out by using a labelled DNA sequence. Preferably the peptide of the present invention is part of an oligonucleotide wherein the label is situated at a sufficient distance from the peptide so that binding of the peptide to the viral nucleic acid is not interfered with by virtue of the label being too close to the binding site. One or more additional rounds of screening of one kind or another may be carried out to characterize further the hybrids and thus identify any HCV viral nucleic acid. The steps of hybridization and screening are carried out in accordance with procedures known in the art.

The present invention also provides a test kit for the detection of HCV viral nucleic acid, which comprises i) a labelled oligonucleotide comprising a DNA sequence of the present invention or encoding a peptide of the present invention; and ii) washing solutions, reaction buffers and a substrate, if the label is an enzyme.

Advantageously, the test kit also contains a positive control sample to facilitate in the identification of viral nucleic acid.

In an assay for the diagnosis of HCV involving detection of viral antigen or antibody, the method may comprise contacting a test sample with a peptide of the present invention or a polyclonal or monoclonal antibody against the peptide and determining whether there is any antigen-antibody binding contained within the test sample. For this purpose, a test kit may be provided comprising a peptide, as defined herein, or a polyclonal or monoclonal antibody thereto and means for determining whether there is any binding with antibody or antigen respectively contained in the test sample. The test sample may be taken from any of the appropriate tissues and physiological fluids mentioned above for the detection of viral nucleic acid. If a physiological fluid is obtained, it may optionally be concentrated for any viral antigen or antibody present.

A variety of assay formats may be employed. The peptide can be used to capture selectively antibody against HCV from solution, to label selectively the antibody already captured, or both to capture and label the antibody. In addition, the peptide may be used in a variety of homogeneous assay formats in which the antibody reactive with the peptide is detected in solution with no separation of phases.

The types of assay in which the peptide is used to capture antibody from solution involve immobilization of the peptide on to a solid surface. This surface should be capable of being washed in some way. Examples of suitable surfaces include polymers or various types (molded into microtiter wells; beads; dipsticks of various types; aspiration tips; electrodes; and optical devices), particles (for example latex; stabilized red blood cells; bacterial or fungal cells; snores; gold or other metallic or metal-containing sols; and proteinaceous colloids) with the usual size of the particle being from 0.02 to 5 microns, membranes (for example of nitrocellulose; paper; cellulose acetate; and high porosity/high surface area membranes of an organic or inorganic material).

The attachment of the peptide to the surface can be by passive adsorption from a solution of optimum composition which may include surfactants, solvents, salts and/or chaotropes; or by active chemical bonding. Active bonding may be through a variety of reactive or activatible functional groups which may be exposed on the surface (for example condensing agents; active acid esters, halides and anhydrides; amino, hydroxyl, or carboxyl groups; sulphydryl groups; carbonyl groups; diazo groups; or unsaturated groups). Optionally, the active bonding may be through a protein (itself attached to the surface passively or through active bonding), such as albumin or casein, to which the viral peptide may be chemically bonded by any of a variety of methods. The use of a protein in this way may confer advantages because of isoelectric point, charge, hydrophilicity or other physico-chemical property. The viral peptide may also be attached to the surface (usually but not necessarily a membrane) following electrophoretic separation of a reaction mixture, such as immunoprecipitation.

After contacting (reacting) the surface bearing the peptide with a test sample, allowing time for reaction, and, where necessary, removing the excess of the sample by any of a variety of means (such as washing, centrifugation, filtration, magnetism or capillary action), the captured antibody is detected by any means which will give a detectable signal. For example, this may be achieved by use of labelled molecule or particle as described above which will react with the captured antibody (for example protein A or protein G and the like; anti-species or anti-immunoglobulin-sub-type: rheumatoid factor: or antibody to the peptide, used in a competitive or blocking fashion), or any molecule containing an epitope contained in the peptide.

The detectable signal may be optical or radioactive or physico-chemical and may be provided directly by labelling the molecule or particle with, for example, a dye, radiolabel, electroactive species, magnetically resonant species or fluorophore, or indirectly by labelling the molecule or particle with an enzyme itself capable of giving rise to a measurable change of any sort. Alternatively the detectable signal may be obtained using, for example, agglutination, or through a diffraction or birefringent effect if the surface is in the form of particles.

Assays in which a peptide itself is used to label an already captured antibody require some form of labelling of the peptide which will allow it to be detected. The labelling may be direct by chemically or passively attaching for example a radiolabel, magnetic resonant species, particle or enzyme label to the peptide; or indirect by attaching any for of label to a molecule which will itself react with the peptide. The chemistry of bonding a label to the peptide can be directly through a moiety already present in the peptide, such as an amino group, or through an intermediate moiety, such as a maleimide group. Capture of the antibody may be on any of the surfaces already mentioned by any reagent including passive or activated adsorption which will result in specific antibody or immune complexes being bound. In particular, capture of the antibody could be by anti-species or anti-immunoglobulin-sub-type, by rheumatoid factor, proteins A, G and the like, or by any molecule containing an epitope contained in the peptide.

The labelled peptide may be used in a competitive binding fashion in which its binding to any specific molecule on any of the surfaces exemplified above is blocked by antigen in the sample. Alternatively, it may be used in a non-competitive fashion in which antigen in the sample is bound specifically or non-specifically to any of the surfaces above and is also bound to a specific bi- or poly-valent molecule (e.g. an antibody) with the remaining valencies being used to capture the labelled peptide.

Often in homogeneous assays the peptide and an antibody are separately labelled so that, when the antibody reacts with the recombinant peptide in free solution, the two labels interact to allow, for example, non-radiative transfer of energy captured by one label to the other label with appropriate detection of the excited second label or quenched first label (e.g. by fluorimetry, magnetic resonance or enzyme measurement). Addition of either viral peptide or antibody in a sample results in restriction of the interaction of the labelled pair and thus in a different level of signal in the detector.

A suitable assay format for detecting HCV antibody is the direct sandwich enzyme immunoassay (EIA) format. A peptide is coated onto microtiter wells. A test sample and a peptide to which an enzyme is coupled are added simultaneously. Any HCV antibody present in the test sample binds both to the peptide coating the well and to the enzyme-coupled peptide. Typically, the same peptide are used on both sides of the sandwich. After washing, bound enzyme is detected using a specific substrate involving a colour change. A test kit for use in such an EIA comprises: (1) a peptide, as herein defined labelled with an enzyme; (2) a substrate for the enzyme; (3) means providing a surface on which a peptide is immobilized; and (4) optionally, washing solutions and/or buffers.

It is also possible to use IgG/IgM antibody capture ELISA wherein an antihuman antibody is coated onto microtiter wells, a test sample is added to the well. Any IgG or IgM antibody present in the test sample will then bind to the anti-human antibody. A peptide of the present invention, which has been labelled, is added to the well and the peptide will bind to any IgG or IgM antibody which has resulted due to infection by HCV. The IgG or IgM antibody can be visualized by virtue of the label on the peptide.

It can thus be seen that the peptides of the present invention may be used for the detection of HCV infection in many formats, namely as free peptides, in assays including classic ELISA, competition ELISA, membrane bound EIA and immunoprecipitation. Peptide conjugates may be used in amplified assays and IgG/IgM antibody capture ELISA.

An assay of the present invention may be used, for example, for screening donated blood or for clinical purposes, for example, in the detection and monitoring of HCV infections. For screening purposes, the preferred assay formats are those that can be automated, in particular, the microtiter plate format and the bead format. For clinical purposes, in addition to such formats, those suitable for smaller-scale or for single use, for example, latex assays, may also be used. For confirmatory assays in screening procedures, antigens may be presented on a strip suitable for use in Western or other immunoblotting tests.

As indicated above, assays used currently to detect the presence of anti-HCV antibodies in test samples, particularly in screening donated blood, utilize antigenic peptides obtained from HIV type 1 only and, as demonstrated herein, such antigens do not reliably detect other HCV genotypes. Accordingly, it is clearly desirable to supplement testing for HIV-1 with testing for all other genotypes, for example, types 2, 3 and 4, and also any further genotypes that may be discovered.

To test for a spectrum of genotypes, there may be provided a series of assay means each comprising one or more antigenic peptides from one genotype of HCV, for example, a series of wells in a microtiter plate, or an equivalent series using the bead format. Such an assay format may be used to determine the genotype of HCV present in a sample. Alternatively, or in addition, an assay means may comprise antigenic peptides from more than one genotype, for example, a microwell or bead may be coated with peptides from more than one genotype.

It has been found advantageous to use more than one HCV antigen for testing, in particular, a combination comprising at least one antigenic peptide derived from the structural region of the genome and at least one antigenic peptide derived from the non-structural region, especially a combination of a core antigen and at least one antigen selected from the NS3, NS4 and NS5 regions. The wells or beads may be coated with the antigens individually. It has been found advantageous, however, to fuse two or more antigenic peptides as a single polypeptide, preferably as a recombinant fusion polypeptide. Advantages of such an approach are that the individual antigens can be combined in a fixed, predetermined ratio (usually equimolar) and that only a single polypeptide needs to be produced, purified and characterized. One or more such fusion polypeptides may be used in an assay, if desired in addition to one or more unfused peptides. It will be appreciated that there are many possible combinations of antigens in a fusion polypeptide, for example, a fusion polypeptide may comprise a desired range of antigens from one serotype only, or may comprise antigens from more than one serotype. The antigenic peptides from serotypes 2, 3 and 4 are preferably those described herein.

To obtain a polypeptide comprising multiple peptide antigens, it is preferred to fuse the individual coding sequences into a single open reading frame. The fusion should, of course, be carried out in such a manner that the antigenic activity of each component peptide is not significantly compromised by its position relative to another peptide. Particular regard should of course be had for the nature of the sequences at the actual junction between the peptides. The resulting coding sequence can be expressed, for example, as described above in relation to recombinant peptides in general. The methods by which such a fusion polypeptide can be obtained are known in the art, and the production of a recombinant fusion polypeptide comprising multiple antigens of a strain of HCV type 1 is described in GB-A-2 239 245 immunoprecipitation. Peptide conjugates may be used in amplified assays and IgG/IgM antibody capture ELISA.

The peptide of the present invention may be incorporated into a vaccine formulation for inducing immunity to HCV in man. For this purpose the peptide may be presented in association with a pharmaceutically acceptable carrier.

For use in a vaccine formulation, the peptide may optionally be presented as part of a hepatitis B core fusion particle, as described in Clarke et al. (*Nature*, 1987, 330, 381-384), or a polylysine based polymer, as described in Tam (*PNAS,*

1988, 85, 5409-5413). Alternatively, the peptide may optionally be attached to a particulate structure, such as liposomes or ISCOMS.

Pharmaceutically acceptable carriers include liquid media suitable for use as vehicles to introduce the peptide into a patient. An example of such liquid media is saline solution. The peptide may be dissolved or suspended as a solid in the carrier.

The vaccine formulation may also contain an adjuvant for stimulating the immune response and thereby enhancing the effect of the vaccine. Examples of adjuvants include aluminium hydroxide and aluminium phosphate.

The vaccine formulation may contain a final concentration of peptide in the range from 0.01 to 5 mg/ml, preferably from 0.03 to 2 mg/ml. The vaccine formulation may be incorporated into a sterile container, which is then sealed and stored at a low temperature, for example 4° C., or may be freeze-dried.

In order to induce immunity in man to HCV, one or more doses of the vaccine formulation may be administered. Each dose may be 0.1 to 2 ml, preferably 0.2 to 1 ml. A method for inducing immunity to HCV in man, comprises the administration of an effective amount of a vaccine formulation, as hereinbefore defined.

The present invention also provides the use of a peptide as herein defined in the preparation of a vaccine for use in the induction of immunity to HCV in man.

Vaccines of the present invention may be administered by any convenient method for the administration of vaccines including oral and parenteral (e.g. intravenous, subcutaneous or intramuscular) injection. The treatment may consist of a single dose of vaccine or a plurality of doses over a period of time.

LITERATURE CITED

1a. Chan, S. W., McOmish, F., Holmes, E C, Dow, B., Pentherer, J F, Follett, E., Yap, P L, and Simmonas, P. (1992). *J. Gen Virol:* 73:1131-1141.
1b. Chan, S. W., P. Simmonas, F. McOmish, P. L. Yap, R. Mitchell, B. Dow, and E. Follett. 1991. Serological reactivity of blood donors infected with three different types of hepatitis C virus. *Lancet* 338: 1391.
2. Chomczynski, P. and N. Sacchi. 1987. Single-step method of RNA isolation by acid guanidinium thiocyanate-phenol-chloroform extraction. *Anal. Biochem.* 162:156-159.
3. Choo, Q. L., G. Kuo, A. J. Weiner, L. R. Overby, D. W. Bradley, and M. Houghton. 1989. Isolation of a cDNA derived from a blood-borne non-A, non-B hepatitis genome. *Science* 244: 359-362.
4. Choo, Q. L., K. H. Richman, J. H. Han, K. Berger, C. Lee, C. Dong, C. Gallegos, D. Colt, R. Medina Selby, P. J. Barr, A. J. Weiner, D. W. Bradley, G. Kuo, and M. Houghton. 1991. Genetic organization and diversity of the hepatitis C virus, *Proc. Natl. Acad. Sci. U.S.A.* 88: 2451-2455.
5. Coeien, R. J. and J. S. Mackenzie. 1990. The 5' terminal non-coding region of Murray Valley encephalitis virus RNA is highly conserved. *J. Gen. Virol.* 71:241-245.
6. Devereux, J., P. Haeberii, and O. Smithies. 1984. Comprehensive set of sequence analysis programs for the VAX. *Nucleic Acids. Res.* 12:387-395.
7. Enomoto, N., A. Takada, T. Nakao, and T. Date. 1990. There are two major types of hepatitis C virus in Japan. *Biochem Biophys. Res. Commun.* 170:1021-1025.
8. Esteban, J. L., A. Gonzaiez, J. M. Hernandez, L. Viladomiu, C. Sanchez, J. C. Lopez Talavera, D. Lucea, C. Martin Vega, X. Vidal, R. Estaban, and J. Guardia. 1990. Evaluation of antibodies to hepatitis C virus in a study of transfusion-associated hepatitis. *N. Engl. J. Med.* 323:1107-1112.
9. Felsenstein, J. 1988. Phylogenies from molecular sequences: inference and reliability. *Ann. Rev. Genet.* 22:521-565.
10. 10. Follett, E. A. C., B. C. Dow, F. McOmish, P. L. Yap, W. Hughes, R. Mitchell, and P. Simmonds. 1991. HCV confirmatory testing of blood donors. *Lancet* 338:1024.
11. Fuchs, K., M. Motz, E. Schreir, R. Zachoval, F. Deinhardt, and M. Roggendorf. 1991. Characterization of nucleotide sequences from European hepatitis C virus isolates. *Gene* 103:163-169.
12. Garson, J. A., C. Ring, P. Tuke, and R. S. Tedder. 1990 Enhanced detection by PCR of hepatitis C virus RNA. *Lancet* 336:878-879.
12a. Geysen, H. M., Barteling, S. J. and Meloen, R. H. (1985). *Proc Natl Acad Sci U.S.A.* 82:178-182.
12b. Geysen, H. M., Meloen, R. H. and Barteling, S. J. (1984). *Proc Natl Acad Sci U.S.A.:* 81:3998-4003.
13. Han, J. H., V. Shyamaia, K. H., Richman, M. J. Brauer, B. Irvine, M. S. Urdea, P. Tekamp Olson, G. Kuo, Q. L. Choo, and M. Houghton. 1991. Characterization of the terminal regions of hepatitis C viral RNA identification of conserved sequences in the 5' untranslated region and poly(A) tails at the 3' end. *Proc. Natl. Acad. Sci. U.S.A.* 88:1711-1715.
14. Hosien, B., C. T. Fang, M. A. Popovsky, J. Ye, M. Zhang, and C. Y. Wang. 1991. Improved serodiagnosis of hepatitis C virus infection with synthetic peptide antigen from capsid protein. *Proc. Natl. Acad. Sci. U.S.A.* 88:3647-3651.
15. Japanese Red Cross Non-A. Non-B Hepatitis Research Group 1991. Effect of screening for hepatitis C virus antibody and hepatitis B virus core antibody on the incidence of post-transfusion hepatitis. *Lancet* 338:1040-1041.
16. Kato, N., M. Hijikata, Y. Ootsuyama, M. Nakagawa, S. Ohkoshi, T. Sugimura, and K. Shimotohno. 1990. Molecular cloning of the human hepatitis C virus genome from Japanese patients with non-A, non-B hepatitis. *Proc. Natl. Acad. Sci. U.S.A.* 87:9524-9528.
17. Kubo, Y., K. Takeuchi, S. Boonmar, T. Katayama, Q. L. Choo, G. Kuo, A. J. Weiner, D. W. Bradley, M. Houghton, I. Saito, and T. Miyamura. 1989. A cDNA fragment of hepatitis C virus isolated from an implicated donor of post-transfusion non-A, non-B hepatitis in Japan. *Nucleic Acids. Res.* 17:10367-10372.
18. Kuo, G., Q. L. Choo, H. J. Alter, G. L. Gitnick, A. G. Redeker, R. H. Purcell, T. Miyamura, J. L. Dienstag, M. J. Alter, C. E. Stevens, G. E. Tegtmeier, F. Bonino, M. Columbo, W. S. Less, C. Kuo, K. Berger, J. R. Shuster, L. R. Overby, D. W. Bradley, and M. Houghton. 1989. An assay for circulating antibodies to a major etiologic virus of human non-A, non-B hepatitis. *Science* 244:362-364.
19. Lain, S., J. L. Reichmann, M. T. Martin, and J. A. Garcia, 1989. Homologous polyvirus and flavivirus proteins belonging to a superfamily or helicase-like proteins. *Gene* 82:357-362.
20. Mandl, C. W., F. X. Heinz, and C. Kunz. 1988. Sequence of the structural proteins of tick-borne encephalitis virus (Western subtype) and comparative analysis with other flaviviruses. *Virology* 166:197-205.
21. Miller, R. H. and R. H. Purcell. 1990. Hepatitis C virus shares amino acid sequence similarity with pestiviruses and flaviviruses as well as members of two plant virus supergroups. *Proc. Natl. Acad. Sci. U.S.A.* 87:2057-2061.
22. Muraiso, K., M. Hijikata, S. Ohkoshi, M. J. Cho, M. Kikuchi, N. Kato, and K. Shimotohno, 1990. A structural protein of hepatitis C virus expressed in *E. coli* facilitates accurate detection of hepatitis C virus. *Biochem. Biophys. Res. Commun.* 172:511-516.
23. Nakao, T., N. Enomoto, N. Takada, A. Takada, and T. Date. 1991. Typing of hepatitis C virus (HCV) genomes by restriction fragment length polymorphisms. *J. Gen. Virol.* 72: 2105-2112.
24. Ogata, N., H. J. Alter, R. H. Miller, and R. H. Purcell. 1991. Nucleotide sequence and mutation rate of the H strain of hepatitis C virus. *Proc. Natl. Acad. Sci. U.S.A.* 88: 3392-3396.
25. Okamoto, H., S. Okada, Y. Sugiyama, T. Tanaka, Y. Sugai, Y. Akahane, A. Machida, S. Mishiro, H. Yoshizawa, Y. Miyakawa, and M. Mayumi. 1990. Detection of hepatitis C virus RNA by a two-stage polymerase chain reaction with two pairs of primers deduced from the 5'-noncoding region. *Jpn. J. Exp. Med.* 60:215-222.
26. Okamoto, H., S. Okada, Y. Sugiyama, S. Yotsumoto, T. Tanaka, H. Yoshizawa, F. Tsuda, Y. Miyakawa, and M. Mayumi. 1990. The 5'-terminal sequence of the hepatitis C virus genome. *Jpn. J. Exp. Med.* 60: 167-177.
27. Pozzato, G., M. Moretti, F. Franzin, L. S. Croce, C. Tiribelli, T. Masayu, S. Kaneko, M. Unoura, and K. Kobayashi. 1991. Severity or liver disease with different hepatitis C viral clones. *Lancet* 338:509.
28. Saiton, N. and T. Imanishi. 1989. Relative efficiencies of the Fitch-Margoliash, maximum-parsimony, maximum-likelihood, minimum evolution, and neighbor-joining methods of phylogenetic tree construction in obtaining the correct tree. *Mol. Biol. Evol.* 6: 514-525.
29. Saitou, N. and M. Nei. 1987. The neighbor-joining method: a new method for reconstructing phylogenetic trees. *Mol. Biol. Evol.* 4:406-425.
30. Simmonds, P., P. Balfe, J. F. Peutherer, C. A. Ludlam, J. O. Bishop, and A. J. Leigh Brown. 1990. Human immunodeficiency virus-infected individuals contain provirus in small numbers of peripheral mononuclear cells and at low copy numbers. *J. Virol.* 64:864-872.
31. Simmonds, P., L. Q. Zhang, H. G. Watson, S. Rebus, E. D. Ferguson, P. Balfe, G. H. Leadbetter, P. L. Yap, J. F. Peutherer, and C. A. Ludlam. 1990. Hepatitis C quantification and sequencing in blood products, haemophiliacs, and drug users. *Lancet* 336:1469-1472.
32. Staden, R. 1984. Graphic methods to determine the function of nucleic acid sequences. *Nucleic Acids. Res.* 12: 521-538.
33. Takamizawa, A., C. Mori, I. Fuke, S. Manabe, S. Murakami, J. Fujita, E. Onishi, T. Andoh, I. Yoshida, and H. Okayama. 1991. Structure and organization of the hepatitis C virus genome isolated from human carriers. *J. Virol.* 65:1105-1113.
34. Takeuchi, K., Y. Kubo, S. Boonmar, Y. Watanabe, T. Katayama, Q. L. Choo, G. Kuo, M. Houghton, I. Saito, and T. Miyamura. 1990. Nucleotide sequence of core and envelope genes of the hepatitis C virus genome derived directly from human healthy carriers. *Nucle. Acids. Res.* 18:4626.
35. Ksukiyama-Kohara, K., M. Kohara, K. Yamaguchi, N. Maki, A. Toyoshima, K. Miki, S. Tanaka, N. Hattori, and A. Nomoto. 1991. A second group of hepatitis C virus. *Virus Genes* 5: 243-254.
36. van der Poel, C. L., H. T. Cuypers, H. W. Reesink, A. J. Weiner, S. Quan, R. Di Nello, J. J. Van Boven, I. Winkel, D. Mulder Folkerts, P. J. Exel Oehlers, W. Schaasberg, A. Leentvaar-Kuypers, A. Polito, M. Houghton, and P. N. Lelie. 1991. Confirmation of hepatits C virus infection by new four-antigen recombinant immunoblot assay. *Lancet* 337:317-319.
37. Weiner, A. J., G. Kuo, D. W. Bradley, F. Bonino, G. Saracco, C. Lee, J. Rosenblatt, Q. L. Choo, and M. Houghton. 1990. Detection of hepatitis C viral sequences in non-A, non-B hepatitis (see comments). *Lancet* 335: 1-3.

The invention claimed is:

1. A method for detecting HCV infection in a mammal, comprising:
   a) obtaining a blood sample from a mammal;
   b) isolating RNA from said blood sample;
   c) reverse transcribing said RNA intro cDNA;
   d) performing PCR on said cDNA using sense and antisense primers specific for HCV, wherein said sense and antisense primers are selected from the group consisting of:
      1) SEQ ID NO:42 and SEQ ID NO:41;
      2) SEQ ID NO:43 and SEQ ID NO:40; and
      3) SEQ ID NO:43 and SEQ ID NO:41; and
   e) determining whether HCV infection was detected by analyzing the results from said PCR.

* * * * *